United States Patent
Rubin et al.

(10) Patent No.: US 10,253,101 B2
(45) Date of Patent: Apr. 9, 2019

(54) ANTIBODY FRAGMENTS AGAINST THE INSULIN RECEPTOR AND USES THEREOF TO TREAT HYPOGLYCEMIA

(71) Applicant: XOMA (US) LLC, Berkeley, CA (US)

(72) Inventors: Paul Rubin, San Francisco, CA (US); Toshihiko Takeuchi, Oakland, CA (US); Hassan Issafras, Kensington, CA (US); Kiranjit Ahluwalia, Fremont, CA (US); John Corbin, Oakland, CA (US); Ira Goldfine, Belvidere, CA (US); Kirk Johnson, Moraga, CA (US); Ou Li, Dublin, CA (US); Daniel Bedinger, Pleasant Hill, CA (US)

(73) Assignee: XOMA (US) LLC, Emeryville, CA (US)

( * ) Notice: Subject to any disclaimer, the term of this patent is extended or adjusted under 35 U.S.C. 154(b) by 16 days.

(21) Appl. No.: 15/230,340

(22) Filed: Aug. 5, 2016

(65) Prior Publication Data

US 2017/0037135 A1    Feb. 9, 2017

Related U.S. Application Data

(60) Provisional application No. 62/280,675, filed on Jan. 19, 2016, provisional application No. 62/202,143, filed on Aug. 6, 2015.

(51) Int. Cl.
  *C07K 16/28*   (2006.01)
  *A61K 39/395*  (2006.01)
  *A61K 45/06*   (2006.01)
  *A61K 39/00*   (2006.01)

(52) U.S. Cl.
  CPC .... *C07K 16/2869* (2013.01); *A61K 39/39541* (2013.01); *A61K 45/06* (2013.01); *A61K 2039/505* (2013.01); *A61K 2039/54* (2013.01); *A61K 2039/545* (2013.01); *C07K 2317/21* (2013.01); *C07K 2317/33* (2013.01); *C07K 2317/40* (2013.01); *C07K 2317/55* (2013.01); *C07K 2317/565* (2013.01); *C07K 2317/567* (2013.01); *C07K 2317/76* (2013.01); *C07K 2317/90* (2013.01); *C07K 2317/92* (2013.01); *C07K 2317/94* (2013.01)

(58) Field of Classification Search
  CPC ............ C07K 16/2869; C07K 2317/21; C07K 2317/33; C07K 2317/55; C07K 2317/56; C07K 2317/565; C07K 2317/76; C07K 2317/92; C07K 2317/94; A61K 39/39541; A61K 39/3955; A61K 45/06; A61K 2039/505; A61K 2039/54; A61K 2039/545
  See application file for complete search history.

(56) References Cited

U.S. PATENT DOCUMENTS

| | | |
|---|---|---|
| 4,179,337 A | 12/1979 | Davis et al. |
| RE30,985 E | 6/1982 | Cartaya |
| 4,560,655 A | 12/1985 | Baker |
| 4,657,866 A | 4/1987 | Kumar |
| 4,767,704 A | 8/1988 | Cleveland et al. |
| 4,816,567 A | 3/1989 | Cabilly et al. |
| 4,927,762 A | 5/1990 | Darfler |
| 4,975,278 A | 12/1990 | Senter et al. |
| 5,057,313 A | 10/1991 | Shih et al. |
| 5,122,469 A | 6/1992 | Mather et al. |
| 5,223,409 A | 6/1993 | Ladner et al. |
| 5,229,275 A | 7/1993 | Goroff |
| 5,348,867 A | 9/1994 | Georgiou et al. |
| 5,463,768 A | 10/1995 | Cuddihy et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,573,905 A | 11/1996 | Lerner et al. |
| 5,589,369 A | 12/1996 | Seidman et al. |
| 5,658,754 A | 8/1997 | Kawasaki |
| 5,723,287 A | 3/1998 | Russell et al. |
| 5,766,886 A | 6/1998 | Studnicka et al. |
| 5,877,293 A | 3/1999 | Adair et al. |
| 5,939,598 A | 8/1999 | Kucherlapati et al. |
| 5,969,108 A | 10/1999 | McCafferty et al. |
| 6,054,287 A | 4/2000 | Gao et al. |
| 6,091,001 A | 7/2000 | Jakobovits et al. |
| 6,114,598 A | 9/2000 | Kucherlapati et al. |
| 6,194,551 B1 | 2/2001 | Idusogie et al. |
| 6,306,393 B1 | 10/2001 | Goldenberg |
| 6,657,103 B1 | 12/2003 | Kucherlapati et al. |
| 6,699,658 B1 | 3/2004 | Wittrup et al. |
| 6,833,268 B1 | 12/2004 | Green et al. |
| 8,926,976 B2 | 1/2015 | Corbin et al. |

(Continued)

FOREIGN PATENT DOCUMENTS

EP       2036574 A1    3/2009
WO    WO-81/01145 A1   4/1981

(Continued)

OTHER PUBLICATIONS

Adams et al., Structure and function of the type 1 insulin-like growth factor receptor, Cell Mol. Life Sci., 57(7)1050-93 (2000).

(Continued)

*Primary Examiner* — Robert S Landsman

(74) *Attorney, Agent, or Firm* — Marshall, Gerstein & Borun LLP

(57) ABSTRACT

The present disclosure relates, in general, to methods of treating or preventing hypoglycemia using a negative modulator antibody fragment that binds to the insulin receptor and modulates the action of insulin at the insulin receptor.

33 Claims, 29 Drawing Sheets

Specification includes a Sequence Listing.

(56) References Cited

U.S. PATENT DOCUMENTS

| | | |
|---|---|---|
| 9,102,711 B2 | 8/2015 | Takeuchi |
| 2002/0004215 A1 | 1/2002 | Osbourn et al. |
| 2002/0199213 A1 | 12/2002 | Tomizuka et al. |
| 2003/0031667 A1 | 2/2003 | Deo et al. |
| 2003/0092125 A1 | 5/2003 | Davis et al. |
| 2003/0118592 A1 | 6/2003 | Ledbetter et al. |
| 2003/0133939 A1 | 7/2003 | Ledbetter et al. |
| 2003/0190317 A1 | 10/2003 | Baca et al. |
| 2003/0194404 A1 | 10/2003 | Greenfeder et al. |
| 2005/0037421 A1 | 2/2005 | Honda et al. |
| 2005/0136049 A1 | 6/2005 | Ledbetter et al. |
| 2011/0274692 A1 | 11/2011 | White et al. |
| 2014/0128803 A1 | 5/2014 | Dobbles et al. |
| 2016/0009800 A1 | 1/2016 | Corbin et al. |

FOREIGN PATENT DOCUMENTS

| | | |
|---|---|---|
| WO | WO-87/00195 A1 | 1/1987 |
| WO | WO-88/07378 A1 | 10/1988 |
| WO | WO-91/00906 A1 | 1/1991 |
| WO | WO-91/17271 A1 | 11/1991 |
| WO | WO-92/01047 A1 | 1/1992 |
| WO | WO-92/09690 A2 | 6/1992 |
| WO | WO-92/15679 A1 | 9/1992 |
| WO | WO-92/18619 A1 | 10/1992 |
| WO | WO-92/20791 A1 | 11/1992 |
| WO | WO-93/01288 A1 | 1/1993 |
| WO | WO-94/02602 A1 | 2/1994 |
| WO | WO-96/11953 A1 | 4/1996 |
| WO | WO-96/30498 A1 | 10/1996 |
| WO | WO-96/32478 A1 | 10/1996 |
| WO | WO-96/33735 A1 | 10/1996 |
| WO | WO-96/34096 A1 | 10/1996 |
| WO | WO-98/24893 A2 | 6/1998 |
| WO | WO-99/10494 A2 | 3/1999 |
| WO | WO-03/041600 A1 | 5/2003 |
| WO | WO-04/050016 A2 | 6/2004 |
| WO | WO-2011/038301 A2 | 3/2011 |
| WO | WO-2011/038302 A2 | 3/2011 |
| WO | WO-2016/141111 A1 | 9/2016 |

OTHER PUBLICATIONS

Alewine et al., Advances in anticancer immunotoxin therapy, Oncologist, 20(2)1 76-85 (2015).

Allen et al., Nocturnal hypoglycemia: clinical manifestations and therapeutic strategies toward prevention, Endocr. Pract., 9(6):530-43 (2003).

Amstutz et al., In vitro display technologies: novel developments and applications, Curr. Opin. Biotechnol., 12(4):400-5 (2001).

Arnoux et al., Congenital hyperinsulinism: current trends in diagnosis and therapy, Orphanet J. Rare Dis., 6:63 (2011).

Barbas et al., Assembly of combinatorial antibody libraries on phage surfaces: the gene III site, Proc. Natl. Acad. Sci. USA, 88(18):7978-82 (1991).

Barnes et al., Methods for growth of cultured cells in serum-free medium, Anal. Biochem., 102(2):255-70 (1980).

Batra et al., Recombinant anti-erbB2 immunotoxins containing Pseudomonas exotoxin, Proc. Natl. Acad. Sci. USA, 89(13):5867-71 (1992).

Bayer et al., The avidin-biotin complex in affinity cytochemistry, Methods Enzymol., 62:308-15 (1979).

Becker et al., An antibody-interleukin 2 fusion protein overcomes tumor heterogeneity by induction of a cellular immune response, Proc. Natl. Acad. Sci. USA, 93(15):7826-31 (1996).

Better et al., *Escherichia coli* secretion of an active chimeric antibody fragment, Science, 240(4855):1041-3 (1988).

Better et al., Potent anti-CD5 ricin A chain immunoconjugates from bacterially produced Fab' and F(ab')2. *Proc. Natl. Acad. Sci. USA.* 90: 457-61 (1993).

Biocca et al., Expression and targeting of intracellular antibodies in mammalian cellls. *EMBO.* 9: 101-8 (1990).

Birch et al., Antibody production, Adv. Drug Deliv. Rev., 58(5-6):671-85 (2006).

Bird et al., Single-chain antigen binding protein. *Science.* 242: 423-6 (1988).

Boado et al., Humanization of anti-human insulin receptor antibody for drug targeting across the human blood-brain barrier, Biotechnol. Bioeng., 96(2):381-91 (2007).

Boleti et al., Construction, expression and characterisation of a single chain anti-tumour antibody (scFv)-IL-2 (fusion protein, Ann. Oncol., 6(9):945-7 (1995).

Boulianne et al., Production of functional chimaeric mouse/human antibody. *Nature.* 312: 643-6 (1984).

Brindle et al., Anti-(insulin receptor) monoclonal antibody-stimulated tyrosine phosphorylation in cells transfected with human insulin receptor cDNA, Biochem. J., 268:615-20 (1990).

Brinkmann et al., B3(Fv)-PE38KDEL, a single-chain immunotoxin that causes complete regression of a human carcinoma in mice, Proc. Natl. Acad. Sci. USA, 88(19):8616-20 (1991).

Bruggermann et al., Designer mice: the production of human antibody repertoires in transgenic animals, Year Immunol., 7:33-40 (1993).

Brunton, Nocturnal hypoglycemia: answering the challenge with long-acting insulin analogs, MedGen Med, 9(2):38 (2007).

Burton et al., Human antibodies from combinatorial libraries, Adv. Immunol., 57:191-280 (1994).

Caron et al., Engineered humanized dimeric forms of IgG are more effective antibodies, J. Exp. Med., 176(4):1191-5 (1992).

Carter et al., High level *Escherichia coli* expression and production of a bivalent humanized antibody fragment. *Bio/Technology* 10: 163-7 (1992).

Caton et al., Influenza virus hemagglutinin-specific antibodies isolated from a combinatorial expression library are closely related to the immune response of the donor, Proc. Natl. Acad. Sci. USA, 87(16):6450-4 (1990).

Chaudhary et al., A recombinant immunotoxin consisting of two antibody variable domains fused to Pseudomonas exotoxin, Nature, 339(6223):394-7 (1989).

Chothia et al., Canonical structures for the hypervariable regions of immunoglobulins, J. Mol. Biol., 196(4):901-17 (1987).

Chothia et al., Conformations of immunoglobulin hypervariable regions, Nature, 342(6252):877-83 (1989).

Clackson et al., Making antibody fragments using phage display libraries, Nature, 352(6336):624-8 (1991).

Colby et al., Potent inhibition of huntingtin aggregation and cytotoxicity by a disulfide bond-free single-domain intracellular antibody. *Proc Natl Acad Sci USA.* 101: 17616-21 (2004).

De Meyts, Insulin and its receptor: structure, function and evolution, Bioessays, 26(12):1351-62 (2004).

Denley et al., Structural determinants for high-affinity binding of insulin-like growth factor II to insulin receptor (IR)-A, the exon 11 minus isoform of the IR, Mol. Endocrinol., 18(10:2502-12 (2004).

Denley et al., The insulin receptor isoform exon 11- (IR-A) in cancer and other diseases: a review, Horm. Metab. Res., 35(11-12):778-85 (2003).

Deonarain et al., Construction, refolding and cytotoxicity of a single chain Fv-seminal ribonuclease fusion protein expressed in *Escherichia coli,* Tumor Targeting, 1:177 (1995).

Desmyter et al., Antigen specificity and high affinity binding provided by one single loop of a camel single-domain antibody, J. Biol. Chem., 276(28):26285-90 (2001).

Dohlsten et al., Monoclonal antibody-superantigen fusion proteins: tumor-specific agents for T-cell-based tumor therapy, Proc. Natl. Acad. Sci. USA, 91(19):8945-9 (1994).

Doronina et al., Development of potent monoclonal antibody auristatin conjugates for cancer therapy, Nat. Biotechnol., 21(7):778-84 (2003).

Douillard et al., Hypoglycaemia related to inherited metabolic diseases in adults, Orphanet J. Rare Dis., 7:26 (2012).

Duckworth et al., Insulin degradation: progress and potential, Endocr. Rev., 19(5):608-24 (1998).

(56) References Cited

OTHER PUBLICATIONS

Engvall et al., Enzyme-linked immunosorbent assay, Elisa. 3. Quantitation of specific antibodies by enzyme-labeled anti-immunoglobulin in antigen-coated tubes, J. Immunol., 109(1):129-35 (1972).
Evan et al., Isolation of monoclonal antibodies specific for human c-myc proto-oncogene product, Mol. Cell Biol., 5(12):3610-6 (1985).
Ewert et al., Biophysical properties of camelid $V_{HH}$ domains compared to those of human $V_H3$ domains. *Biochemisrty* 41: 3628-36 (2002).
Eyer et al., Single-domain antibody fragments derived from heavy-chain antibodies: a review, Veterinarni Medicina, 57:439-513 (2012).
Ferrara et al., Modulation of therapeutic antibody effector functions by glycosylation engineering: influence of Golgi enzyme localization domain and co-expression of heterologous beta1, 4-N-acetylglucosaminyltransferase III and Golgi alpha-mannosidase II, Biotechnol. Bioeng., 93(5):851-61 (2006).
Field et al., Purification of a RAS-responsive adenylyl cyclase complex from Saccharomyces cerevisiae by use of an epitope addition method, Mol. Cell Biol., 8(5):2159-65 (1988).
Fishwild et al., High-avidity human IgG kappa monoclonal antibodies from a novel strain of minilocus transgenic mice, Nat. Biotechnol., 14(7):845-51 (1996).
Fix, Strategies for delivery of peptides utilizing absorption-enhancing agents, J. Pharm. Sci., 85(12):1282-5 (1996).
Fominaya et al., Target cell-specific DNA transfer mediated by a chimeric multidomain protein. Novel non-viral gene delivery system, J. Biol. Chem., 271(18)1 0560-8 (1996).
Forsayeth et al., Effect of monoclonal antibodies on human insulin receptor autophosphorylation, negative cooperativity, and down-regulation, J. Biol. Chem., 262(9):4134-40 (1987).
Forsayeth et al., Monoclonal antibodies to the human insulin receptor that activate glucose transport but not insulin receptor kinase activity, Proc. Natl. Acad. Sci. USA, 84(10):3448-51 (1987).
Frenzel et al., Expression of recombinant antibodies, Front Immunol., 4:217 (2013).
Friedman et al., Antitumor activity of the single-chain immunotoxin BR96 sFv-PE40 against established breast and lung tumor xenografts, J. Immunol., 150(7):3054-61 (1991).
Fuchs et al., Targeting recombinant antibodies to the surface of *Escherichia coli*: fusion to a peptidoglycan associated lipoprotein, Bio/Technology, 9:1369-73 (Dec. 1991).
Ganderton et al., A monoclonal anti-peptide antibody reacting with the insulin receptor beta-subunit. Characterization of the antibody and its epitope and use in immunoaffinity purification of intact receptors, Biochem. J., 288 (Pt.1):195-205 (1992).
Garrard et al., Fab assembly and enrichment in a monovalent phage display system, Bio/Technology, 9(12):1373-7 (1991).
Geller et al., National estimates of insulin-related hypoglycemia and errors leading to emergency department visits and hospitalizations, JAMA Intern. Med., 174(5):678-86 (2014).
Gill et al., Expression of prolactin receptors in normal, benign, and malignant breast tissue: an immunohistological study. *J. Clin. Pathol.* 54: 956-60 (2001).
Goding, Conjugation of antibodies with fluorochromes: modifications to the standard methods, J. Immunol. Methods, 13(3-4):215-26 (1976).
Goldenberg, New developments in monoclonal antibodies for cancer detection and therapy, CA Cancer J. Clin., 44(1):43-64 (1994).
Goodman et al., Antibody binding to the juxtamembrane region of the insulin receptor alters receptor affinity, J. Recept. Res., 14(6-8):381-98 (1994).
Graham et al., Characteristics of a human cell line transformed by DNA from human adenovirus type 5. *J. Gen. Virol.* 36: 59-74 (1977).
Gram et al., In vitro selection and affinity maturation of antibodies from a naive combinatorial immunoglobulin library, Proc. Natl. Acad. Sci. USA, 89(8):3576-80 (1992).
Green et al., Transgenic mouse strains as platforms for the successful discovery and development of human therapeutic monoclonal antibodies, Curr. Drug Discov. Technol., 11(1):74-84 (2014).

Greenberg et al., A new antigen receptor gene family that undergoes rearrangement and extensive somatic diversification in sharks, Nature, 374(6518):168-73 (1995).
Griffiths et al., Human anti-self antibodies with high specificity from phage display libraries, EMBO J., 12(2):725-34 (1993).
Guss et al., Structure of the IgG-binding regions of streptococcal protein G. *EMBO* 5: 1567-75 (1986).
Ham et al., Media and growth requirements, Methods Enzymol., 58:44-93 (1979).
Hamers-Casterman et al., Naturally occurring antibodies devoid of light chains, Nature, 363(6428):446-8 (1993).
Hanes et al., In vitro selection and evolution of functional proteins by using ribosome display, Proc. Natl. Acad. Sci. USA, 94(10):4937-42 (1997).
Hank et al., Activation of human effector cells by a tumor reactive recombinant anti-ganglioside GD2 interleukin-2 fusion protein (ch14.18-1L2), Clin. Cancer Res., 2(12):1951-9 (1996).
Hawkins et al., Selection of phage antibodies by binding affinity. Mimicking affinity maturation, J. Mol. Biol., 226(3):889-96 (1992).
Hay et al., Bacteriophage cloning and *Escherichia coli* expression of a human IgM Fab, Hum. Antibodies Hybridomas, 3(2):81-5 (1992).
Heng et al., Making cell-permeable antibodies (Transbody) through fusion of protein transduction domains (PTD) with single chain variable fragment (scFv) antibodies: potential advantages over antibodies expressed within the intracellular environment (Intrabody). *Med. Hypotheses*, 64: 1105-8 (2005).
Hinman et al., Preparation and characterization of monoclonal antibody conjugates of the calicheamicins: a novel and potent family of antitumor antibiotics, Cancer Res., 53(14):3336-42 (1993).
Holliger et al., "Diabodies": small bivalent and bispecific antibody fragments, Proc. Natl. Acad. Sci. USA, 90(14):6444-8 (1993).
Holliger et al., Engineered antibody fragments and the rise of single domains, Nat. Biotechnol., 23(9):1126-36 (2005).
Hoogenboom et al., By-passing immunisation. Human antibodies from synthetic repertoires of germline VH gene segments rearranged in vitro, J. Mol. Biol., 227(2):381-8 (1992).
Hoogenboom et al., Multi-subunit proteins on the surface of filamentous phage: methodologies for displaying antibody (Fab) heavy and light chains, Nucleic Acids Res., 19(15):413-7 (1991).
Hu et al., A chimeric Lym-1/interleukin 2 fusion protein for increasing tumor vascular permeability and enhancing antibody uptake, Cancer Res., 56(21):4998-5004 (1996).
Huse et al., Generation of a large combinatorial library of the immunoglobulin repertoire in phage lambda, Science, 246-1275-81 (1989).
Huston et al., Protein engineering of antibody binding sites: Recovery of specific activity in an anti-digoxin single-chain Fv analogue produced in *Escherichia coli. Proc. Natl. Acad. Sci. USA.* 85: 5879-83 (1988).
Ishida et al., Production of human monoclonal and polyclonal antibodies in TransChromo animals, Cloning Stem Cells, 4(1):91-102 (2002).
Jakobovits et al., Analysis of homozygous mutant chimeric mice: deletion of the immunoglobulin heavy-chain joining region blocks B-cell development and antibody production, Proc. Natl. Acad. Sci. USA, 90(6):2551-5 (1993).
Jakobovits et al., Germ-line transmission and expression of a human-derived yeast artificial chromosome, Nature, 362(6417):255-8 (1993).
Jespers et al., Guiding the selection of human antibodies from phage display repertoires to a single epitope of an antigen, Biotechnology (NY), 12(9):899-903 (1994).
Jones et al., Replacing the complementarity-determining regions in a human antibody with those from a mouse, Nature, 321(6069):522-5 (1986).
Kabat et al., Sequences of Proteins of Immunological Interests, National Institutes of Health, Bethesda, Md., (1987 and 1991).
Kang et al., Antibody redesign by chain shuffling from random combinatorial immunoglobulin libraries, Proc. Natl. Acad. Sci. USA, 88(24):11120-3 (1991).

(56) References Cited

OTHER PUBLICATIONS

Kettleborough et al., Humanization of a mouse monoclonal antibody by CDR-grafting: the importance of framework residues on loop conformation, Protein Eng., 4(7):773-83 (1991).
Kitamura et al., Insulin receptor knockout mice, Annu. Rev. Physiol., 65:313-32 (2003).
Kohler et al., Continuous cultures of fused cells secreting antibody of predefined specificity, Nature, 256(5517):495-7 (1975).
Kreitman et al., Cytotoxic activities of recombinant immunotoxins composed of Pseudomonas toxin or diphtheria toxin toward lymphocytes from patients with adult T-cell leukemia, Leukemia, 7(4):553-62 (1993).
Kuan et al., Recombinant immunotoxin containing a disulfide-stabilized Fv directed at erbB2 that does not require proteolytic activation, Biochemistry, 35(9):2872-7 (1996).
Lebrun et al., Antibodies to the extracellular receptor domain restore the hormone-insensitive kinase and conformation of the mutant insulin receptor valine 382, J. Biol. Chem., 268(15):11272-7 (1993).
Lee et al., Microbial cell-surface display, Trends Biotechnol., 21(1):45-52 (2003).
Levy et al., Enhancement of antibody fragment secretion into the *Escherichia coli* periplasm by co-expression with the peptidyl prolyl isomerase, FkpA, in the cytoplasm, J. Immunol. Methods, 394(1-2):10-21 (2013).
Li et al., Comparison of the long-term results of Roux-en-Y gastric bypass and sleeve gastrectomy for morbid obesity: a systematic review and meta-analysis of randomized and nonrandomized trials, Surg. Laparosc. Endosc. Percutan. Tech., 24(1):1-11 (2014).
Linardou et al., Deoxyribonuclease I (DNAse I). A novel approach for targeted cancer therapy, Cell Biophys., 25:243-8 (1994).
Lindmark et al., Binding of immunoglobulins to protein A and immunoglobulin levels in mammalian sera. *J. Immunol. Meth.* 62: 1-13 (1983).
Liu et al., Eradication of large colon tumor xenografts by targeted delivery of maytansinoids, Proc. Natl. Acad. Sci. USA, 93(16):8618-23 (1996).
Lode et al., Targeted therapy with a novel enediyne antibiotic calicheamicin $\Theta^1$, effectively suppresses growth and dissemination of liver metastases in a syngeneic model of murine neuroblastoma, Cancer Res., 58:2925-8 (1998).
Mandler et al., Immunoconjugates of geldanamycin and anti-HER2 monoclonal antibodies: antiproliferative activity on human breast carcinoma cell lines, J. Natl. Cancer Inst., 92(19):1573-81 (2000).
Mandler et al., Synthesis and evaluation of antiproliferative activity of a geldanamycin-Herceptin immunoconjugate, Bioorg. Med. Chem. Lett., 10(10):1025-8 (2000).
Marks et al., By-passing immunization. Human antibodies from V-gene libraries displayed on phage, J. Mol. Biol., 222(3):581-97 (1991).
Marks et al., By-passing immunization: building high affinity human antibodies by chain shuffling, Biotechnology (NY), 10(7):779-83 (1992).
Massey, Catalytic antibodies catching on, Nature, 328:457-8 (1987).
Mather et al., Culture of testicular cells in hormone-supplemented serum-free medium. *Annals N.Y. Acad. Sci.* 383: 44-68 (1982).
Mather, . Establishment and characterization of two distinct mouse testicular epithelial cell lines. *Biol. Reprod.* 23: 243-251 (1980).
Matyka et al., Hypoglycaemia and counterregulation during childhood, Horm. Res., 57 Suppl 1:85-90 (2002).
Mc Kern et al., Structure of the insulin receptor ectodomain reveals a folded-over conformation, Nature, 443:218-21 (2006).
McCafferty et al., Phage antibodies: filamentous phage displaying antibody variable domains, Nature, 348(6301):552-4 (1990).
Mhashilkar et al., Inhibition of HIV-1 Tat-mediated LTR transaction and HIV-1 infection by anti-Tat single chain intrabodies. *EMBO J.* 14 (7):1542-51, 1995.
Morgan et al., Insulin action is blocked by a monoclonal antibody that inhibits the insulin receptor kinase, Proc. Natl. Acad. Sci. USA, 83(2):328-32 (1986).

Morrison et al., Chimeric human antibody molecules: mouse antigen-binding domains with human constant region domains, Proc. Natl. Acad. Sci. USA, 81(21):6851-5 (1984).
Morrison et al., Genetically engineered antibody molecules, Adv. Immunol., 44:65-92 (1989).
Natsume et al., Improving effector functions of antibodies for cancer treatment: Enhancing ADCC and CDC, Drug Des. Devel. Ther., 3:7-16 (2009).
Neuberger et al., Recombinant antibodies possessing novel effector functions, Nature, 312(5995):604-8 (1984).
Nicholls et al., Characterization of single-chain antibody (sFv)-toxin fusion proteins produced in vitro in rabbit reticulocyte lysate, J. Biol. Chem., 268(7):5302-8 (1993).
Nicolet et al., Expression of a tumor-reactive antibody-interleukin 2 fusion protein after in vivo particle-mediated gene delivery, Cancer Gene Ther., 2(3):161-70 (1995).
Niwa et al., The current status and prospects of antibody engineering for therapeutic use: focus on glycoengineering technology, J. Pharm. Sci., 104(3):930-41 (2015).
Nuttall et al., Isolation of the new antigen receptor from wobbegong sharks, and use as a scaffold for the display of protein loop libraries, Mol. Immunol., 38(4):313-26 (2001).
Olafsen et al., Characterization of engineered anti-p185HER-2 (scFv-CH3)2 antibody fragments (minibodies) for tumor targeting. *Protein Eng. Des. Sel.* 17: 315-23 (2004).
Oliyai et al., Prodrugs of peptides and proteins for improved formulation and delivery, Annu. Rev. Pharmacol. Toxicol., 33:521-44 (1993).
Omidfar et al., Advances in phage display technology for drug discovery, Expert Opin. Drug Discov., 10(6):651-69 (2015).
Owens et al., Alternative routes of insulin delivery, Diabet. Med., 20(11):886-98 (2003).
Paborsky et al., Mammalian cell transient expression of tissue factor for the production of antigen, Protein Eng., 3(6):547-53 (1990).
Padlan, A possible procedure for reducing the immunogenicity of antibody variable domains while preserving their ligand-binding properties, Mol. Immunol., 28(4-5):489-98 (1991).
Padlan, Anatomy of the antibody molecule, Mol. Immunol., 31(3):169-217 (1994).
Pastan et al., Immunotoxin therapy of cancer, Nat. Rev. Cancer, 6(7):559-65 (2006).
Pastan et al., Immunotoxins. *Cell*, 47: 641-8 (1986).
Patti et al., Severe hypoglycaemia post-gastric bypass requiring partial pancreatectomy: evidence for inappropriate insulin secretion and pancreatic islet hyperplasia, Diabetologia, 48(11):2236-40 (2005).
Peyser et al., The artificial pancreas: current status and future prospects in the management of diabetes, Ann. N Y Acad. Sci., 1311:102-23 (2014).
Poljak, Production and structure of diabodies, Structure, 2(12):1121-3 (1994).
Presta et al., Engineering therapeutic antibodies for improved function, Biochem. Soc. Trans., 30(4):487-90 (2002).
Prigent et al., Identification of epitopes on the human insulin receptor reacting with rabbit polyclonal antisera and mouse monoclonal antibodies, J. Biol. Chem., 265:9970-7 (1990).
Raju, Terminal sugars of Fc glycans influence antibody effector functions of IgGs, Curr. Opin. Immunol., 20(4):471-8 (2008).
Reichman et al., Single domain antibodies: comparison of camel VH and camelised VH domains, J. Immunol. Methods, 231:25-38 (1999).
Riechmann et al., Reshaping human antibodies for therapy, Nature, 332(6162):323-7 (1988).
Roth et al., Monoclonal antibodies to the human insulin receptor block insulin binding and inhibit insulin action, Proc. Natl. Acad. Sci. USA, 79(23):7312-6 (1982).
Rothman et al., Antibody-dependent cytotoxicity mediated by natural killer cells is enhanced by castanospermine-induced alterations of IgG glycosylation, Mol. Immunol., 26(12):1113-23 (1989).
Safdari et al., Antibody humanization methods—a review and update, Biotech. Gen. Eng. Rev., 29:175-86 (2013).
Sanger et al., DNA sequencing with chain-terminating inhibitors, Proc. Natl. Acad. Sci. USA, 74(12):5463-7 (1977).

(56) References Cited

OTHER PUBLICATIONS

Sarmay et al., Mapping and comparison of the interaction sites on the Fc region of IgG responsible for triggering antibody dependent cellular cytotoxicity (ADCC) through different types of human Fc gamma receptor, Mol. Immunol., 29(5):633-9 (1992).
Schmidt et al., A bivalent single-chain antibody-toxin specific for ErbB-2 and the EGF receptor, Int. J. Cancer, 65(4):538-46 (1996).
Schoonjans et al., Fab chains as an efficient heterodimeration scaffold for the production of recombinant bispecific and trispecific antibody derivatives. J. Immunol. 165: 7050-7 (2000).
Schwimmer et al., Discovery of diverse and functional antibodies from large human repertoire antibody libraries, J. Immunol. Methods, 391(1-2):60-71 (2013).
Sergeeva et al., Display technologies: application for the discovery of drug and gene delivery agents, Adv. Drug Deliv. Rev., 58(15):1622-54 (2006).
Service et al., Hyperinsulinemic hypoglycemia with nesidioblastosis after gastric-bypass surgery, N. Engl. J. Med., 353(3):249-54 (2005).
Service, Classification of hypoglycemic disorders, Endocrinol. Metab. Clin. North Am., 28:501-17 (1999).
Shields et al., High resolution mapping of the binding site on human IgG1 for Fc gamma RI, Fc gamma RII, Fc gamma RIII, and FcRn and design of IgG1 variants with improved binding to the Fc gamma R, J. Biol. Chem., 276(9):6591-604 (2001).
Shields et al., Lack of fucose on human IgG1 N-linked oligosaccharide improves binding to human Fcgamma RIII and antibody-dependent cellular toxicity, J. Biol. Chem., 277(30):26733-40 (2002).
Shih et al., A fluorouridine-anti-CEA immunoconjugate is therapeutically effective in a human colonic cancer xenograft model, Int. J. Cancer, 46(6):1101-6 (1990).
Shinkawa et al., The absence of fucose but not the presence of galactose or bisecting N-acetylglucosamine of human IgG1 complex-type oligosaccharides shows the critical role of enhancing antibody-dependent cellular cytotoxicity, J. Biol. Chem., 278(5):3466-73 (2003).
Shopes, A genetically engineered human IgG mutant with enhanced cytolytic activity, J. Immunol., 148(9):2918-22 (1992).
Singh et al., Hypoglycemia after gastric bypass surgery, Diabetes Spectrum, 25:217-21 (2012).
Skerra et al., Assembly of a functional immunoglobulin Fv fragment in Escherichia coli. Science. 240: 1038-41 (1988).
Smaglo et al., The development of immunoconjugates for targeted cancer therapy, Nat. Rev. Clin. Oncol., 11(11):637-48 (2014).
Soos et al., Monoclonal antibodies reacting with multiple epitopes on the human insulin receptor, Biochem. J., 235(1):199-208 (1986).
Soos et al., Monoclonal antibodies reacting with multiple epitopes on the human insulin receptor, Biochem. J., 235:199-208 (1986).
Spasov et al., Study of antidiabetic activity of a new ultralow-dose antibody preparation on the model of streptozotocin diabetes in rats, Bull. Exp. Biol. Med., 144(1):46-8 (2007).
Steele-Perkins et al., Insulin-mimetic anti-insulin receptor monoclonal antibodies stimulate receptor kinase activity in intact cells, J. Biol. Chem., 265:9458-63 (1990).
Sternberger et al., The unlabeled antibody enzyme method of immunohistochemistry: preparation and properties of soluble antigen-antibody complex (horseradish peroxidase-antihorseradish peroxidase) and its use in identification of spirochetes, J. Histochem. Cytochem., 18(5):315-33 (1970).
Stevenson et al., A chimeric antibody with dual Fc regions (bisFabFc) prepared by manipulations at the IgG hinge, Anticancer Drug Des., 3(4):219-30 (1989).
Streilein et al. (eds.), Advances in gene technology: the molecular biology of immune diseases and the immune response. ICSU Short Reports. 10: 105 (1990).
Studnicka et al., Human-engineered monoclonal antibodies retain full specific binding activity by preserving non-CDR complementarity-modulating residues, Protein Eng., 7(6):805-14 (1994).
Taylor et al., Insulin-like and insulin-inhibitory effects of monoclonal antibodies for different epitopes on the human insulin receptor, Biochem. J., 242(1):123-9 (1987).
Taylor et al., Insulin-like and insulin-inhibitory effects of monoclonal antibodies for different epitopes on the human insulin receptor, Biochem. J., 242:123-9 (1987).
Thompson et al., An anti-CD3 single-chain immunotoxin with a truncated diphtheria toxin avoids inhibition by pre-existing antibodies in human blood, J. Biol. Chem., 270(47):28037-41 (1995).
Umana et al., Engineered glycoforms of an antineuroblastoma IgG1 with optimized antibody-dependent cellular cytotoxic activity, Nat. Biotechnol., 17(2):176-80 (1999).
Urlaub et al., Isolation of Chinese hamster cell mutants deficient in dihydrofolate reductase activity. Proc. Natl. Acad. Sci. USA. 77: 4216-20 (1980).
Vallera et al., Anti-graft-versus-host disease effect of DT390-anti-CD3sFv, a single-chain Fv fusion immunotoxin specifically targeting the CD3 epsilon moiety of the T-cell receptor, Blood, 88(6):2342-53 (1996).
Verhoeyen et al., Reshaping human antibodies: grafting an antilysozyme activity, Science, 239:1534-6 (1988).
Wada et al., New twist on neuronal insulin receptor signaling in health, disease, and therapeutics, J. Pharmacol. Sci., 99(2):128-43 (2005).
Wang et al., Abstracts of the 209th ACS National Meeting, Anaheim, Calif., Apr. 2-6, 1995, Part 1, BIOT005.
Ward et al., Binding activities of a repertoire of single immunoglobulin variable domains secreted from Escherichia coli, Nature, 341(6242):544-6 (1989).
Ward et al., Ligand-induced activation of the insulin receptor: a multi-step process involving structural changes in both the ligand and the receptor, Bioessays, 31(4):422-34 (2009).
Ward et al., Structural insights into ligand-induced activation of the insulin receptor, Acta Physiol. (Oxf.), 192(1):3-9 (2008).
Weinstein et al., Insulin analogues display IGF-I-like mitogenic and anti-apoptotic activities in cultured cancer cells, Diabetes Metab. Res. Rev., 25(1):41-9 (2009).
Wels et al., EGF receptor and p185erbB-2-specific single-chain antibody toxins differ in their cell-killing activity on tumor cells expressing both receptor proteins, Int. J. Cancer, 60(1)1 37-44 (1995).
Wheeler et al. Intrabody-based strategies for inhibition of vascular endothelial growth factor receptor-2: effects on apoptosis, cell growth, and angiogenesis. FASEB. J. 17: 1733-5 (2003).
Willems et al., Optimizing expression and purification from cell culture medium of trispecific recombinant antibody derivatives, J. Chromatogr. B Analyt. Technol. Biomed. Life Sci., 786(1-2):161-76 (2003).
Winter et al., Making antibodies by phage display technology, Annu. Rev. Immunol., 12:433-55 (1994).
Wittrup, Protein engineering by cell-surface display, Curr. Opin. Biotechnol., 12(4):395-9 (2001).
Wolff et al., Monoclonal antibody homodimers: enhanced antitumor activity in nude mice, Cancer Res., 53(11):2560-5 (1993).
Wu et al., Humanization of a murine monoclonal antibody by simultaneous optimization of framework and CDR residues. J. Mol. Biol., 294: 151-62 (1999).
Yamane-Ohnuki et al., Establishment of FUT8 knockout Chinese hamster ovary cells: an ideal host cell line for producing completely defucosylated antibodies with enhanced antibody-dependent cellular cytotoxicity, Biotechnol. Bioeng., 87(5):614-22 (2004).
Yang et al., A genetically engineered fusion protein M4/TNF with increased bifunctional activity refolded in the presence of protein disulfide isomerase, Hum. Antibodies Hybridomas, 6(4):129-36 (1995).
Yorifuji, Congenital hyperinsulinism: current status and future perspectives, Ann. Pediatr. Endocrinol. Metab., 19(2):57-68 (2014).
Yu et al., Peptide-antibody conjugates for tumour therapy: a MHC-class-II-restricted tetanus toxin peptide coupled to an anti-Ig light chain antibody can induce cytotoxic lysis of a human B-cell lymphoma by specific CD4 T cells, Int. J. Cancer, 56(2):244-8 (1994).
Bedinger et al., Differential pathway coupling of the activated insulin receptor drives signaling selectivity by XMetA, an allosteric partial agonist antibody, J. Pharmacol. Exp. Ther., 353(1):35-43 (2015).

(56) References Cited

OTHER PUBLICATIONS

Bhaskar et al., A fully human, allosteric monoclonal antibody that activates the insulin receptor and improves glycemic control, Diabetes, 61(5):1263-71 (2012).

Corbin et al., Improved glucose metabolism in vitro and in vivo by an allosteric monoclonal antibody that increases insulin receptor binding affinity, PLoS One, 9(2):e88684 (2014).

Corbin et al., Inhibition of insulin receptor function by a human, allosteric monoclonal antibody: a potential new approach for the treatment of hyperinsulinemic hypoglycemia, MAbs, 6(1):262-72 (2014).

International Application No. PCT/US2016/045917, International Search Report and Written Opinion, dated Apr. 28, 2017.

International Application No. PCT/US2016/045917, Invitation to Pay Additional Fees and, Where Applicable, Protest Fee, dated Jan. 9, 2017.

Strohl et al., Variable chain engineering—humanization and optimization approaches, pp. 111-30 IN: Therapeutic Antibody Engineering, a volume in Woodhead Publishing Series in Biomedicine (2012).

Figure 6

| | Sequence | SEQ ID |
|---|---|---|
| XPA.15.247 VH | EVQLVETGGGVVQPGRSLRLSCAASGFTFSSYAMHWVRQAP GKGLEWVAVISYDGSNKYYADSVKGRFTISRDNSKNTLYLQ MNSLRAEDTAVYYCARHEWGFGMDVWGQGTTVTVSS | 1 |
| XPA.15.247.2.018 VH | EVQLVETGGGVVQPGRSLRLSCAASGFTFSSYAMHWVRQAP GKGLEWVAVISYSGSNKYYADSVKGRFTISRDNSKNTLYLQ MNSLRAEDTAVYYCARHEWGFGFDYWGQGTTVTVSS | 2 |
| XPA.15.247 VL | DVVMTQSPLSLSVTLGQPASISCRSSLSLVYGDENTYLNWFQ QRPGQSPRRLLYKVSDRDSGVPDRFSGSGSGTDFTLKISRVE ADDVGVYYCMQGTHWPYTFGQGTKLEIKRTVAAPS | 3 |
| XPA.15.247.2.018 VL | DVVMTQSPLSLPVTLGQPASISCRSSQSLVYGDGNTYLNWFQ QRPGQSPRRLIYKVSNRDSGVPDRFSGSGSGTEFTLKISRVEA EDVGVYFCMQGTYWPGTFGGGTKLEIKRTVAAPS | 4 |
| XPA.15.247 VH CDR1 | GFTFSSYA | 5 |
| XPA.15.247 VH CDR2 | ISYDGSNK | 6 |
| XPA.15.247 VH CDR3 | ARHEWGFGMDV | 7 |
| XPA.15.247.2.018 VH CDR1 | GFTFSSYA | 8 |
| XPA.15.247.2.018 VH CDR2 | ISYSGSNK | 9 |
| XPA.15.247.2.018 VH CDR3 | ARHEWGFGFDY | 10 |
| XPA.15.247 VL CDR1 | LSLVYGDENTY | 11 |
| XPA.15.247 VL CDR2 | KVS | 12 |
| XPA.15.247 VL CDR3 | YTFGQGTKLEIK | 13 |
| XPA.15.247.2.018 VL CDR1 | QSLVYGDENTY | 14 |
| XPA.15.247.2.018 VL CDR2 | KVS | 15 |
| XPA.15.247.2.018 VL CDR3 | MQGTYWP | 16 |
| XPA.15.247.014 VL | DVVMTQSPLSLPVTLGQPASISCRSSQSLVYGDGNTYLNWFQ QRPGQSPRRLIYKVSKRDSGVPDRFSGSGSGTDFTLKISRVEA EDVGVYYCMQGTYWPMTFGGGTKLEIKR | 17 |
| XPA.15.247.011 VL | DVVMTQSPLSLPVTLGQPASISCRSSHSLVYGDGNTYLNWFH QRPGQSPRRLIYKVSNRDSGVPDRFAGSGSGTDFTLKISRVEA DDFGVFYCMQGTHWPYTFGQGTKLEIKR | 18 |
| XPA.15.247.019 VL | DVVMTQSPLSLPVTLGQPASISCRSSESLVYGDENTYLNWFQ QRPGQSPRRLIYKVSNRDSGVPSRFSGSGSGTDFTLKISRVEA EDVGVYYCMQGTHWPYTFGQGTKLEIKR | 19 |
| XPA.15.247.014 VL CDR1 | QSLVYGDGNTY | 20 |
| XPA.15.247.014 VL CDR2 | KVS | 21 |
| XPA.15.247.014 VL CDR3 | MQGTYWPMT | 22 |
| XPA.15.247.011 VL | HSLVYGDGNTY | 23 |

| CDR1 | | |
|---|---|---|
| XPA.15.247.011 VL CDR2 | KVS | 24 |
| XPA.15.247.011 VL CDR3 | MQGTHWPYT | 25 |
| XPA.15.247.019 VL CDR1 | ESLVYGDENTY | 26 |
| XPA.15.247.019 VL CDR2 | KVS | 27 |
| XPA.15.247.019 VL CDR3 | MQGTHWPYT | 28 |

Figure 6 (continued)

Early timepoints

Full timecourse

Figure 10A-Early timepoints
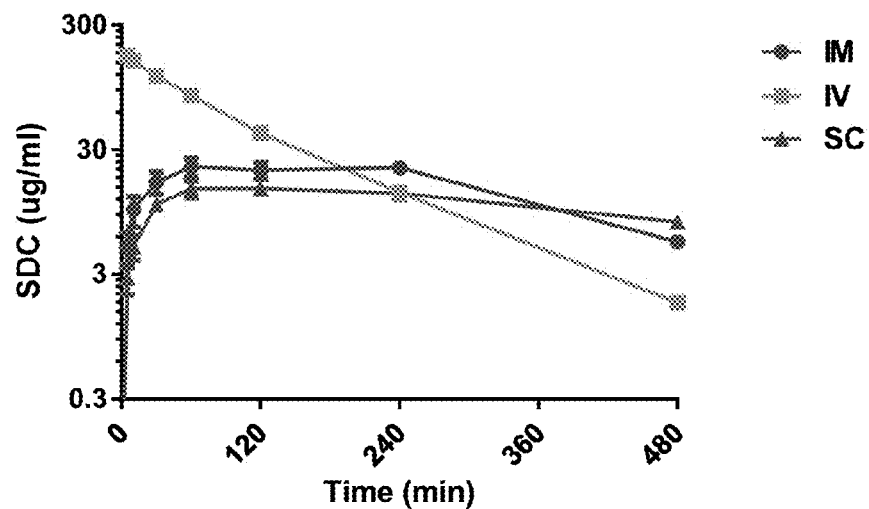
Figure 10B-Full timecourse
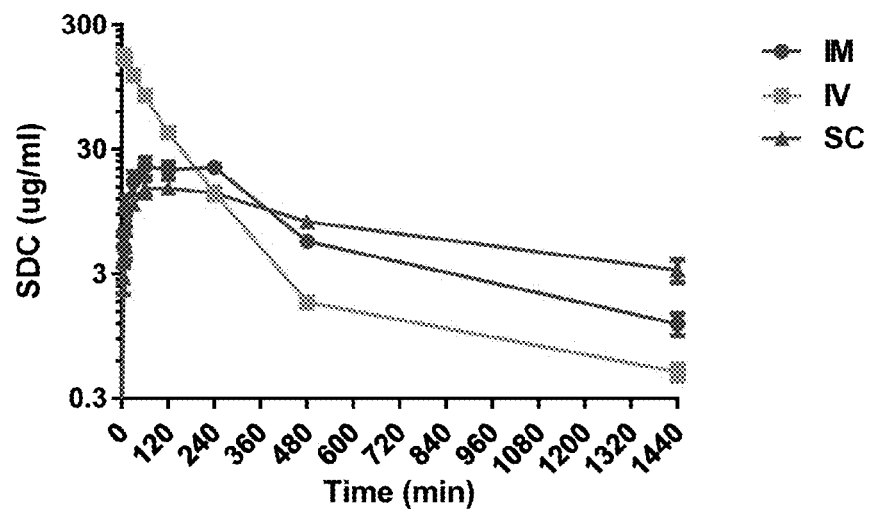

|    | n | Cmax (ug/ml) | Tmax (h) | AUC (ug*h/ml) | t1/2 (h) | F% |
|----|---|--------------|----------|---------------|----------|-----|
| IV | 4 | 172.8 | 0.1 | 280.3 | 3.3 | n/a |
| IM | 4 | 24.1 | 2 | 185.3 | 5.6 | 66.9 |
| SC | 3 | 15.9 | 1.7 | 183.3 | 10.5 | 65.5 |

Figure 19

| Name | SEQ ID NO | H-cdr1 | SEQ ID NO | H-cdr2 | SEQ ID NO | H-cdr3 | SEQ ID NO | Affinity: $K_D$ (M) | Fold $K_D$ Improvement |
|---|---|---|---|---|---|---|---|---|---|
| 247.2.018 Fab | 2 | GFTFSSYA | 5 | ISYSGSNK | 6 | ARHEWGFGFDY | 7 | 9.7 nM | 1.0 |
| RHF.15.05896.004 | 29 | GFRFSSYA | 50 | ISYSGSNK | 51 | ARHEWGFGFDE | 52 | 1.6 nM | 6.1 |
| RHF.15.05896.006 | 30 | GFKFSSYA | 53 | ISYSGDNK | 54 | ARHEWGFGFDR | 55 | 1.9 nM | 5.2 |
| RHF.15.05896.012 | 31 | GFTFSSWA | 56 | ISYSGENK | 57 | ARHEWGFPFDY | 58 | 460 pM | 21.0 |
| RHF.15.05896.015 | 32 | GFKFSSYA | 59 | ISYSGRNK | 60 | ARHEWGFGQDY | 61 | 3.0 nM | 3.3 |
| RHF.15.05896.020 | 33 | GFRFSSYA | 62 | ISWSGSNK | 63 | ARHEWGFGFDE | 64 | 1.5 nM | 6.4 |
| RHF.15.05896.022 | 34 | GFTFSSWA | 65 | ISYSGSNT | 66 | ARHEWGFPFDY | 67 | 680 pM | 14.2 |
| RHF.15.05896.028 | 35 | GFKFSSYA | 68 | ISGSGSNK | 69 | ARHEWGLGFDY | 70 | 1.4 nM | 7.0 |
| RHF.15.05896.032 | 36 | GFKFSSYA | 71 | ISYSGENK | 72 | ARHEWGFGFDE | 73 | 1.1 nM | 8.6 |
| RHF.15.05896.036 | 37 | GFKFSSYA | 74 | ISYSGGNK | 75 | ARHEWGFGFDL | 76 | 1.8 nM | 5.4 |
| RHF.15.05896.040 | 38 | GFKFSSYA | 77 | ISNSGSNK | 78 | ARHEWGFGFDW | 79 | 1.8 nM | 5.5 |
| RHF.15.05896.044 | 39 | GFKFSSYA | 80 | ISNSGSNK | 81 | ARHEWGFGFDK | 82 | 1.3 nM | 7.4 |
| RHF.15.05896.048 | 40 | GFTFRSYA | 83 | ISYSGSVK | 84 | ARHEWGFGFDE | 85 | 1.3 nM | 7.5 |
| RHF.15.05896.052 | 41 | GFKFSSYA | 86 | ISYGGSNK | 87 | ARHEWGFGFDE | 88 | 1.1 nM | 9.0 |
| RHF.15.05896.056 | 42 | GFKFSSYA | 89 | ISYGGSNK | 90 | ARHEWGFGFDE | 91 | 1.4 nM | 6.9 |
| RHF.15.05896.059 | 43 | GFRFSSYA | 92 | ISYSGSVK | 93 | ARHEWGFGFDR | 94 | 1.3 nM | 7.4 |
| RHF.15.05896.064 | 44 | GFKFSSYA | 95 | ISYSGSHK | 96 | ARHEWGFGQDY | 97 | 2.6 nM | 3.7 |
| RHF.15.05896.068 | 45 | GFKFSSYA | 98 | ISYSGGNK | 99 | ARHEWGFGYDY | 100 | 1.2 nM | 8.3 |
| RHF.15.05896.072 | 46 | GFRFSSYA | 101 | ISYSGGNK | 102 | ARHEWGFGYDY | 103 | 1.4 nM | 6.8 |
| RHF.15.05896.075 | 47 | GFKFSSYA | 104 | ISYSGSNK | 105 | ARHEWGFGYDY | 106 | 1.4 nM | 7.0 |
| RHF.15.05896.079 | 48 | GFKFSSYA | 107 | ISWSGSNK | 108 | ARHEWGFGYDY | 109 | 1.2 nM | 8.1 |
| RHF.15.05896.084 | 49 | GFRFSSYA | 110 | ISWSGSNK | 111 | ARHEWGFGFDK | 112 | 2.2 nM | 4.4 |

Figure 19 (cont'd)

| Name | $k_a$ (1/Ms) | $k_d$ (1/s) | Potency EC50 value [nM] | CHO Human INSR | CHO Human INSR | CHO Cyno INSR | CHO Rat INSR | CHO Cyno INSR | CHO Rat INSR |
|---|---|---|---|---|---|---|---|---|---|
| 247.2.018 Fab | 1.1E+05 | 1.1E-03 | 1.309 | 2.204 | 1.634 | 2.615 | 1.279 | 2.615 | 1.279 |
| RHF.15.05896.004 | 1.3E+05 | 2.1E-04 | | 2.426 | | | | | |
| RHF.15.05896.006 | 1.3E+05 | 2.4E-04 | | 2.946 | | | | | |
| RHF.15.05896.012 | 7.2E+04 | 3.3E-05 | 2.200 | 4.525 | | | | | |
| RHF.15.05896.015 | 8.4E+04 | 2.5E-04 | | 4.350 | | | | | |
| RHF.15.05896.020 | 1.1E+05 | 1.7E-04 | | 1.955 | 0.838 | 0.9108 | 0.661 | 0.9108 | 0.6605 |
| RHF.15.05896.022 | 7.3E+04 | 5.0E-05 | | 3.724 | | | | | |
| RHF.15.05896.028 | 1.1E+05 | 1.5E-04 | | 2.014 | | | | | |
| RHF.15.05896.032 | 9.1E+04 | 1.0E-04 | | 3.098 | | | | | |
| RHF.15.05896.036 | 1.2E+05 | 2.2E-04 | | 3.036 | | | | | |
| RHF.15.05896.040 | 9.2E+04 | 1.6E-04 | | 2.923 | | | | | |
| RHF.15.05896.044 | 1.3E+05 | 1.7E-04 | | 2.518 | | | | | |
| RHF.15.05896.048 | 1.6E+05 | 2.1E-04 | | 2.075 | | | | | |
| RHF.15.05896.052 | 1.3E+05 | 1.3E-04 | | 1.853 | | | | | |
| RHF.15.05896.056 | 1.2E+05 | 1.7E-04 | | 2.264 | | | | | |
| RHF.15.05896.059 | 1.9E+05 | 2.5E-04 | | 2.509 | | | | | |
| RHF.15.05896.064 | 6.0E+04 | 1.6E-04 | | 6.298 | | | | | |
| RHF.15.05896.068 | 3.2E+05 | 3.8E-04 | | 1.249 | 0.762 | 0.8538 | 0.533 | 0.8538 | 0.5328 |
| RHF.15.05896.072 | 3.8E+05 | 5.4E-04 | 1.084 | 1.052 | 0.609 | 0.7718 | 1.039 | 0.7718 | 1.039 |
| RHF.15.05896.075 | 3.2E+05 | 4.5E-04 | 1.160 | 1.065 | 0.791 | 0.7282 | 0.621 | 0.7282 | 0.6212 |
| RHF.15.05896.079 | 2.9E+05 | 3.5E-04 | | 1.264 | | | | | |
| RHF.15.05896.084 | 1.7E+05 | 3.8E-04 | 1.138 | 1.865 | 0.692 | 0.7284 | 0.799 | 0.7284 | 0.7986 |

Figure 20

H-CDR1

| Position | Amino Acid | A | C | D | E | F | G | H | I | K | L | M | N | P | Q | R | S | T | V | W | X | Y | % Mutated |
|---|---|---|---|---|---|---|---|---|---|---|---|---|---|---|---|---|---|---|---|---|---|---|---|
| 26 | G | 0 | 0 | 0 | 0 | 0 | 271 | 0 | 0 | 0 | 0 | 0 | 0 | 0 | 0 | 0 | 0 | 0 | 0 | 0 | 0 | 0 | 0.00% |
| 27 | F | 0 | 0 | 0 | 0 | 268 | 0 | 0 | 0 | 0 | 0 | 0 | 0 | 0 | 0 | 0 | 0 | 0 | 0 | 2 | 0 | 1 | 1.11% |
| 28 | T | 2 | 0 | 0 | 1 | 1 | 9 | 1 | 0 | 122 | 1 | 0 | 2 | 4 | 8 | 59 | 1 | 61 | 0 | 0 | 0 | 0 | 77.49% |
| 29 | F | 0 | 0 | 0 | 0 | 270 | 0 | 0 | 0 | 0 | 0 | 0 | 0 | 0 | 0 | 0 | 0 | 0 | 0 | 0 | 0 | 1 | 0.37% |
| 30 | S | 0 | 0 | 1 | 1 | 0 | 5 | 1 | 0 | 2 | 0 | 0 | 2 | 1 | 1 | 5 | 252 | 0 | 0 | 0 | 0 | 0 | 7.01% |
| 31 | S | 1 | 0 | 0 | 0 | 0 | 0 | 0 | 0 | 6 | 0 | 0 | 0 | 0 | 0 | 0 | 264 | 0 | 0 | 0 | 0 | 0 | 2.58% |
| 32 | Y | 0 | 0 | 0 | 0 | 0 | 0 | 0 | 0 | 0 | 0 | 0 | 0 | 0 | 0 | 0 | 0 | 0 | 0 | 16 | 0 | 255 | 5.90% |
| 33 | A | 271 | 0 | 0 | 0 | 0 | 0 | 0 | 0 | 0 | 0 | 0 | 0 | 0 | 0 | 0 | 0 | 0 | 0 | 0 | 0 | 0 | 0.00% |

H-CDR2

| Position | Amino Acid | A | C | D | E | F | G | H | I | K | L | M | N | P | Q | R | S | T | V | W | X | Y | % Mutated |
|---|---|---|---|---|---|---|---|---|---|---|---|---|---|---|---|---|---|---|---|---|---|---|---|
| 51 | I | 0 | 0 | 0 | 0 | 0 | 0 | 0 | 269 | 0 | 0 | 0 | 0 | 0 | 0 | 0 | 0 | 0 | 2 | 0 | 0 | 0 | 0.74% |
| 52 | S | 0 | 0 | 0 | 0 | 0 | 0 | 0 | 0 | 0 | 0 | 0 | 0 | 0 | 0 | 0 | 271 | 0 | 0 | 0 | 0 | 0 | 0.00% |
| 53 | Y | 0 | 0 | 14 | 17 | 0 | 6 | 1 | 0 | 1 | 0 | 0 | 6 | 0 | 0 | 0 | 3 | 3 | 4 | 30 | 0 | 237 | 12.55% |
| 54 | S | 0 | 0 | 9 | 0 | 1 | 6 | 0 | 0 | 1 | 0 | 0 | 4 | 0 | 5 | 0 | 222 | 0 | 0 | 0 | 0 | 0 | 18.08% |
| 55 | G | 0 | 0 | 0 | 0 | 0 | 271 | 0 | 1 | 0 | 1 | 0 | 0 | 0 | 0 | 0 | 0 | 0 | 0 | 0 | 0 | 0 | 0.00% |
| 56 | S | 2 | 0 | 9 | 18 | 1 | 20 | 3 | 1 | 1 | 1 | 0 | 4 | 0 | 4 | 3 | 202 | 1 | 0 | 3 | 0 | 0 | 25.46% |
| 57 | N | 2 | 0 | 3 | 7 | 0 | 0 | 3 | 0 | 0 | 0 | 0 | 244 | 2 | 1 | 0 | 1 | 1 | 8 | 0 | 0 | 0 | 9.96% |
| 58 | K | 3 | 0 | 3 | 13 | 0 | 6 | 3 | 0 | 214 | 1 | 0 | 1 | 0 | 3 | 3 | 2 | 2 | 3 | 2 | 0 | 0 | 21.03% |

H-CDR3

| Position | Amino Acid | A | C | D | E | F | G | H | I | K | L | M | N | P | Q | R | S | T | V | W | X | Y | % Mutated |
|---|---|---|---|---|---|---|---|---|---|---|---|---|---|---|---|---|---|---|---|---|---|---|---|
| 97 | A | 269 | 0 | 0 | 0 | 0 | 1 | 0 | 0 | 0 | 0 | 0 | 0 | 0 | 0 | 0 | 1 | 0 | 0 | 0 | 0 | 0 | 0.74% |
| 98 | R | 0 | 0 | 0 | 0 | 0 | 0 | 0 | 0 | 0 | 0 | 0 | 0 | 0 | 0 | 271 | 0 | 0 | 0 | 0 | 0 | 0 | 0.00% |
| 99 | H | 0 | 0 | 0 | 0 | 0 | 0 | 271 | 0 | 0 | 0 | 0 | 0 | 0 | 0 | 0 | 0 | 0 | 0 | 0 | 0 | 0 | 0.00% |
| 100 | E | 0 | 0 | 0 | 271 | 0 | 0 | 0 | 0 | 0 | 0 | 0 | 0 | 0 | 0 | 0 | 0 | 0 | 0 | 0 | 0 | 0 | 0.00% |
| 101 | W | 0 | 0 | 0 | 0 | 0 | 0 | 0 | 0 | 0 | 0 | 0 | 0 | 0 | 0 | 0 | 0 | 0 | 0 | 271 | 0 | 0 | 0.00% |
| 102 | G | 0 | 0 | 0 | 0 | 0 | 271 | 0 | 0 | 0 | 0 | 0 | 0 | 0 | 0 | 0 | 0 | 0 | 0 | 0 | 0 | 0 | 0.00% |
| 103 | F | 0 | 0 | 3 | 0 | 244 | 2 | 6 | 0 | 0 | 5 | 0 | 7 | 0 | 1 | 0 | 0 | 0 | 0 | 0 | 0 | 3 | 9.96% |
| 104 | G | 0 | 0 | 0 | 0 | 0 | 266 | 0 | 0 | 0 | 0 | 0 | 0 | 5 | 0 | 0 | 0 | 0 | 0 | 0 | 0 | 0 | 1.85% |
| 105 | F | 0 | 0 | 0 | 0 | 194 | 3 | 0 | 0 | 0 | 0 | 0 | 0 | 0 | 9 | 0 | 0 | 0 | 0 | 24 | 0 | 40 | 28.41% |
| 106 | D | 0 | 0 | 271 | 0 | 0 | 0 | 0 | 0 | 0 | 0 | 0 | 0 | 0 | 0 | 0 | 0 | 0 | 0 | 0 | 0 | 0 | 0.00% |
| 107 | Y | 2 | 0 | 0 | 69 | 0 | 2 | 2 | 1 | 12 | 7 | 0 | 0 | 0 | 17 | 11 | 5 | 2 | 1 | 5 | 0 | 130 | 52.03% |

Selected clones with Off rate improvement based on PPE screen. Not sequence unique.
248/271 sequence unique : # ANTIBODY FRAGMENTS AGAINST THE INSULIN RECEPTOR AND USES THEREOF TO TREAT HYPOGLYCEMIA This application claims the priority benefit of U.S. Provisional Patent Application 62/202,143, filed Aug. 6, 2015, and U.S. Provisional Patent Application 62/280,675, filed Jan. 19, 2016, herein incorporated by reference in their entirety.

FIELD OF THE INVENTION

The present disclosure relates, in general, to the use of a negative modulator antibody fragment specific for the insulin receptor that modulates the binding of insulin to the insulin receptor in the treatment and prevention of hypoglycemia, e.g., due to endogenous or exogenous hyperinsulinemia, insulin overdose, drug-induced hypoglycemia, insulin-induced hypoglycemia, hypoglycemia that occurs after eating in patients who have undergone bariatric, or gastric bypass surgery, and disease hypoglycemic states characterized by abnormal glucose levels, as well as complications and conditions related to hyperinsulinemia.

BACKGROUND OF THE INVENTION

The present disclosure relates to novel modulators of the insulin-insulin receptor signaling complex in the treatment or prevention of hypoglycemic disease states and conditions characterized by abnormal production and/or utilization of insulin, insulin analogues, or insulin mimetic s.

Insulin is the major hormone for lowering blood glucose levels. The first step in insulin action is the binding of the hormone to the insulin receptor (INSR), an integral membrane glycoprotein, also designated as CD220 or HHFS. When insulin binds to the INSR, the receptor is activated by tyrosine autophosphorylation and the INSR tyrosine kinase phosphorylates various effector molecules, including the insulin receptor substrate-1 (IRS-1), leading to hormone action (Ullrich et al, *Nature* 313: 756-761, 1985; Goldfine et al, *Endocrine Reviews* 8: 235-255, 1987; *White and Kahn, Journal Biol. Chem.* 269: 1-4, 1994). IRS-1 binding and phosphorylation eventually leads to an increase in the high affinity glucose transporter (Glut4) molecules on the outer membrane of insulin-responsive tissues, including muscle cells and adipose tissue, and to an increase, therefore, in the uptake of glucose from blood into these tissues. Glut4 is transported from cellular vesicles to the cell surface, where it then can mediate the transport of glucose into the cell and a decrease in blood glucose levels.

Abnormal increases in insulin secretion can lead to profound hypoglycemia or low blood sugar, a state that may result in significant morbidities including epilepsy and cerebral damage. Drug-induced hypoglycemia can result from administration of sulfonylurea drugs or from an overdose of insulin. A number of rare medical conditions feature non-drug-induced, endogenous hyperinsulinemic hypoglycemia, i.e., low blood glucose caused by the body's excessive production of insulin. These conditions include congenital hyperinsulinism, insulinoma, and hyperinsulinemic hypoglycemia following gastric bypass surgery.

Iatrogenic hypoglycemia describes the condition and effects of low blood glucose caused by administration of either excessive insulin or its analogues, or medications that stimulate endogenous insulin secretion. Iatrogenic hypoglycemia, fundamentally but not exclusively the result of treatment with an insulin secretagogue or insulin, is a major limiting factor in the glycemic management of diabetes. Iatrogenic hypoglycemia causes recurrent morbidity in most people with T1DM and many with advanced T2DM, and is sometimes fatal. Recurrent episodes of hypoglycemia impair the body's defenses against subsequent falling plasma glucose concentrations and thus cause a vicious cycle of recurrent hypoglycemia.

Hypoglycemia results in a variety of symptoms including; lack of coordination, confusion, loss of consciousness, seizures, and even death.

Most episodes of mild hypoglycemia are effectively self-treated by ingestion of glucose tablets or other carbohydrate containing drinks or snacks. More severe symptomatic hypoglycemia also can be treated with oral carbohydrate ingestion. However, when the hypoglycemic patient cannot take oral glucose supplements, because of confusion, unconsciousness or other reasons, parenteral therapy is required. As a non-hospital rescue procedure, injection of the hyperglycemic hormone, glucagon, is sometimes employed, either subcutaneously or intramuscularly by the patient himself or an associate of the patient who has been trained to recognize and treat severe hypoglycemia. In a medical setting, intravenous glucose is the standard parenteral therapy.

Congenital hyperinsulinism (CHI) comprises a group of genetic disorders that are characterized by recurrent episodes of hyperinsulinemic hypoglycemias due to unregulated secretion of insulin by the pancreatic β-cells (Arnoux J., et al. *Orphanet Journal of Rare Diseases* 6:63 (2011); Yorifuji T., *Ann Pediatr Endocrinol Metab* 19:57-68 (2014). CHI is the most common cause of hyperinsulinemic hypoglycemia in neonatal, infant and childhood periods and is usually diagnosed within the first two years of life. Histopathologically, CHI can present in either diffuse or focal forms. In the diffuse form, all pancreatic β-cells are affected, whereas in focal forms, lesions of abnormal β-cells are (usually) restricted to small areas of the pancreas. The most common known causes of CHI are loss-of-function mutations in the genes encoding SUR1 and Kir6.2, subunits of the ATP-sensitive potassium channel (KATP channel), involved in the secretion of insulin in pancreatic β-cells.

Post-prandial hypoglycemia (PPH) has recently been observed as a side effect or complication of gastric bypass surgery (Singh et al., *Diabetes Spectrum* 25: 217-221, 2012; Patti et al., *Diabetologia* 48:2236-2240, 2005; Service et al. *N Engl J Med* 353:249-254, 2005), including after the common procedure of Roux-en-Y gastric bypass (RYGB). A commonly observed side effect of gastric bypass surgery is "dumping," which is a consequence of the ingestion of simple sugars and rapid emptying of food into the small intestine. This is often characterized by vasomotor symptoms (e.g., flushing, tachycardia), abdominal pain, and diarrhea (Singh et al., *Diabetes Spectrum* 25: 217-221, 2012; Mathews et al., *Surgery* 48:185-194, 1960). Late dumping can occur up to a few hours after eating and results from the insulin response to hyperglycemia resulting from rapid absorption of simple sugars from the proximal small intestine. In contrast to dumping, which is noted soon after surgery and improves with time, hyperinsulinemic hypoglycemia presents several months to years (usually around 1 year, up to 3 years) after gastric bypass surgery. This syndrome is differentiated from dumping by onset of severe postprandial neuroglycopenia, which is typically absent in dumping, as well as pancreatic nesidioblastosis (islet cell enlargement, β-cells budding from ductal epithelium, and islets in apposition to ducts). Unlike with dumping, nutrition modification does not alleviate the symptoms of post-prandial hypoglycemia (PPH).

SUMMARY OF THE INVENTION

The present disclosure relates to the use of negative modulator antibody fragments against the insulin receptor to treat patients that have hypoglycemia. Such modulators may, for example, be used to treat a mammalian subject suffering from hypoglycemia due to endogenous or exogenous hyperinsulinemia, e.g., resulting from insulin overdose, and disease hypoglycemic states characterized by abnormal glucose levels. Such modulators could also be used to prevent the occurrence of the hypoglycemia in an at risk subject such as patients having Type 1 (e.g., brittle) or Type 2 diabetic patients, that have undergone bariatric surgery, or that have inherited metabolic and insulin sensitivity disorders.

In various embodiments, the invention provides an antibody or fragment thereof comprising three heavy chain CDRs having the amino acid sequence set out in SEQ ID NOs: 5-7, 8-10 and 50-112 and three light chain CDRs have the amino acid sequences set out in SEQ ID NOs: 14-16 or SEQ ID NOs: 20-28 wherein the antibody or fragment thereof binds to i) insulin receptor or (ii) a complex comprising insulin and insulin receptor, or both (i) and (ii). For example, in one embodiment, the invention provides an antibody or fragment thereof wherein the heavy chain variable region amino acid sequence is set out in SEQ ID NOs: 1, 2 or 29-49, and the light chain variable region amino acid sequence is set out in SEQ ID NOs: 4 or 17-19.

In various embodiments, the invention provides an antibody or fragment thereof comprising three heavy chain CDRs having the amino acid sequence set out in SEQ ID NOs: 5-7, 8-10, 50-52, 53-55, 56-58, 59-61, 62-64, 65-67, 68-70, 71-73, 74-76, 77-79, 80-82, 83-85, 86-88, 89-91, 92-94, 95-97, 98-100, 101-103, 104-106, 107-109, or 110-112 and three light chain CDRs have the amino acid sequences set out in SEQ ID NOs: 11-13, 14-16, or SEQ ID NOs: 20-28 wherein the antibody or fragment thereof binds to (i) insulin receptor or (ii) a complex comprising insulin and insulin receptor, or both (i) and (ii). For example, in some embodiments, the invention provides an antibody or fragment thereof wherein the heavy chain variable region amino acid sequence is set out in SEQ ID NO: 1, 2 or 29-49 and the light chain variable region amino acid sequence is set out in SEQ ID NO: 3, 4 or 17-19.

In various embodiments, the disclosure provides an antibody or fragment thereof comprising three heavy chain CDRs having the amino acid sequence set out in SEQ ID NOs: 8-10 and three light chain CDRs have the amino acid sequences set out in SEQ ID NOs: 14-16, wherein the antibody or fragment thereof binds to i) insulin receptor or (ii) a complex comprising insulin and insulin receptor, or both (i) and (ii). In various embodiments, the heavy chain variable region amino acid sequence is set out in SEQ ID NO: 2 and the light chain variable region amino acid sequence is set out in SEQ ID NO: 4.

Also provided is an antibody fragment comprising three heavy chain CDRs having the amino acid sequences set out in SEQ ID NOs: 5-7 or 8-10 and three light chain CDRs having the amino acid sequences set out in SEQ ID NOs: 11-13 or 14-16, wherein the antibody fragment binds to i) insulin receptor or (ii) a complex comprising insulin and insulin receptor, or both (i) and (ii). In various embodiments, the heavy chain variable region amino acid sequence is set out in SEQ ID NO: 1 or 2 and the light chain variable region amino acid sequence is set out in SEQ ID NO: 3 or 4.

In various embodiments, the antibody or fragment thereof is a Fab fragment.

In various embodiments, the antibody or fragment binds to heparin to a lesser degree than other antibodies or fragments, including Fabs or Fab variants.

In various embodiments, the antibody or fragment thereof binds to (i) insulin receptor or (ii) a complex comprising insulin and insulin receptor, or both (i) and (ii), with an equilibrium dissociation constant $K_D$ of $10^{-5}$ M or less that is capable of weakening the binding affinity between insulin and insulin receptor by at least about 1.5-fold, optionally up to 1000-fold. In certain embodiments, the antibody is capable of weakening the binding affinity between said insulin and insulin receptor by about 2-fold to 500-fold. In various embodiments, the antibody increases the $EC_{50}$ of insulin signaling activity by about 2-fold to 1000-fold, optionally in a pAKT assay. Optionally, the binding affinity is any one of $K_A$, $K_D$, the ratio of on rate to off rate, or the ratio of off rate to on rate.

In various embodiments, the antibody or fragment thereof is a monoclonal antibody. In various embodiments, the antibody or fragment thereof is a human antibody.

In various embodiments, the antibody or fragment thereof is conjugated to a hydrophobic moiety.

In various embodiments, the antibody or fragment thereof is in a pharmaceutical composition.

In various embodiments, the disclosure contemplates a method of preparing a sterile pharmaceutical composition, comprising adding a sterile pharmaceutically acceptable diluent to an antibody or fragment thereof contemplated herein. Optionally, small amounts of a preservative such as a bactericidal or bacteriostatic agent are also included in the composition. Also contemplated is a sterile composition comprising an antibody or fragment thereof described herein and a sterile pharmaceutically acceptable diluent.

In various embodiments, the invention provides a method of treating or preventing hypoglycemia, comprising administering to a subject in need thereof an antibody or fragment thereof that is a negative modulator of insulin binding to the insulin receptor and/or insulin action at the insulin receptor in an amount effective to ameliorate or prevent hypoglycemia. Optionally, the hypoglycemia is selected from the group consisting of sulfonylurea-induced hypoglycemia, insulin-induced hypoglycemia, nocturnal hypoglycemia and hypoglycemia following post-bariatric surgery.

In various embodiments, the invention provides a method for treating or preventing nocturnal hypoglycemia comprising administering to a subject in need thereof an antibody or fragment thereof that is a negative modulator of insulin binding to the insulin receptor and/or insulin action at the insulin receptor in an amount effective to ameliorate or prevent nocturnal hypoglycemia.

In various embodiments, the invention provides a method comprising administering an antibody fragment that binds to (i) insulin receptor or (ii) a complex comprising insulin and insulin receptor, or both (i) and (ii), with an equilibrium dissociation constant $K_D$ of $10^{-5}$M or less that is capable of weakening the binding affinity between insulin and insulin receptor by at least about 1.5-fold, optionally up to 1000-fold. Optionally, the antibody fragment increases the $EC_{50}$ of insulin signaling activity by about 2-fold to 1000-fold, optionally in a pAKT assay In various embodiments, the invention provides a method comprising administering an antibody fragment comprising three heavy chain CDRs having the amino acid sequences set out in SEQ ID NOs: 5-7, 8-10, 50-52, 53-55, 56-58, 59-61, 62-64, 65-67, 68-70, 71-73, 74-76, 77-79, 80-82, 83-85, 86-88, 89-91, 92-94, 95-97, 98-100, 101-103, 104-106, 107-109, or 110-112 and three light chain CDRs have the amino acid sequences set out in SEQ ID NOs: 11-13, 14-16 or SEQ ID NOs: 20-28, or wherein the heavy chain variable region amino acid sequence is set out in SEQ ID NO: 1, 2 or 29-49 and the light chain variable region amino acid sequence is set out in SEQ ID NO: 3, 4 or 17-19. For example, in some embodiments, the invention provides administering an antibody fragment comprising three heavy chain CDRs having the amino acid sequences set out in SEQ ID NOs: 5-7 or 8-10 and three light chain CDRs have the amino acid sequences set out in SEQ ID NOs: 14-16 or SEQ ID NOs: 20-28 or an antibody fragment comprising a variable heavy chain having the amino acid sequence set out in SEQ ID NO: 2 and a variable light chain having the amino acid sequence set out in SEQ ID NO: 4 or 17-19. In one embodiment, the three heavy chain CDRs have the amino acid sequences set out in SEQ ID NOs: 8-10 and three light chain CDRs have the amino acid sequences set out in SEQ ID NOs: 14-16. In one embodiment, the heavy chain variable region amino acid sequence is set out in SEQ ID NO: 2 and the light chain variable region amino acid sequences is set out in SEQ ID NO: 4.

In various embodiments, the invention provides a method comprising administering an antibody fragment from a monoclonal antibody, for example, from a human antibody.

In various embodiments, the invention provides a method comprising administering an antibody fragment that is a Fab fragment.

In various embodiments, the invention provides a method comprising administering an antibody fragment conjugated to a hydrophobic moiety.

In various embodiments, the invention provides a method comprising administering an antibody fragment in a pharmaceutical composition.

In various embodiments, administering the antibody fragment reduces complications associated with hyperinsulinemia or excess insulin signaling in the subject.

In various embodiments, the subject has a blood glucose level of less than 70 mg/dL prior to administration of an antibody described herein. Optionally, the subject has a blood glucose level of less than 55 mg/dL prior to administration.

In various embodiments, the antibody or fragment thereof is administered at a dose of from 0.1 to 25 mg/kg. In various embodiments, the antibody or fragment thereof is administered at a dose of from 0.3 to 9 mg/kg. Additional doses contemplated include from about 0.3 to 15 mg/kg, from about 0.05 to 10 mg/kg, from about 0.3 to 6.0 mg/kg, from about 0.1 to 3 mg/kg or from about 1 to 6 mg/kg. Exemplary doses include 0.1 mg/kg, 0.3 mg/kg, 0.5 mg/kg, 0.75 mg/kg, 1.0 mg/kg, 1.5 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, or 25 mg/kg. Other doses include 1 mg/day, 2.5 mg/day, 5 mg/day, 10 mg/day, 20 mg/day, 25 mg/day, 50 mg/day, 75 mg/day, 100 mg/day, 150 mg/day, 200 mg/day, 250 mg/day, 500 mg/day or 1000 mg/day.

In various embodiments, the antibody or fragment thereof is administered in a single bolus, for example, every 2-12 hours. Also contemplated is administration once daily, as well as continuous infusion, optionally low dose continuous infusion. Additional doses and methods for administration are discussed in more detail in the Detailed Description.

In various embodiments, the antibody or fragment thereof is administered intravenously, intra-arterially, intraperitoneally, intranasally, intramuscularly, intradermally, subcutaneously, orally or by continuous infusion. In various embodiments, the antibody or fragment thereof is administered via continuous infusion pump or depot.

In various embodiments, the administration of the antibody or fragment thereof increases blood glucose in the subject by 1.5 to 10 fold or by 10 to 40%. In various embodiments, the administration increases blood glucose in the subject by 1.5 to 10 fold or more, or 10 to 40% or more. In various embodiments, the fasting blood glucose is increase by approximately 10%, 15%, 20%, 25%, 30%, 35%, 40%, 45%, 50% or more compared to an untreated subject. In various embodiments, the administration increases blood glucose in the subject by approximately 10 mg/dL or more. In various embodiments, the administration increases blood glucose back into the normal range.

In various embodiments, the subject is on a restricted diet regimen.

In various embodiments, a method according to the invention further comprises administering a second agent. In various embodiments, the second agent is insulin, glucagon, acarbose, octreotide, verapamil or diazoxide.

It is further contemplated that any of the foregoing antibodies or fragments thereof described herein may be concurrently administered with any anti-diabetic agents known in the art or described herein, as adjunct therapy. Compositions comprising an antibody or fragment thereof together with other anti-diabetic agents are also contemplated.

A number of anti-diabetic agents are known in the art, including but not limited to: 1) sulfonylureas (e.g., glimepiride, glisentide, sulfonylurea, AY31637); 2) biguanides (e.g., metformin); 3) alpha-glucosidase inhibitors (e.g., acarbose, miglitol); 4) thiazol-idinediones (e.g., troglitazone, pioglitazone, rosiglitazone, glipizide, balaglitazone, rivoglitazone, netoglitazone, troglitazone, englitazone, AD 5075, T 174, YM 268, R 102380, NC 2100, NIP 223, NIP 221, MK 0767, ciglitazone, adaglitazone, CLX 0921, darglitazone, CP 92768, BM 152054); 5) glucagon-like-peptides (GLP) and GLP analogs or agonists of GLP-1 receptor (e.g., exendin) or stabilizers thereof (e.g., DPP4 inhibitors, such as sitagliptin); and 6) insulin or analogues or mimetics thereof (e.g., LANTUS®).

In various embodiments, the administration of the antibody or fragment thereof prevents or ameliorates one or more symptoms of hypoglycemia selected from the group consisting of pancreatic nesidioblastosis, islet cell enlargement, islet cell hyperplasia, β cell budding, tachycardia, diaphoresis, flushing and reduced cognitive function.

In various embodiments, the administration of the antibody or fragment thereof reduces or eliminates hypoglycemia within 20 minutes, optionally within 15 minutes.

In various embodiments, the antibody or fragment thereof has a duration of action of approximately 4 to 6 hours.

In various embodiments, the subject is non-responsive to dextrose or glucagon therapy.

In various embodiments, the invention provides an antibody or fragment thereof that binds to insulin receptor and/or a complex comprising insulin and insulin receptor with an equilibrium dissociation constant $K_D$ of $10^{-5}$M or less that is capable of reducing binding affinity or binding rate parameter between insulin and insulin receptor (INSR) by about 1.5-fold to 5-fold. In various embodiments, the $K_D$ is at least $10^{-6}$, $10^{-7}$, $10^{-8}$, $10^{-9}$, $10^{-10}$, $10^{-11}$, or $10^{-12}$ M. In various embodiments, the $K_D$ of the antibody fragment is stronger than that of a tetrameric antibody.

In various embodiments, an antibody or fragment thereof that weakens the binding affinity between insulin and INSR is a negative modulator. In some embodiments, an antibody or fragment thereof that weakens the binding affinity between insulin and INSR is an antagonist.

In a related aspect, an antibody or fragment thereof described herein that decreases insulin binding 1.5-fold to 5-fold is also a potent modulator of insulin-mediated signaling.

In certain embodiments, the invention provides a negative allosteric modulator antibody that binds to the insulin receptor with an affinity of at least $10^{-5}$, $10^{-6}$, $10^{-7}$, $10^{-8}$, $10^{-9}$, $10^{-10}$, $10^{-11}$, or $10^{-12}$ M and exhibits an inhibition of insulin mediated signaling (optionally in a pAKT assay) by about 5-fold to 1000-fold.

In various embodiments, the negative allosteric modulator exhibits a less than 2-fold change in the cooperativity factor alpha ($\alpha \leq 2$) and a between 5 to 500-fold change in the cooperativity factor beta ($5 \leq \beta \leq 500$).

The disclosure further contemplates that the antibodies or fragments thereof of the disclosure modulate binding between the INSR and insulin, insulin analogs or insulin mimetics. In various embodiments, the antibodies or fragments thereof of the disclosure also exhibit desirable biological properties including, but not limited to, decreasing glucose uptake in vitro or in vivo in animal models, and preferably the glucose uptake induced by exogenous insulin or insulin production induced by other pharmacological treatment such as sulfonylureas and other drugs. In some embodiments, the antibodies or fragments thereof are capable of decreasing the rate or total amount of glucose uptake, or both.

In another aspect, the invention provides a method of treating a condition or disorder associated with hyperinsulinemia, abnormal production and/or sensitivity to insulin that manifests as excess insulin signaling, comprising administering to a subject in need thereof a negative modulating antibody or an antagonist antibody, or fragment thereof, of the disclosure in an amount effective to treat insulin overproduction and/or sensitivity.

In one embodiment, the disorder associated with insulin sensitivity is selected from the group consisting of cancer, Kaposi's sarcoma, insulinoma, diabetic renal disease, hypoglycemia, nesidioblastosis (KATP-H1 Diffuse Disease, KATP-H1 Focal Disease, or "PHHI"), GDH-H1 (Hyperinsulinism/Hyperammonaemia Syndrome (HI/HA), leucine-sensitive hypoglycemia, or diazoxide-sensitive hypoglycemia), islet cell dysregulation syndrome, idiopathic hypoglycemia of infancy, Persistent Hyperinsulinemic Hypoglycemia of Infancy (PHHI), and Congenital Hyperinsulinism, insulin overdose, hypoglycemia due to renal failure (acute or chronic), Nissen fundoplication, hypoglycemia due to autologous transplant of pancreatic islet cells into the liver, and chronic kidney disease, e.g., type III, IV or V.

In various embodiments, at-risk subjects are subjects for whom it is known that a certain meal provokes hypoglycemia, for example, a meal is given and a mixed meal test (MMT) is performed and an at-risk subject will often have provocation of hypoglycemia.

In various embodiments, at-risk subjects are subjects having prior episodes of hypoglycemia, optionally, a subject being treated with a sulfonylurea medication or insulin, an elderly subject, or a subject having diabetes or congenital hyperinsulinism.

Administration to an at-risk patient before or at the beginning of symptoms can reduce the need for alternate or current standard of care treatments, reduce the need for a pancreatectomy, and reduce the number of doctor visits for the treated subject.

In one embodiment, antibody refers to an antibody or fragment thereof, or a polypeptide comprising an antigen binding domain of an antibody. Exemplary antibodies or antibody fragments include polyclonal antibodies, monoclonal antibodies, chimeric antibodies, humanized antibodies, human antibodies, multispecific antibodies, Fab, Fab', F(ab')2, Fv, domain antibodies (dAb), complementarity determining region (CDR) fragments, CDR-grafted antibodies, single-chain antibodies (scFv), single chain antibody fragments, chimeric antibodies, diabodies, triabodies, tetrabodies, minibody, linear antibody; chelating recombinant antibody, a tribody or bibody, an intrabody, a nanobody, a small modular immunopharmaceutical (SMIP), a antigen-binding-domain immunoglobulin fusion protein, a camelized antibody, a VHH containing antibody, or a variant or a derivative thereof, and polypeptides that contain at least a portion of an immunoglobulin that is sufficient to confer specific antigen binding to the polypeptide, such as one, two, three, four, five or six CDR sequences. In one embodiment, the antibody is a monoclonal antibody. In a related embodiment, the antibody is a human antibody.

In exemplary embodiments, the methods herein contemplate use of:

a monoclonal antibody or fragment thereof that retains any one, two, three, four, five, or six of HCDR1, HCDR2, HCDR3, LCDR1, LCDR2, or LCDR3 of any one of SEQ ID NOs: 5-10 and SEQ ID NO: 50-112 and SEQ ID NOs: 11-16 and SEQ ID NOs: 20-28, respectively, optionally including one or two mutations in such CDR(s), e.g., a conservative or non-conservative substitution;

a monoclonal antibody or fragment thereof that retains all of HCDR1, HCDR2, HCDR3, or the heavy chain variable region of any one of SEQ ID NOs: 5-10, 50-112 or SEQ ID NOs: 1, 2 or 29-49, respectively, optionally including one or two mutations in any of such CDR(s), optionally further comprising any suitable heavy chain constant region, e.g., IgG1, IgG2, IgG3, IgG4, IgM, IgA1, IgA2, or IgE or hybrid thereof;

a monoclonal antibody or fragment thereof that retains all of LCDR1, LCDR2, LCDR3, or the light chain variable region of any one SEQ ID NOs: 11-16 or SEQ ID NOs: 3 or 4, or SEQ ID NOs: 20-28 or SEQ ID NOs: 17-19, optionally including one or two mutations in any of such CDR(s), optionally further comprising any suitable light chain constant region, e.g. a kappa or lambda light chain constant region;

a purified preparation of a monoclonal antibody, comprising the heavy chain variable region and light chain variable regions as set forth in SEQ ID NOs: 1, 2, 29-49 and 4 or 17-19;

a purified preparation of a monoclonal antibody, comprising the heavy chain variable region and light chain variable regions as set forth in SEQ ID NOs: 2 and 4 or 17-19;

a monoclonal antibody that binds to the same linear or three-dimensional epitope of INSR as an antibody comprising a variable region set out in any one of SEQ ID NOs: 1-4, 17-19 or 29-49, e.g., as determined through X-ray crystallography or other biophysical or biochemical techniques such as deuterium exchange mass spectrometry, alanine scanning and peptide fragment ELISA;

a monoclonal antibody that competes with an antibody comprising a variable region set out in any one of SEQ ID NOs: 1-4, 17-19 or 29-49, optionally paired as in Table 1, for binding to human INSR by more than about 75%, more than about 80%, or more than about 81%, 82%, 83%, 84%, 85%, 86%, 87%, 88%, 89%, 90%, 91%, 92%, 93%, 94% or 95%.

In some embodiments, the antibody comprises all three light chain CDRs, all three heavy chain CDRs, or all six CDRs of an antibody comprising a variable region set out in SEQ ID NOs: 1-4, 17-19 or 29-49. In some exemplary embodiments, two light chain CDRs from an antibody may be combined with a third light chain CDR from a different antibody. Alternatively, a LCDR1 from one antibody can be combined with a LCDR2 from a different antibody and a LCDR3 from yet another antibody, particularly where the CDRs are highly homologous. Similarly, two heavy chain CDRs from an antibody may be combined with a third heavy chain CDR from a different antibody; or a HCDR1 from one antibody can be combined with a HCDR2 from a different antibody and a HCDR3 from yet another antibody, particularly where the CDRs are highly homologous.

Consensus CDRs may also be used. Any one of the consensus CDRs derived herein may be combined with two other CDRs from the same chain (e.g., heavy or light) of any of the antibodies described herein, e.g. to form a suitable heavy or light chain variable region. Exemplary consensus sequences can be determined form the sequences set out in Table 1 and FIG. 19. Exemplary consensus sequences can be determined for the heavy and/or light chain variable region sequences, as well as for HCDR1, HCDR2, HCDR3, LCDR1, LCDR2 and/or LCDR3 amino acid sequences.

In another aspect, the disclosure provides for use of variants or derivatives of the antibodies described herein. For example, in one embodiment the antibody is labeled with a detectable moiety as described herein. In a further embodiment, the antibody is conjugated to a hydrophobic moiety described herein.

Variants of the antibodies include antibodies having a mutation or alteration in an amino acid sequence provided herein, including an amino acid insertion, deletion or substitution, e.g., a conservative or non-conservative substitution.

In some embodiments, an antibody is provided that comprises a polypeptide having an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to the heavy chain variable region set out in SEQ ID NOs: 1, 2 or 29-49 and/or an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to the light chain variable region set out in SEQ ID NO: 3 or 4 or 17-19, the antibody further comprising at least one, two, three, four, five or all of CDRH1, CDRH2, CDRH3, CDRL1, CDRL2 or CDRL3. In some embodiments, the amino acid sequence with percentage identity to the light chain variable region may comprise one, two or three of the light chain CDRs. In other embodiments, the amino acid sequence with percentage identity to the heavy chain variable region may comprise one, two, or three of the heavy chain CDRs.

It is contemplated that the antibodies used herein may have one, or two or more amino acid substitutions in the CDR regions of the antibody, e.g. conservative substitutions.

In various embodiments, the antibody used in the methods comprises a heavy chain variable region selected from the group consisting of SEQ ID NOs: 1, 2 or 29-49 and a light chain variable region selected from the group consisting of SEQ ID NOs: 3 or 4 or 17-19. In various embodiments, the variable heavy chain is set out in SEQ ID NO: 2 and the variable light chain is set out in SEQ ID NO: 4 or 17-19.

In various embodiments, the antibody comprises three heavy chain CDRs set out in SEQ ID NOs: 5-7, 8-10 or 50-112 and three light chain CDRs set out in SEQ ID NOs: 11-13, 14-16, 20-22, 23-25 and 26-28.

In one embodiment, the variable heavy chain is set out in SEQ ID NO: 2 and the variable light chain is set out in SEQ ID NO: 4. In another embodiment, the antibody comprises three heavy chain CDRs set out in SEQ ID NOs: 8-10 and three light chain CDRs set out in SEQ ID NOs: 14-16 or 20-22, 23-25 and 26-28.

In various embodiments, the administration takes place during a fasting regimen.

In various embodiments, the administration induces insulin resistance. In various embodiments, insulin resistance is measured by meal tolerance test, insulin tolerance test fasting HOMA-IR assay and/or oral glucose tolerance test.

Use of any of the foregoing antibodies or polypeptides described herein that modulate the insulin-INSR signaling interaction in preparation of a medicament for treatment of any of the disorders described herein is also contemplated. Syringes, e.g., single use or pre-filled syringes, sterile sealed containers, e.g. vials, bottle, vessel, and/or kits or packages comprising any of the foregoing antibodies or polypeptides, optionally with suitable instructions for use, are also contemplated.

It is understood that each feature or embodiment, or combination, described herein is a non-limiting, illustrative example of any of the aspects of the disclosure and, as such, is meant to be combinable with any other feature or embodiment, or combination, described herein. For example, where features are described with language such as "one embodiment", "some embodiments", "further embodiment", "specific exemplary embodiments", and/or "another embodiment", each of these types of embodiments is a non-limiting example of a feature that is intended to be combined with any other feature, or combination of features, described herein without having to list every possible combination. Such features or combinations of features apply to any of the aspects of the disclosure. Similarly, where a method describes using or identifying polypeptide binding agents, such as antibodies, characterized by certain features, polypeptide binding agents characterized by those features are also contemplated by the disclosure. Where examples of values falling within ranges are disclosed, any of these examples are contemplated as possible endpoints of a range, any and all numeric values between such endpoints are contemplated, and any and all combinations of upper and lower endpoints are envisioned.

BRIEF DESCRIPTION OF THE DRAWINGS

FIG. 3A shows pAKT assay results showing changes in sensitivity (EC50) of the insulin dose response effected by anti-human INSR modulating XPA.15.247 parent antibody and its variant XPA.15.247.2.018. Results from monomeric Fab fragments of XPA.15.247 and XPA.15.247.2.018 antibodies are also shown. FIG. 3B shows the potency of XPA.15.247 parent antibody and its variant XPA.15.247.2.018 antibody and Fab fragment on modulating pAkt activity in CHO-huINSR cells assessed at the EC80 concentration of insulin.

FIG. 4A shows the effect of XPA.15.247 parent antibody on sulphonylurea-induced hypoglycemia in Wistar rats, and FIG. 4B shows the effect of the variant XPA.15.247.2.018 IgG on sulphonylurea-induced hypoglycemia in Wistar rats; and FIG. 4C shows the effect of the variant XPA.15.247.2.018 Fab on sulphonylurea-induced hypoglycemia in Wistar rats. FIG. 4D shows the glucose readings during the full time course of the study.

FIG. 5A shows the effect of XPA.15.247 parent antibody on insulin-induced hypoglycemia in Sprague-Dawley rats, and FIG. 5B shows the effect of the variant XPA.15.247.2.018 Fab on insulin-induced hypoglycemia in Sprague-Dawley rats.

FIG. 6 shows the amino acid sequences of antibodies and fragments thereof according to the disclosure.

FIG. 9A shows the early timepoints up to 8 hours; FIG. 9B shows the full timecourse up to 48 hours.

FIGS. 10A-10C show pharmacokinetics and pharmacodynamics of XPA.15.247.2.018 Fab in Gottingen minipigs after intravenous, intramuscular or subcutaneous administration. FIG. 10A shows the early timepoints up to 8 hours while FIG. 10B shows the full timecourse. FIG. 10C shows the blood glucose change of XPA.15.247.2.018 Fab in Gottingen minipigs.

FIG. 11A shows intravenous administration of XPA.15.247.2.018 Fab at both 10 mg/kg and 2 mg/kg; FIG. 11B shows intramuscular administration of XPA.15.247.2.018 Fab at 5 mg/kg; and FIG. 11C shows subcutaneous administration of XPA.15.247.2.018 Fab at 9 mg/kg.

FIG. 13A shows the blood glucose level after 8 hour fasting; FIG. 13B shows the blood glucose level without fasting.

FIG. 14A shows the C-peptide levels after 8 hour fasting; FIG. 14B shows the C-peptide levels without fasting; FIG. 14C shows the insulin levels after 8 hour fasting; FIG. 14D shows the insulin levels without fasting.

FIG. 15A shows the changes in body weight during the study; FIG. 15B shows weight changes in liver at the end of the study; FIG. 15C shows weight changes in kidneys at the end of the study.

FIG. 16A shows the blood glucose level on day 1; blood glucose at t0 is collected after 8 hr fasting; FIG. 16B shows the blood glucose level on day 3; blood glucose at t0 is collected after 8 hr fasting FIG. 17A-17B shows the C-peptide levels on day 1 and day 3, respectively; the C-peptide levels at t0 was collected after 8 hr fasting; FIGS. 17C-17D show the insulin levels on day 1 and day 3, respectively; the insulin level at t0 was collected after 8 hr fasting.

FIG. 18A shows the changes in body weight during the study; FIG. 18B shows weight changes in liver at the end of the study; FIG. 18C shows weight changes in kidneys at the end of the study.

FIG. 19 sets out the CDR sequences of XPA.247.2.018 affinity matured heavy chain variable region sequences, as well as the affinity, potency and binding to different species of the different clones.

FIG. 20 illustrates the trends in mutation hot spots in heavy chain CDR1 and CDR3 of selected antibody clones from affinity matured XPA.15.247.2.018 Fab.

DETAILED DESCRIPTION

Figure 1:
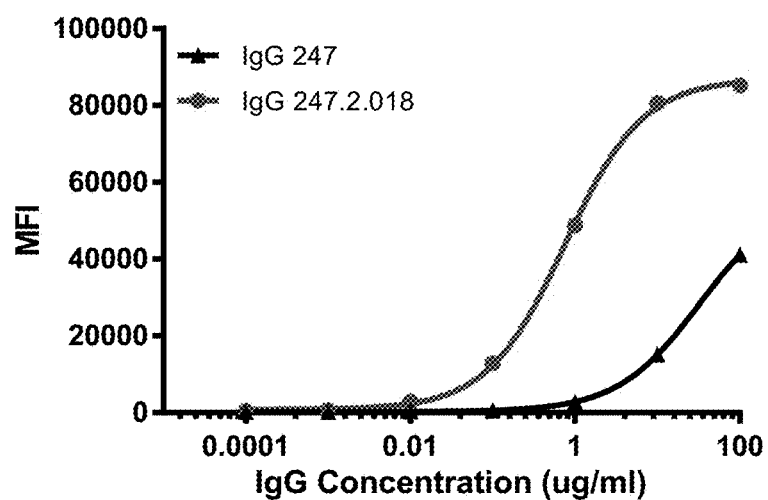
FIG. 1 depicts representative results comparing binding of XPA.15.247 parent antibody (IgG 247) and its variant XPA.15.247.2.018 (IgG 247.2.018) on CHO cells expressing the human INSR employing flow cytometry.

The disclosure provides antibodies specific for the insulin receptor (INSR) or the insulin receptor-insulin complex and uses thereof in the treatment of disorders related to aberrant glucose levels, e.g. hypoglycemia, including hypoglycemia due to endogenous or exogenous hyperinsulinemia, insulin overdose (insulin-induced hypoglycemia) and disease hypoglycemic states characterized by abnormal glucose levels, sulfonylurea-induced hypoglycemia, and post-prandial hypoglycemia. Such modulators could also be used to prevent the occurrence of the hypoglycemia in an at-risk subject such Type 1 or Type 2 diabetic patients.

Not to be bound by theory, but it is contemplated that modulation of a signaling complex by an antibody or antibody fragment disclosed herein can result in a decrease in sensitivity to signal input and concomitant decreases in signal transduction. Administration of a negative modulator antibody decreases the sensitivity of the cellular pathway and/or absolute levels of the cellular response.

Definitions

The term "compound" refers to any chemical compound, organic or inorganic, endogenous or exogenous, including, without limitation, polypeptides, proteins, peptides, small molecules, nucleic acids (e.g., DNA and RNA), carbohydrates, lipids, fatty acids, steroids, purines, pyrimidines, peptidomimetics, polyketides and derivatives, structural analogs or combinations thereof. "Endogenous" means naturally occurring in a mammal, while "exogenous" means not naturally occurring in the mammal, e.g., an administered foreign compound, whether naturally occurring or a man-made compound.

The term "polypeptide binding agent" refers to a polypeptide that is capable of specifically binding an antigen, e.g. a target or its signaling partner, or that is capable of binding an antigen with a measurable binding affinity. Examples of polypeptide binding agents include antibodies, peptibodies, polypeptides and peptides, optionally conjugated to other peptide moieties or non-peptidic moieties. Antigens to which a polypeptide binding agent may bind include any proteinaceous or non-proteinaceous molecule that is capable of eliciting an antibody response, or that is capable of binding to a polypeptide binding agent with detectable binding affinity greater than non-specific binding. The antigen to which a modulating polypeptide binding agent binds may include a target, a signaling partner of a target, and/or a complex comprising the target and its signaling partner.

The term "antibody" is used in the broadest sense and includes fully assembled antibodies, tetrameric antibodies, monoclonal antibodies, polyclonal antibodies, multispecific antibodies (e.g., bispecific antibodies), antibody fragments that can bind an antigen (e.g., Fab', F'(ab)2, Fv, single chain antibodies, diabodies), and recombinant peptides comprising the forgoing as long as they exhibit the desired biological activity. An "immunoglobulin" or "tetrameric antibody" is a tetrameric glycoprotein that consists of two heavy chains and two light chains, each comprising a variable region and a constant region. Antigen-binding portions may be produced by recombinant DNA techniques or by enzymatic or chemical cleavage of intact antibodies. Antibody fragments or antigen-binding portions include, inter alia, Fab, Fab', F(ab')2, Fv, domain antibody (dAb), complementarity determining region (CDR) fragments, CDR-grafted antibodies, single-chain antibodies (scFv), single chain antibody fragments, chimeric antibodies, diabodies, triabodies, tetrabodies, minibody, linear antibody; chelating recombinant antibody, a tribody or bibody, an intrabody, a nanobody, a small modular immunopharmaceutical (SMIP), a antigen-binding-domain immunoglobulin fusion protein, a camelized antibody, a VHH containing antibody, or a variant or a derivative thereof, and polypeptides that contain at least a portion of an immunoglobulin that is sufficient to confer specific antigen binding to the polypeptide, such as one, two, three, four, five or six CDR sequences, as long as the antibody retains the desired biological activity.

"Monoclonal antibody" refers to an antibody obtained from a population of substantially homogeneous antibodies, i.e., the individual antibodies comprising the population are identical except for possible naturally occurring mutations that may be present in minor amounts.

"Antibody variant" as used herein refers to an antibody polypeptide sequence that contains at least one amino acid substitution, deletion, or insertion in the variable region of the natural antibody variable region domains. Variants may be substantially homologous or substantially identical to the unmodified antibody.

A "chimeric antibody," as used herein, refers to an antibody containing sequence derived from two different antibodies (see, e.g., U.S. Pat. No. 4,816,567) which typically originate from different species. Most typically, chimeric antibodies comprise human and rodent antibody fragments, generally human constant and mouse variable regions.

A "neutralizing antibody" is an antibody molecule which is able to eliminate or significantly reduce a biological function of an antigen to which it binds. Accordingly, a "neutralizing" antibody is capable of eliminating or significantly reducing a biological function, such as enzyme activity, ligand binding, or intracellular signaling.

An "isolated" antibody is one that has been identified and separated and recovered from a component of its natural environment. Contaminant components of its natural environment are materials that would interfere with diagnostic or therapeutic uses for the antibody, and may include enzymes, hormones, and other proteinaceous or non-proteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

"Heavy chain variable region" as used herein refers to the region of the antibody molecule comprising at least one complementarity determining region (CDR) of said antibody heavy chain variable domain. The heavy chain variable region may contain one, two, or three CDR(s) of said antibody heavy chain.

"Light chain variable region" as used herein refers to the region of an antibody molecule, comprising at least one complementarity determining region (CDR) of said antibody light chain variable domain. The light chain variable region may contain one, two, or three CDR(s) of said antibody light chain, which may be either a kappa or lambda light chain depending on the antibody.

As used herein, an antibody that "specifically binds" is "antigen specific", is "specific for" antigen target or is "immunoreactive" with an antigen refers to an antibody or polypeptide binding agent used herein that binds an antigen with greater affinity than other antigens of similar sequence. In one aspect, the polypeptide binding agents, or fragments, variants, or derivatives thereof, will bind with a greater affinity to human antigen as compared to its binding affinity to similar antigens of other, i.e., non-human, species, but polypeptide binding agents that recognize and bind orthologs of the target are within the scope of the methods.

For example, a polypeptide binding agent that is an antibody or fragment thereof "specific for" its cognate antigen indicates that the variable regions of the antibodies recognize and bind the desired antigen with a detectable preference (e.g., where the desired antigen is a polypeptide, the variable regions of the antibodies are able to distinguish the antigen polypeptide from other known polypeptides of the same family, by virtue of measurable differences in binding affinity, despite the possible existence of localized sequence identity, homology, or similarity between family members). It will be understood that specific antibodies may also interact with other proteins (for example, *S. aureus* protein A or other antibodies in ELISA techniques) through interactions with sequences outside the variable region of the antibodies, and in particular, in the constant region of the molecule. Screening assays to determine binding specificity of a polypeptide binding agent, e.g. antibody, for use in the methods herein are well known and routinely practiced in the art. For a comprehensive discussion of such assays, see Harlow et al. (Eds), Antibodies A Laboratory Manual; Cold Spring Harbor Laboratory; Cold Spring Harbor, N.Y. (1988), Chapter 6. Antibodies for use in the methods can be produced using any method known in the art.

The term "epitope" refers to that portion of any molecule capable of being recognized by and bound by a selective binding agent at one or more of the antigen binding regions. Epitopes usually consist of chemically active surface groupings of molecules, such as, amino acids or carbohydrate side chains, and have specific three-dimensional structural characteristics as well as specific charge characteristics. Epitopes as used herein may be contiguous or non-contiguous.

The term "derivative" when used in connection with polypeptide binding agents and polypeptides herein refers to polypeptides chemically modified by such techniques as ubiquitination, conjugation to therapeutic or diagnostic agents, labeling (e.g., with radionuclides or various enzymes), covalent polymer attachment such as pegylation (derivatization with polyethylene glycol) and insertion or substitution by chemical synthesis of amino acids such as ornithine, which do not normally occur in human proteins. Derivatives retain the binding properties of underivatized molecules of the starting material.

"Detectable moiety" or a "label" refers to a composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin-streptavadin, dioxigenin, haptens and proteins for which antisera or monoclonal antibodies are available, or nucleic acid molecules with a sequence complementary to another labeled nucleic acid molecule. The detectable moiety often generates a measurable signal, such as a radioactive, chromogenic, or fluorescent signal, that can be used to quantitate the amount of bound detectable moiety in a sample.

"Peptides" or "oligopeptides" are short amino acid sequences, typically between 3 and 100 amino acid residues in length and encompass naturally occurring amino acid residues and non-naturally occurring analogs of residues which may be used singly or in combination with naturally occurring amino acid residues in order to give the peptide a particular conformational specificity or a particular biological activity, such as resistance to proteolysis. Peptides include repeats of peptide sequences and may include 2, 3, 4, 5, 6, 7, 8, 9, 10 or more copies of an amino acid sequence arranged head-to-tail or head-to-head. Peptides may be conjugated to non-peptidic moieties. Peptides include dimers, trimers or higher order multimers, e.g. formed through conjugation to other polymeric or non-polymeric moieties, such as PEG.

"Polypeptides" are longer amino acid sequences, typically 100 or more amino acid residues in length, and encompass naturally occurring amino acid residues and non-naturally occurring analogs of residues which may be used singly or in combination with naturally occurring amino acid residues in order to give the polypeptide a particular conformational specificity or a particular biological activity, such as resistance to proteolysis.

As used herein, a "peptibody" is a fusion polypeptide comprising one or more peptides fused to all or a portion of an immunoglobulin (Ig) constant region. See, e.g., U.S. Pat. No. 6,660,843. The peptide may be any naturally occurring or recombinantly prepared or chemically synthesized peptide that binds to the antigen. The peptide may be repeated and may include 2, 3, 4, 5, 6, 7, 8, 9, 10 or more copies of an amino acid sequence arranged head-to-tail or head-to-head. The portion of the Ig constant region may include at least one constant region domain (e.g., CH1, CH2, CH3, and/or CH4), multiple domains (e.g., CH2 with CH3), multiple copies of domains (e.g., CH2-CH2), any fragment of a constant domain that retains the desired activity, e.g. the salvage receptor epitope responsible for the prolonged half-life of immunoglobulins in circulation, or any combinations thereof.

A "small" molecule or "small" organic molecule is defined herein as a non-polymeric organic chemical compound having a molecular weight of about 1000 Daltons or less.

As used herein, a "signaling complex" is an assembly of proteins and/or endogenous or exogenous compounds that mediate the transduction of a cellular signal. Examples of a signaling complex include, but are not limited to, a ligand bound to a membrane bound receptor, an enzyme bound to a substrate or any cellular molecules that associate to propagate biochemical reactions that are involved in a signal cascade. Signaling complexes can also include coreceptors, cofactors, scaffold proteins, allosteric modulators and numerous other types of proteins and molecules that are involved in cellular signal transduction. Signaling complexes can be formed transiently or can be long lived. The molecular constituents or components of a signaling complex can vary over time and can be dependent on activation state of each component and the cellular environment. Signaling complexes can undergo chemical modification and regulation that can induce a spectrum of effects on the complex including subtle changes in transduction activity, complete inactivation and constitutive activation or both positive and negative modulation.

The term "therapeutically effective amount" is used herein to indicate the amount of target-specific composition that is effective to ameliorate or lessen symptoms or signs of disease associated with abnormal (e.g. abnormally high or abnormally low) signaling of the signaling complex.

As used herein, "binding" is the physical association between two or more distinct molecular entities that results from a specific network of non-covalent interactions consisting of one or more of the weak forces including hydrogen bonds, Van der Waals, ion-dipole and hydrophobic interactions and the strong force ionic bonds. The level or degree of binding may be measured in terms of affinity. Affinity is a measure of the strength of the binding interaction between two or more distinct molecular entities that can be defined by equilibrium binding constants or kinetic binding rate parameters. Examples of suitable constants or parameters and their measurement units are well known in the art and include but are not limited to equilibrium association constant ($K_A$), e.g. about $10^5 M^{-1}$ or higher, about $10^6 M^{-1}$ or higher, about $10^7 M^{-1}$ or higher, about $10^8 M^{-1}$ or higher, about $10^9 M^{-1}$ or higher, about $10^{10} M^{-1}$ or higher, about $10^{11} M^{-1}$ or higher or about $10^{12} M^{-1}$ or higher; equilibrium dissociation constant ($K_D$), e.g., about $10^{-5} M$ or less, or about $10^{-6} M$ or less, or about $10^{-7} M$ or less, or about $10^{-8} M$ or less, or about $10^{-9} M$ or less, or about $10^{-10} M$ or less, or about $10^{-11} M$ or less, or about $10^{-12} M$ or less; on-rate (e.g., $sec^{-1}$, $mol^{-1}$) and off-rate (e.g., $sec^{-1}$)). In the case of $K_A$, higher values mean "stronger" or "strengthened" binding affinity while in the case of $K_D$, lower values mean "stronger" or "strengthened" binding affinity. As used herein, a "strengthened" binding rate parameter means increased residency time, stronger association or weaker dissociation. As used herein, a "weakened" binding rate parameter means decreased residency time, weaker association or stronger dissociation. In the case of on-rate, higher values mean faster or more frequent association and thus generally result in strengthened binding affinity. In the case of off-rate, lower values generally mean slower dissociation and thus generally result in stronger binding affinity. However, it is the ratio of the on-rate and off-rate that indicates binding affinity, as explained in further detail later.

Affinity between two compounds, e.g., between an antibody and an antigen, or between first and second components of a signaling complex, may be measured directly or indirectly. Indirect measurement of affinity may be performed using surrogate properties that are indicative of, and/or proportional to, affinity. Such surrogate properties include: the quantity or level of binding of a first component to a second component of a signaling complex, or a biophysical characteristic of the first component or the second component that is predictive of or correlated to the apparent binding affinity of the first component for the second component. Specific examples include measuring the quantity or level of binding of first component to a second component at a subsaturating concentration of either the first or the second component. Other biophysical characteristics that can be measured include, but are not limited to, the net molecular charge, rotational activity, diffusion rate, melting temperature, electrostatic steering, or conformation of one or both of the first and second components. Yet other biophysical characteristics that can be measured include determining stability of a binding interaction to the impact of varying temperature, pH, or ionic strength.

Measured affinity is dependent on the exact conditions used to make the measurement including, among many other factors, concentration of binding components, assay setup, valence of binding components, buffer composition, pH, ionic strength and temperature as well as additional components added to the binding reaction such as allosteric modulators and regulators. Quantitative and qualitative methods may be used to measure both the absolute and relative strength of binding interactions.

Apparent affinity is a measure of the strength of the binding interaction between two or more distinct molecular entities under conditions where the affinity is altered by conditions or components in the binding reaction such as allosteric modulators, inhibitors, binding component valence etc.

As used herein a "subsaturating concentration" is a concentration of one or more components in a binding reaction that is significantly below the binding affinity $K_D$ and/or a concentration of one component in a binding reaction that is less than is required to occupy all of the binding sites of the other component(s). Under subsaturating conditions a significant percentage of one of the binding components in the binding reaction has available binding sites.

A receptor "antagonist" is a type of receptor ligand or drug that does not provoke a biological response itself upon binding to a receptor, but blocks or dampens agonist-mediated responses. Antagonists may have affinity but no efficacy for their cognate receptors, and binding will disrupt the interaction and inhibit the function of an agonist or inverse agonist at receptors. Antagonists mediate their effects by binding to the active site or to allosteric sites on receptors, or they may interact at unique binding sites not normally involved in the biological regulation of the receptor's activity. Antagonist activity may be reversible or irreversible depending on the longevity of the antagonist-receptor complex, which, in turn, depends on the nature of antagonist receptor binding. The majority of antagonists achieve their potency by competing with endogenous ligands or substrates at structurally-defined binding sites on receptors.

Antagonists display no efficacy to activate the receptors they bind. Once bound, however, antagonists may inhibit the function of agonists, inverse agonists and partial agonists. In functional antagonist assays, a dose-response curve measures the effect of the ability of a range of concentrations of antagonists to reverse the activity of an agonist. The potency of an antagonist is usually defined by its $IC_{50}$ value. This can be calculated for a given antagonist by determining the concentration of antagonist needed to elicit half inhibition of the maximum biological response of an agonist. The lower the $IC_{50}$, the greater the potency of the antagonist.

Competitive, or orthosteric, antagonists reversibly bind to receptors at the same binding site (active site) as the ligand or agonist, but without activating the receptor, thereby competing with agonist for the same binding site on the receptor. Non-competitive, or allosteric, antagonists bind to a separate binding site from the agonist, exerting their action to that receptor via that separate binding site. Thus, they do not compete with agonists for binding. Uncompetitive antagonists differ from non-competitive antagonists in that they require receptor activation by an agonist before they can bind to a separate allosteric binding site.

"Insulin resistance" describes a condition in which physiological amounts of insulin are inadequate to produce a normal insulin response from cells or tissues.

The present disclosure encompasses use of insulin-INSR signaling complex modulators that offer unique advantages over existing therapies. They act at the level of the INSR, which should allow induction of the entire range of actions of insulin while minimizing unwanted side effects. It is hypothesized that the antibodies can provide more precise control of glucose and insulin levels. Targeting the extracellular region of the INSR allows for the use of biological molecules as insulin-INSR signaling complex modulators that modulate the effect of endogenous insulin; these may have advantages such as improved half-life, reduced dosage or frequency of dosage, reduced toxicity and greater ease of manufacture.

Methods of identifying antibodies that are modulators of insulin signaling are disclosed in co-owned U.S. Pat. No. 8,926,976 and patent application U.S. Ser. No. 14/555,233 and U.S. Ser. No. 12/890,590, herein incorporated by reference.

The Insulin Receptor (INSR)

The INSR is a tyrosine kinase receptor found in organisms as primitive as cnidarians and insects. In higher organisms it is essential for glucose homeostasis. Mouse knockout studies have also shown the INSR to be important in adipogenesis, neovascularization, the regulation of hepatic glucose synthesis and glucose-induced pancreatic insulin secretion (Kitamura et al, *Ann. Rev. Physiol* 65: 313-332, 2003). INSR signaling is also important in the brain, where it is involved in the regulation of food intake, peripheral fat deposition and the reproductive endocrine axis as well as in learning and memory (Wada et al, *J. Pharmacol. Sci* 99: 128-143, 2005). Dysfunctional INSR signaling has been implicated in diseases including type I and type II diabetes, dementia and cancer.

The domains of the closely related insulin-like growth factor receptor (IGFR-1) exhibit high (47-67%) amino acid identity with the INSR. While similar in structure, IGF-IR and INSR serve different physiological functions. IGF-IR is expressed in almost all normal adult tissue except for liver, which is itself the major site of IGF-I production. INSR is primarily involved in metabolic functions whereas IGF-IR mediates growth and differentiation (Adams et al, *Cell. Mol. Life Sci.* 57: 1050-1093, 2000).

INSR exists as two splice variant isoforms, INSR-A and INSR-B, which respectively lack or contain the 12 amino acids coded by exon 11. The longer variant, INSR-B, is the isoform responsible for signaling metabolic responses. In contrast, INSR-A signals predominantly mitogenic responses, is the preferentially expressed isoform in several cancers (Denley et al., *Horn. Metab. Res.* 35: 778-785, 2003) and is capable of binding insulin-like growth factor 2 (IGF-II) with high affinity (Denley et al, *Mol. Endocrinol.* 18: 2502-2512, 2004).

The mature human INSR is a homodimer comprising two α subunits and two β subunits (chains). The α and β chains are encoded by a single gene and arise from the post-translational cleavage of a 1370 amino acid precursor at a furin cleavage site located at residues 720-723. The α-chain and 194 residues of the β-chain comprise the extracellular protion of the INSR. There is a single transmembrane sequence and a 403 residue cytoplasmic domain containing a tyrosine kinase. The N-terminal half of each ectodomain monomer consists of two homologous leucine-rich repeat domains (L1 and L2) of approximately 150 amino acids, separated by a cysteine-rich region (CR), also approximately 150 amino acids in size. The C-terminal half of each ectodomain monomer (approximately 460 residues) consists of three fibronectin type III domains (FnIII-1, FnIII-2 and FnIII-3). The FnIII-2 domain contains an insert domain (ID) of approximately 120 residues, within which lies the furin cleavage site that generates the α and β chains of the mature receptor. Intracellularly, each monomer contains a tyrosine kinase catalytic domain flanked by two regulatory regions (the juxtmembrane region and the C-tail) that contain the phosphotyrosine binding sites for signaling molecules (Ward et al, *Acta Physiol.* 192: 3-9, 2008).

Models for insulin binding propose that, in the basal state, the INSR homodimer contains two identical pairs of binding sites (referred to as Site 1 and Site 2) on each monomer (De Meyts, *Bioessays* 26: 1351-1362, 2004). Binding of insulin to a low affinity site (Site 1) on one α-subunit is followed by a second binding event between the bound insulin and a different region of the second INSR α-subunit (Site 2). This ligand-mediated bridging between the two α subunits generates the high affinity state that results in signal transduction. In contrast, soluble INSR ectodomain, which is not tethered at its C-terminus, cannot generate the high affinity receptor-ligand complex. It can bind two molecules of insulin simultaneously at its two Site 1's, but only with low affinity (Adams et al, *Cell. Mol. Life Sci.* 57: 1050-1093, 2000). Site 1 is thought to be comprised of elements from the central β-sheet of the L1 domain and the last 16 residues of the α-chain (referred to as the CT peptide). Site 2 most likely includes the loops at the junction of FnIII-1 and FnIII-2. Insulin binding is thought to involve structural changes in both insulin and its receptor (Ward and Lawrence, *BioEssays* 31: 422-434, 2009).

Once an insulin molecule has docked onto the receptor and effected its action, it may be released back into the extracellular environment or it may be degraded by the cell. Degradation normally involves endocytosis of the insulin-INSR complex followed by the action of insulin degrading enzyme. Most insulin molecules are degraded by liver cells. It has been estimated that a typical insulin molecule is finally degraded about 71 minutes after its initial release into circulation (Duckworth et al, *Endocr. Rev.* 19(5): 608-24, 1998).

Insulin Signaling

Insulin induces a signaling network of molecules, carrying the information from the INSR to the effector proteins involved in metabolism and growth. Insulin binding to INSR induces a conformational change that promotes activation of an intrinsic tyrosine kinase activity, leading to autophosphorylation of the INSR β-subunit. Insulin receptor substrate (IRS) proteins are recruited to the plasma membrane through an interaction with the phosphorylated INSR, and these also become phosphorylated on tyrosine residues, promoting recruitment of additional signaling proteins to the complex resulting in signaling through two major pathways (1) the PI3 kinase/PDK1/PKB pathway which primarily regulates metabolism, with some influence on growth, and (2) the Ras/ERK mitogenic pathway which primarily regulates cell growth.

Certain marketed insulin analogues have been reported to display IGF-1-like mitogenic and anti-apoptotic activities in cultured cancer cells, raising questions over their long-term safety in humans (Weinstein et al, *Diabetes Metab Res Rev* 25: 41-49, 2009).

Types and Sources of Antibodies

The present disclosure encompasses use of target specific antibodies that bind to insulin receptor or the insulin/insulin receptor complex. In exemplary embodiments, a target specific antibody described herein can comprise a human kappa (κ) or a human lambda (λ) light chain or an amino acid sequence derived therefrom, or a human heavy chain or a sequence derived therefrom, or both heavy and light chains together in a single chain, dimeric, tetrameric or other form. In some embodiments, a heavy chain and a light chain of a target specific immunoglobulin are different amino acid molecules. In other embodiments, the same amino acid molecule contains a heavy chain variable region and a light chain variable region of a target specific antibody.

The term "antibody" is used in the broadest sense and includes fully assembled antibodies, tetrameric antibodies, monoclonal antibodies, polyclonal antibodies, multispecific antibodies (e.g., bispecific antibodies), human and humanized antibodies, antibody fragments that can bind an antigen (e.g., Fab', F'(ab)2, Fv, single chain antibodies, diabodies), and recombinant peptides comprising the forgoing as long as they exhibit the desired biological activity. An "immunoglobulin" or "tetrameric antibody" is a tetrameric glycoprotein that consists of two heavy chains and two light chains, each comprising a variable region and a constant region. Antigen-binding portions may be produced by recombinant DNA techniques or by enzymatic or chemical cleavage of intact antibodies. Antibody fragments or antigen-binding portions include, inter alia, Fab, Fab', F(ab')2, Fv, domain antibody (dAb), complementarity determining region (CDR) fragments, single-chain antibodies (scFv), single chain antibody fragments, chimeric antibodies, diabodies, triabodies, tetrabodies, minibody, linear antibody; chelating recombinant antibody, a tribody or bibody, an intrabody, a nanobody, a small modular immunopharmaceutical (SMIP), a antigen-binding-domain immunoglobulin fusion protein, a camelized antibody, a VHH containing antibody, or a variant or a derivative thereof, and polypeptides that contain at least a portion of an immunoglobulin that is sufficient to confer specific antigen binding to the polypeptide, as long as the antibody retains the desired biological activity.

In a naturally-occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa (κ) and lambda (λ) light chains. Heavy chains are classified as mu (μ), delta (Δ), gamma (γ), alpha (α), and epsilon (ε), and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology, Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains (Chothia et al., *J. Mol. Biol.* 196:901-917, 1987).

Immunoglobulin variable domains exhibit the same general structure of relatively conserved framework regions (FR) joined by three hypervariable regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al., Sequences of Proteins of Immunological Interest, National Institutes of Health, Bethesda, Md., 1987 and 1991)); Chothia & Lesk, *J. Mol. Biol.* 196:901-917, 1987; or Chothia et al., *Nature* 342:878-883, 1989.

The hypervariable region of an antibody refers to the CDR amino acid residues of an antibody which are responsible for antigen-binding. The hypervariable region comprises amino acid residues from a CDR (i.e., residues 24-34 (L1), 50-56 (L2) and 89-97 (L3) in the light chain variable domain and 31-35 (H1), 50-65 (H2) and 95-102 (H3) in the heavy chain variable domain as described by Kabat et al., Sequences of Proteins of Immunological Interest, $5^{th}$ Ed. Public Health Service, National Institutes of Health, Bethesda, Md., 1991, and/or those residues from a hypervariable loop (i.e., residues 26-32 (L1), 50-52 (L2) and 91-96 (L3) in the light chain variable domain and 26-32 (H1), 53-55 (H2) and 96-101 (H3) in the heavy chain variable domain as described by Chothia et al., *J. Mol. Biol.* 196: 901-917, 1987). However, one of skill in the art understands that the actual location of the CDR residues may vary from the projected residues described above when the sequence of the particular antibody is identified.

Framework or FR residues are those variable domain residues other than the hypervariable region residues.

Depending on the amino acid sequence of the constant domain of their heavy chains, immunoglobulins can be assigned to different classes, IgA, IgD, IgE, IgG and IgM, which may be further divided into subclasses or isotypes, e.g. IgG1, IgG2, IgG3, IgG4, IgA1 and IgA2. The subunit structures and three-dimensional configurations of different classes of immunoglobulins are well known. Different isotypes have different effector functions; for example, IgG1 and IgG3 isotypes have ADCC activity. An antibody used herein, if it comprises a constant domain, may be of any of these subclasses or isotypes.

In exemplary embodiments, an antibody or fragment thereof described herein and used in the methods can comprise a human kappa (κ) or a human lambda (λ) light chain or an amino acid sequence derived therefrom, or a human heavy chain or a sequence derived therefrom, or both heavy and light chains together in a single chain, dimeric, tetrameric or other form.

Monoclonal antibody refers to an antibody obtained from a population of substantially homogeneous antibodies. Monoclonal antibodies are generally highly specific, and may be directed against a single antigenic site, in contrast to conventional (polyclonal) antibody preparations that typically include different antibodies directed against different determinants (epitopes). In addition to their specificity, monoclonal antibodies are advantageous in that they are synthesized by the homogeneous culture, uncontaminated by other immunoglobulins with different specificities and characteristics.

Monoclonal antibodies to be used in accordance with the present disclosure may be made by the hybridoma method first described by Kohler et al., *Nature* 256:495-7, 1975, or may be made by recombinant DNA methods (see, e.g., U.S. Pat. No. 4,816,567). The monoclonal antibodies or fragments thereof may also be isolated or derived from phage antibody libraries using the techniques described in, for example, Clackson et al., *Nature* 352:624-628, 1991, and Marks et al., *J. Mol. Biol.* 222:581-597, 1991.

In the hybridoma method, a mouse or other appropriate host animal, such as a hamster or macaque monkey, is immunized to elicit lymphocytes that produce or are capable of producing antibodies that will specifically bind to the protein used for immunization (Harlow & Lane; Antibodies: A Laboratory Manual, Cold Spring Harbor Laboratory Press: Cold Spring Harbor, N.Y., 1988.

Recombinant Production of Antibodies

The present disclosure also encompasses nucleic acid molecules encoding antibodies useful in the present methods. In some embodiments, different nucleic acid molecules encode a heavy chain variable region and a light chain variable region of an antigen-specific antibody. In other embodiments, the same nucleic acid molecule encodes a heavy chain and a light chain variable regions of an antigen-specific antibody.

DNA encoding a monoclonal antibody described herein may be isolated and sequenced from a hybridoma cell secreting the antibody using conventional procedures (e.g., by using oligonucleotide probes that are capable of binding specifically to genes encoding the heavy and light chains of the monoclonal antibodies). Sequence determination will generally require isolation of at least a portion of the gene or cDNA of interest. Usually this requires cloning the DNA or, preferably, mRNA (i.e., cDNA) encoding the monoclonal antibodies. Cloning is carried out using standard techniques (see, e.g., Sambrook et al. Molecular Cloning: A Laboratory Guide, Vols 1-3, Cold Spring Harbor Press, 1989, which is incorporated herein by reference). For example, a cDNA library may be constructed by reverse transcription of polyA+mRNA, preferably membrane-associated mRNA, and the library screened using probes specific for human immunoglobulin polypeptide gene sequences. Nucleotide probe reactions and other nucleotide hybridization reactions are carried out at conditions enabling the identification of polynucleotides which hybridize to each other under specified conditions. The hybridization conditions can be calculated as described in Sambrook, et al., (Eds.), Molecular Cloning: A Laboratory Manual, Cold Spring Harbor Laboratory Press: Cold Spring Harbor, N.Y. (1989), pp. 9.47 to 9.51

In a preferred embodiment, the polymerase chain reaction (PCR) is used to amplify cDNAs (or portions of full-length cDNAs) encoding an immunoglobulin gene segment of interest (e.g., a light chain variable segment). The amplified sequences can be readily cloned into any suitable vector, e.g., expression vectors, minigene vectors, or phage display vectors. It will be appreciated that the particular method of cloning used is not critical, so long as it is possible to determine the sequence of some portion of the immunoglobulin polypeptide of interest. As used herein, an "isolated" nucleic acid molecule or "isolated" nucleic acid sequence is a nucleic acid molecule that is either (1) identified and separated from at least one contaminant nucleic acid molecule with which it is ordinarily associated in the natural source of the nucleic acid or (2) cloned, amplified, tagged, or otherwise distinguished from background nucleic acids such that the sequence of the nucleic acid of interest can be determined, is considered isolated. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

One source for RNA used for cloning and sequencing is a hybridoma produced by obtaining a B cell from the transgenic mouse and fusing the B cell to an immortal cell. Alternatively, RNA can be isolated from B cells (or whole spleen) of the immunized animal. When sources other than hybridomas are used, it may be desirable to screen for sequences encoding immunoglobulins or immunoglobulin polypeptides with specific binding characteristics. One method for such screening is the use of phage display technology. Phage display is described further herein and is also well-known in the art. See e.g., Dower et al., WO 91/17271, McCafferty et al., WO 92/01047, and Caton and Koprowski, *Proc. Natl. Acad. Sci. USA,* 87:6450-54, 1990, each of which is incorporated herein by reference. In one embodiment, cDNA from an immunized transgenic mouse (e.g., total spleen cDNA) is isolated, the polymerase chain reaction is used to amplify a cDNA sequences that encode a portion of an immunoglobulin polypeptide, e.g., CDR regions, and the amplified sequences are inserted into a phage vector. cDNAs encoding peptides of interest, e.g., variable region peptides with desired binding characteristics, are identified by standard phage display techniques such as panning.

The sequence of the amplified or cloned nucleic acid is then determined. Typically the sequence encoding an entire variable region of the immunoglobulin polypeptide is determined, however, it will sometimes by adequate to sequence only a portion of a variable region, for example, the CDR-encoding portion. Typically, the portion sequenced will be at least 30 bases in length, more often based coding for at least about one-third or at least about one-half of the length of the variable region will be sequenced.

Sequencing can be carried out on clones isolated from a cDNA library, or, when PCR is used, after subcloning the amplified sequence or by direct PCR sequencing of the amplified segment. Sequencing is carried out using standard techniques (see, e.g., Sambrook et al. Molecular Cloning: A Laboratory Guide, Vols 1-3, Cold Spring Harbor Press, 1989, and Sanger, F. et al. *Proc. Natl. Acad. Sci. USA* 74: 5463-5467, 1977, which are incorporated herein by reference). By comparing the sequence of the cloned nucleic acid with published sequences of human immunoglobulin genes and cDNAs, one of skill will readily be able to determine, depending on the region sequenced, (i) the germline segment usage of the hybridoma immunoglobulin polypeptide (including the isotype of the heavy chain) and (ii) the sequence of the heavy and light chain variable regions, including sequences resulting from N-region addition and the process of somatic mutation. One source of immunoglobulin gene sequence information is the National Center for Biotechnology Information, National Library of Medicine, National Institutes of Health, Bethesda, Md.

Once isolated, the DNA may be placed into expression vectors, which are then transfected into host cells such as *E. coli* cells, simian COS cells, human embryonic kidney 293 cells (e.g., 293E cells), Chinese hamster ovary (CHO) cells, or myeloma cells that do not otherwise produce immunoglobulin protein, to obtain the synthesis of monoclonal antibodies in the recombinant host cells. Recombinant production of antibodies is well known in the art.

Expression control sequences refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

In an alternative embodiment, the amino acid sequence of an immunoglobulin of interest may be determined by direct protein sequencing. Suitable encoding nucleotide sequences can be designed according to a universal codon table.

Amino acid sequence variants of the desired antibody may be prepared by introducing appropriate nucleotide changes into the encoding DNA, or by peptide synthesis. Such variants include, for example, deletions from, and/or insertions into and/or substitutions of, residues within the amino acid sequences of the antibodies. Any combination of deletion, insertion, and substitution is made to arrive at the final construct, provided that the final construct possesses the desired characteristics. The amino acid changes also may alter post-translational processes of the antibody, such as changing the number or position of glycosylation sites.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

The disclosure also provides isolated nucleic acid encoding antibodies contemplated herein, optionally operably linked to control sequences recognized by a host cell, vectors and host cells comprising the nucleic acids, and recombinant techniques for the production of the antibodies, which may comprise culturing the host cell so that the nucleic acid is expressed and, optionally, recovering the antibody from the host cell culture or culture medium. Various systems and methods for antibody production are reviewed by Birch & Racher *Adv. Drug Deliv. Rev.* 671-685 2006).

For recombinant production of the antibody or antibody fragment, the nucleic acid encoding it is isolated and inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more selective marker genes, an enhancer element, a promoter, and a transcription termination sequence.

Suitable host cells for cloning or expressing the DNA in the vectors herein are prokaryote, yeast, or higher eukaryote cells. Suitable prokaryotes for this purpose include eubacteria, such as Gram-negative or Gram-positive organisms, for example, Enterobacteriaceae such as *Escherichia*, e.g.,

*E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In various embodiments, manufacturing for the Fab proteins herein comprises use of CHO cells or Wacker Chemie ESETEC® technology, e.g., production of proteins using *E. coli* K12 cells (Wacker Chemie AG, Munich, Germany).

In addition to prokaryotes, eukaryotic microbes such as filamentous fungi or yeast are suitable cloning or expression hosts for antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastors* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium*, and *Aspergillus* hosts such as *A. nidulans* and *A. niger*.

Suitable host cells for the expression of glycosylated antibody are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present disclosure, particularly for transfection of *Spodoptera frugiperda* cells.

Plant cell cultures of cotton, corn, potato, soybean, *petunia*, tomato, tobacco, *lemna*, and other plant cells can also be utilized as hosts.

Examples of useful mammalian host cell lines are Chinese hamster ovary cells, including CHOK1 cells (ATCC CCL61), DXB-11, DG-44, and Chinese hamster ovary cells/-DHFR (CHO, Urlaub et al., *Proc. Natl. Acad. Sci. USA* 77: 4216 (1980)); monkey kidney CV1 line transformed by SV40 (COS-7, ATCC CRL 1651); human embryonic kidney line (293 or 293 cells subcloned for growth in suspension culture, (Graham et al., *J. Gen Virol.* 36: 59, 1977); baby hamster kidney cells (BHK, ATCC CCL 10); mouse sertoli cells (TM4, Mather, (*Biol. Reprod.* 23: 243-251, 1980); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., *Annals N.Y Acad. Sci.* 383: 44-68 (1982)); MRC 5 cells; FS4 cells; and a human hepatoma line (Hep G2).

Host cells are transformed or transfected with the above-described expression or cloning vectors for antibody production and cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful and preferred for the expression of antibodies that bind the desired antigen.

Host cells containing desired antibody or antibody fragment nucleic acid sequences may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al. *Meth. Enz.* 58: 44, 1979; Barnes et al. *Anal. Biochem.* 102: 255, 1980; U.S. Pat. Nos. 4,767,704; 4,657,866; 4,927,762; 4,560,655; or 5,122,469; WO90103430; WO 87/00195; or U.S. Pat. Re. No. 30,985, may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody or antibody fragment can be produced intracellularly, in the periplasmic space, or directly secreted into the medium, including from microbial cultures. If the antibody is produced intracellularly, as a first step, the particulate debris, either host cells or lysed fragments, is removed, for example, by centrifugation or ultrafiltration. Better et al., *Science* 240:1041-43, 1988; *ICSU Short Reports* 10:105, 1990; and *Proc. Natl. Acad. Sci. USA* 90:457-461, 1993, describe a procedure for isolating antibodies which are secreted to the periplasmic space of *E. coli*. (see also, Carter et al., *Bio/Technology* 10:163-167, 1992).

The antibody or antibody fragment composition can be purified using, for example, hydroxylapatite chromatography cation or anion exchange chromatography, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62: 1-13, 1983). Protein G is recommended for all mouse isotypes and for human γ3 (Guss et al., *EMBO J.* 5:15671575, 1986). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H 3$ domain, the Bakerbond ABX™resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Amino acid sequences of exemplary antibodies are set out in FIG. 6 and FIG. 19.

In exemplary embodiments, the method contemplates use of:

a monoclonal antibody that retains any one, two, three, four, five, or six of HCDR1, HCDR2, HCDR3, LCDR1, LCDR2, or LCDR3 of any one of SEQ ID NOs: 5-10 or SEQ ID NOs: 50-112 and SEQ ID NOs: 11-16 or SEQ ID NOs: 20-28, respectively, optionally including one or two mutations in any of such CDR(s), e.g., a conservative or non-conservative substitution;

a monoclonal antibody that retains all of HCDR1, HCDR2, HCDR3, or the heavy chain variable region of any one of SEQ ID NOs: 1, 2 or 29-49, optionally including one or two mutations in any of such CDR(s);

a monoclonal antibody that retains all of LCDR1, LCDR2, LCDR3, or the light chain variable region of any one SEQ ID NOs: 3 or 4 or 17-19, optionally including one or two mutations in any of such CDR(s), optionally further comprising to any suitable light chain constant region, e.g. a kappa or lambda light chain constant region, a human sequence thereof, or a hybrid thereof or a human consensus thereof;

a monoclonal antibody that binds to the same linear or three-dimensional epitope of INSR as an antibody comprising variable regions set out in SEQ ID NO: 1-4, 17-19 and/or 29-49, e.g., as determined through X-ray crystallography or other biophysical or biochemical techniques such as deuterium exchange mass spectrometry, alanine scanning and peptide fragment ELISA;

a monoclonal antibody that competes with an antibody comprising variable regions set out in SEQ ID NO: 1-4, 17-19 and/or 29-49 for binding to human INSR by more than about 75%, more than about 80%, or more than about 81%, 82%, 83%, 84%, 85%, 86%, 87%, 88%, 89%, 90%, 91%, 92%, 93%, 94% or 95%;

a purified preparation of a monoclonal antibody, comprising the heavy chain variable region and light chain variable regions as set forth in any one of SEQ ID NOs: 1, 2, 29-49 and 4 or 17-19;

a purified preparation of a monoclonal antibody, comprising the heavy chain variable region and light chain variable regions as set forth in any one of SEQ ID NOs: 2 and 4 or 17-19.

In some embodiments, the antibody comprises all three light chain CDRs, all three heavy chain CDRs, or all six CDRs of the light and heavy chain, paired as set forth in Table 1. In some exemplary embodiments, two light chain CDRs from an antibody may be combined with a third light chain CDR from a different antibody. Alternatively, a LCDR1 from one antibody can be combined with a LCDR2 from a different antibody and a LCDR3 from yet another antibody, particularly where the CDRs are highly homologous. Similarly, two heavy chain CDRs from an antibody may be combined with a third heavy chain CDR from a different antibody; or a HCDR1 from one antibody can be combined with a HCDR2 from a different antibody and a HCDR3 from yet another antibody, particularly where the CDRs are highly homologous.

Consensus CDRs may also be used. Any one of the consensus CDRs derived herein may be combined with two other CDRs from the same chain (e.g. heavy or light) of any of antibodies, e.g. to form a suitable heavy or light chain variable region.

In some embodiments, an antibody is provided that comprises a polypeptide having an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to the heavy chain variable region set out in SEQ ID NOs: 1, 2 or 29-49 and/or an amino acid sequence an amino acid sequence at least about 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or more identical to the light chain variable region set out in SEQ ID NOs: 3, 4 and 17-19, the antibody further comprising at least one, two, three, four, five or all of CDRH1, CDRH2, CDRH3, CDRL1, CDRL2 or CDRL3. In some embodiments, the amino acid sequence with percentage identity to the light chain variable region may comprise one, two or three of the light chain CDRs set out in SEQ ID NOs: 11-16 or SEQ ID NOs: 20-28. In other embodiments, the amino acid sequence with percentage identity to the heavy chain variable region may comprise one, two, or three of the heavy chain CDRs set out in SEQ ID NOs: 5-10 or SEQ ID NOs: 50-112.

It is contemplated that the antibodies used herein may have one, or two or more amino acid substitutions in the CDR regions of the antibody, e.g., non-conservative or conservative substitutions.

In a related embodiment, the residues of the framework are altered. The heavy chain framework regions which can be altered lie within regions designated H-FR1, H-FR2, H-FR3 and H-FR4, which surround the heavy chain CDR residues, and the residues of the light chain framework regions which can be altered lie within the regions designated L-FR1, L-FR2, L-FR3 and L-FR4, which surround the light chain CDR residues. An amino acid within the framework region may be replaced, for example, with any suitable amino acid identified in a human framework or human consensus framework.

It is further contemplated that the disclosure provides use of a purified polypeptide comprising any one of the amino acid sequences of SEQ ID NOs: 1, 2 or 29-49 fused to any one of the amino acid sequences of SEQ ID NOs: 3, 4 or 17-19, or fragments thereof that include at least a portion of SEQ ID NOs: 1, 2 or 29-49 and SEQ ID NOs: 3, 4 or 17-19, wherein the polypeptide binds insulin receptor or the insulin/insulin receptor complex.

In another aspect, the disclosure provides for use of a purified polypeptide comprising at least one CDR of a light chain variable region described herein, wherein the light chain variable region comprises an amino acid sequence at least 90% identical to the LCDR sequences set out in SEQ ID NOs: 11-16 or SEQ ID NOs: 20-28. In one embodiment, the polypeptide may be 90%, 95%, 96%, 97%, 98%, or 99% identical to any one of the LCDRs set out in SEQ ID NOs: 11-16 or SEQ ID NOs: 20-28. In a further aspect, the disclosure contemplates use of a purified polypeptide comprising at least one CDR of a heavy chain variable region described herein, wherein the heavy chain variable region comprises an amino acid sequence at least 90% identical to the HCDR sequences set out in SEQ ID NOs: 5-10 or SEQ ID NOs: 50-112. In one embodiment, the polypeptide may be 90%, 95%, 96%, 97%, 98%, or 99% identical to any one of the HCDRs set out in SEQ ID NOs: 5-10 or SEQ ID NOs: 50-112.

It is further contemplated that the CDR of the antibody heavy and light chains comprise variant amino acid sequences which may improve antibody binding affinity and are derived through, for example, affinity maturation. In one aspect it is contemplated that an antibody used herein comprises a heavy chain HCDR1 sequence having about 50%, 60%, 70%, 80%, or 90% identity to a HCDR1 of a parent antibody sequence set out in SEQ ID NOs: 1, 2 or 29-49. In one aspect it is contemplated that an antibody used herein comprises a heavy chain HCDR2 sequence having about 50%, 60%, 70%, 80%, or 90% identity to a HCDR2 of a parent antibody sequence set out in SEQ ID NOs: 1, 2 or 29-49. In a related aspect it is contemplated that an antibody used herein comprises a heavy chain HCDR3 sequence having about 50%, 60%, 70%, 80%, or 90% identity to a HCDR3 of a parent antibody sequence set out in SEQ ID NOs: 1, 2 or 29-49.

In one aspect it is contemplated that an antibody used herein comprises a light chain LCDR1 sequence having about 50%, 60%, 70%, 80%, or 90% identity to a LCDR1 of a parent antibody sequence set out in SEQ ID NOs: 3, 4 or 7-19. In one aspect it is contemplated that an antibody used herein comprises a heavy chain LCDR2 sequence having about 50%, 60%, 70%, 80%, or 90% identity to a LCDR2 of a parent antibody sequence set out in SEQ ID NOs: 3, 4 or 7-19. In a related aspect it is contemplated that an antibody used herein comprises a heavy chain LCDR3 sequence having about 50%, 60%, 70%, 80%, or 90% identity to a LCDR3 of a parent antibody sequence set out in SEQ ID NOs: 3, 4 or 7-19.

In one embodiment, the disclosure contemplates use of antigen-binding compounds, including functional fragments, having a variable region amino acid sequence set forth in any one of SEQ ID NOs: 1-4, 17-19 and/or 29-49. In a related embodiment, an aforementioned antigen binding compound is selected from the group consisting of a fully assembled tetrameric antibody, a polyclonal antibody, a monoclonal antibody including a HUMAN ENGINEERED™ antibody; a humanized antibody; a human antibody; a chimeric antibody; a multispecific antibody, an antibody fragment, Fab, F(ab')$_2$; Fv; scFv or single-chain antibody fragment; a diabody; triabody, tetrabody, minibody, linear antibody; chelating recombinant antibody, a tribody or bibody, an intrabody, a nanobody, a small modular immunopharmaceutical (SMIP), a binding-domain immunoglobulin fusion protein, a camelized antibody, a V$_{HH}$ containing antibody, or a variant or derivative of any one of these antibodies, that comprise one or more CDR sequences of the antibody and exhibit the desired biological activity. The antigen binding compounds preferably retain binding affinity of $10^{-5}$, $10^{-6}$, $10^{-7}$, $10^{-8}$, $10^{-9}$, $10^{-10}$, $10^{-11}$, $10^{-12}$ M or less as measured by surface plasmon resonance.

In one aspect, the antibodies useful in the present methods comprise a heavy chain variable region or light chain variable region as set out in amino acid sequences SEQ ID NO: 2 and SEQ ID NO: 4, respectively, optionally as paired in Table 1.

TABLE 1

| Antibody | Heavy Chain Variable SEQ ID NO: | HCDR1, HCDR2, HCDR3 SEQ ID NO: | Light Chain Variable SEQ ID NO: | LCDR1, LCDR2, LCDR3 SEQ ID NO: |
|---|---|---|---|---|
| XPA.15.247 | 1 | 5-7 | 3 | 11-13 |
| XPA.15.247.2.018 | 2 | 8-10 | 4 | 14-16 |
| XPA.15.247.014 | 2 | | 17 | 20-22 |
| XPA.15.247.011 | 2 | | 18 | 23-25 |
| XPA.15.247.019 | 1 | | 19 | 26-28 |
| RHF.15.05896.004 | 29 | 50-52 | | |
| RHF.15.05896.006 | 30 | 53-55 | | |
| RHF.15.05896.012 | 31 | 56-58 | | |
| RHF.15.05896.015 | 32 | 59-61 | | |
| RHF.15.05896.020 | 33 | 62-64 | | |
| RHF.15.05896.022 | 34 | 65-67 | | |
| RHF.15.05896.028 | 35 | 68-70 | | |
| RHF.15.05896.032 | 36 | 71-73 | | |
| RHF.15.05896.036 | 37 | 74-76 | | |
| RHF.15.05896.040 | 38 | 77-79 | | |
| RHF.15.05896.044 | 39 | 80-82 | | |
| RHF.15.05896.048 | 40 | 83-85 | | |
| RHF.15.05896.052 | 41 | 86-88 | | |
| RHF.15.05896.056 | 42 | 89-91 | | |
| RHF.15.05896.059 | 43 | 92-94 | | |
| RHF.15.05896.064 | 44 | 95-97 | | |
| RHF.15.05896.068 | 45 | 98-100 | | |
| RHF.15.05896.072 | 46 | 101-103 | | |
| RHF.15.05896.075 | 47 | 104-106 | | |
| RHF.15.05896.079 | 48 | 107-109 | | |
| RHF.15.05896.084 | 49 | 110-112 | | |

It is further contemplated that the antibodies may comprise all or part of the antibodies set out in the above amino acid sequences. In one embodiment, the antibodies comprise at least one of CDR1, CDR2, or CDR3 of the heavy chain of SEQ ID NOs: 1, 2 or 29-49, or at least one of CDR1, CDR2 or CDR3 of the light chain of SEQ ID NOs: 3 or 4 or 17-19, optionally as paired in Table 1.

In one embodiment, the heavy chain comprises an amino acid sequence identified as a heavy chain CDR3 sequence. Such a "heavy chain CDR3 sequence" (HCDR3) includes an amino acid sequence identified as a heavy chain CDR3 sequence set out in SEQ ID NOs: 7, 10, 52, 55, 58, 61, 64, 67, 70, 73, 76, 79, 82, 85, 88, 91, 94, 97, 100, 103, 106, 109 and 112. Alternatively, the HCDR3 sequence comprises an amino acid sequence that contains one or more amino acid changes compared to any HCDR3 amino acid sequence set out in SEQ ID NOs: 7, 10, 52, 55, 58, 61, 64, 67, 70, 73, 76, 79, 82, 85, 88, 91, 94, 97, 100, 103, 106, 109 and 112, i.e., a substitution, insertion or deletion. Preferable substitutions include a substitution to an amino acid at the corresponding position within another HCDR3 herein. Alternatively, the HCDR3 sequence may comprise a consensus amino acid sequence of the HCDR3 described herein.

The heavy chain comprising a HCDR3 sequence of the antibody described above may further comprise a "heavy chain CDR1 sequence", which includes any of the amino acid sequences identified as a heavy chain CDR1 in SEQ ID NOs: 5, 8, 50, 53, 56, 59, 62, 65, 68, 71, 74, 77, 80, 83, 86, 89, 92, 95, 98, 101, 104, 107 and 110 amino acid sequences that contain one or more amino acid changes compared to any heavy chain CDR1 identified in SEQ ID NOs: 5, 8, 50, 53, 56, 59, 62, 65, 68, 71, 74, 77, 80, 83, 86, 89, 92, 95, 98, 101, 104, 107 and 110, preferably a substitution to an amino acid at the corresponding position within another heavy chain CDR1 herein, or a consensus sequence of heavy chain CDR1 described herein.

Alternatively, the heavy chain comprising a HCDR3 sequence of the antibody described above may further comprise a "heavy chain CDR2 sequence" (HCDR2), which includes any of the amino acid sequences identified as an HCDR2 in SEQ ID NOs: 6, 9, 51, 54, 57, 60, 63, 66, 69, 72, 75, 78, 81, 84, 87, 90, 93, 96, 99, 102, 105, 108 and 111 amino acid sequences that contain one or more amino acid changes compared to any HCDR2 identified in SEQ ID NOs: 6, 9, 51, 54, 57, 60, 63, 66, 69, 72, 75, 78, 81, 84, 87, 90, 93, 96, 99, 102, 105, 108 and 111, or a consensus sequence of heavy chain CDR2 described herein.

The heavy chain comprising a heavy chain CDR3 sequence described above may also comprise both (a) a heavy chain CDR1 sequence described above and (b) a heavy chain CDR2 sequence described above.

One aspect of the disclosure contemplates use of an antibody that binds target antigen comprising a heavy chain that comprises any one, two, and/or three of the heavy chain CDR sequences described herein.

Any of the heavy chain CDR sequences described above may also include amino acids added to either end of the CDRs. Preparation of variants and derivatives of antibodies and antigen-binding compounds, including affinity maturation or preparation of variants or derivatives containing amino acid analogs, is described in further detail herein. Exemplary variants include those containing a conservative or non-conservative substitution of a corresponding amino acid within the amino acid sequence, or a replacement of an amino acid with a corresponding amino acid of a human antibody sequence.

Antibodies comprising any one of the heavy chains described above may further comprise a light chain, preferably a light chain that binds to target antigen, and most preferably a light chain comprising light chain CDR sequences described below.

Another aspect of the disclosure provides use of an antibody that binds target antigen comprising a light chain that comprises any one, two, and/or three of the light chain CDR sequences described below.

Preferably the light chain comprises an amino acid sequence identified as a light chain CDR3 sequence. Such a "light chain CDR3 sequence" (LCDR3) includes an amino acid sequence identified as a light chain CDR3 sequence set out in SEQ ID NOs: 13, 16, 22, 25 or 28. Alternatively, the light chain CDR3 sequence comprises an amino acid sequence that contains one or more amino acid changes compared to any light chain CDR3 amino acid sequence set out in SEQ ID NOs: 13, 16, 22, 25 or 28 i.e., a substitution, insertion or deletion or a consensus sequence of light chain CDR3 described below.

The light chain comprising a light chain CDR3 sequence described above may further comprise a "light chain CDR1 sequence", which includes any of the amino acid sequences identified as a light chain CDR1 in SEQ ID NOs: 11, 14, 20, 23 or 26, amino acid sequences that contain one or more amino acid changes compared to any light chain CDR1 identified in SEQ ID NOs: 11, 14, 20, 23 or 26, preferably a substitution to an amino acid at the corresponding position within another light chain CDR1 herein, or a consensus sequence of light chain CDR1 described herein.

Alternatively, the light chain comprising a light chain CDR3 sequence described above may further comprise a "light chain CDR2 sequence", which includes any of the amino acid sequences identified as a light chain CDR2 in SEQ ID NOs: 12, 15, 21, 24 or 27, amino acid sequences that contain one or more amino acid changes compared to any light chain CDR2 of SEQ ID NOs: 12, 15, 21, 24 or 27, preferably a substitution to an amino acid at the corresponding position within another light chain CDR2 of SEQ ID NOs 12, 15, 21, 24 or 27, or a consensus sequence of light chain CDR2.

In a related aspect, the disclosure contemplates use of a purified polypeptide comprising at least one HCDR of SEQ ID NOs: 1, 2 or 29-49 or LCDR of SEQ ID NOs: 3, 4 or 17-19, wherein the framework regions of the heavy chain variable region and the framework regions of the light chain variable region comprise framework regions from a human antibody. In another embodiment, the framework regions of the heavy chain variable region and the framework regions of the light chain variable region are chemically altered by amino acid substitution to be more homologous to a human antibody sequence. For example, within each heavy chain framework region (H-FR1-4) it is contemplated that at least one, at least two, at least three, at least four, at least five, or at least six native framework region residues of the murine heavy chain variable region have been altered by amino acid substitution, and wherein within each light chain framework region (L-FR1-4), at least one, at least two, at least three, at least four, at least five or at least six native framework residues of the murine light chain variable region have been altered by amino acid substitution.

The light chain comprising a light chain CDR3 sequence described above may also comprise both (a) a light chain CDR1 sequence described above and (b) a light chain CDR2 sequence described above.

Antibodies comprising any one of the light chain variable regions described above may further comprise a heavy chain variable region, optionally paired as described in Table 1, preferably a heavy chain variable region that binds to target antigen, and most preferably a heavy chain variable region comprising heavy chain CDR sequences described above.

In a related embodiment, the negative modulator antibody includes, but is not limited to the following antibody fragments: XPA.15.247 (SEQ ID NOs: 1 and 3), and XPA.15.247.2.018 (SEQ ID NOs: 2 and 4). Also contemplated are antibodies having other combinations of heavy and light chains from Table 1.

In a further aspect, the antibody is an antibody that competes with any of the antibodies described herein for binding to the insulin receptor or insulin/insulin receptor complex. In certain embodiments, the antibody exhibits partial competition. In a related embodiment, partial competition is competition of about 30% to 70%, about 30% to 80%, or about 30%, 35%, 40%, 45%, 50%, 55%, 60%, 65%, 70%, 75%, or 80%. In some embodiments, the antibody exhibits complete competition. In one embodiment, complete competition is competition of greater than 70%, 75%, 80%, 85%, 90%, 95% or 100%. Exemplary assays for measuring antibody competition include, but are not limited to, receptor loading assays and epitope binning assays as described in the art.

Other exemplary antibodies that bind the insulin receptor include those reported in Soos et al, *Biochem. J.* 235: 199-208, 1986; Taylor et al, *Biochem. J.* 242: 123-129, 1987; Prigent et al, *J. Biol. Chem.* 265(17):9970-9977, 1990; Brindle et al, *Biochem. J.* 268: 615-620, 1990; Steele-Perkins and Roth, *J. Biol. Chem.* 265(16): 9458-9463, 1990; McKern et al, *Nature* 443(14): 218-221; Boado et al, *Biotech and BioEng.* 96(2): 381-391; WO04/050016; Roth et al, *Proc. Natl. Acad. Sci. USA* 79: 7312-7316, 1982; Morgan et al, *Proc. Natl. Acad. Sci. USA* 83: 328-332, 1986; Lebrun et al, *J. Biol. Chem.* 268(15): 11272-11277, 1993; Forsayeth et al, *Proc. Natl. Acad. Sci. USA* 84: 3448-3451, 1987; Forsayeth et al, *J. Biol. Chem.* 262(9): 4134-4140, Goodman et al, *J. Receptor Res.* 14(6-8), 381-398, 1994; Ganderton et al,

*Biochem J.* 288: 195-205, 1992; Spasov et al, *Bull. of Exp. Biol. and Med.* 144(1): 46-48, 2007; and EP 2 036 574 A1.

Antibody Fragments

Antibody fragments comprise a portion of an intact full length antibody, preferably an antigen binding or variable region of the intact antibody. Examples of antibody fragments include Fab, Fab', F(ab')$_2$, Fcab and Fv fragments; diabodies; linear antibodies; single-chain antibody molecules (e.g., scFv); multispecific antibody fragments such as bispecfic, trispecific, etc. antibodies (e.g., diabodies, triabodies, tetrabodies); minibody; chelating recombinant antibody; tribodies or bibodies; intrabodies; nanobodies; small modular immunopharmaceuticals (SMIP), binding-domain immunoglobulin fusion proteins; camelized antibodies; V$_{HH}$ containing antibodies; and other polypeptides formed from antibody fragments. See, for example, Holliger & Hudson, *Nat. Biotech.* 23(9) 1126-36, 2005; Eyer & Hruska (Veterinarni Medicina 57: 439-513, 2012).

Papain digestion of antibodies produces two identical antigen-binding fragments, called "Fab" fragments, monovalent fragments consisting of the V$_L$, V$_H$, C$_L$ and C$_H$ domains each with a single antigen-binding site, and a residual "Fc" fragment, whose name reflects its ability to crystallize readily. Pepsin treatment yields a F(ab')$_2$ fragment, a bivalent fragment comprising two Fab fragments linked by a disulfide bridge at the hinge region, that has two "Single-chain Fv" or "scFv" antibody fragments comprise the V$_H$ and V$_L$ domains of antibody, wherein these domains are present in a single polypeptide chain. Preferably, the Fv polypeptide further comprises a polypeptide linker between the V$_H$ and V$_L$ domains that enables the Fv to form the desired structure for antigen binding, resulting in a single-chain antibody (scFv), in which a V$_L$ and V$_H$ region are paired to form a monovalent molecule via a synthetic linker that enables them to be made as a single protein chain (Bird et al., *Science* 242:423-426, 1988, and Huston et al., *Proc. Natl. Acad. Sci. USA* 85:5879-5883, 1988). For a review of scFv, see Pluckthun, in The Pharmacology of Monoclonal Antibodies, vol. 1 13, Rosenburg and Moore eds., Springer-Verlag, New York, pp. 269-315, 1994. An Fd fragment consists of the V$_H$ and C$_H$1 domains.

Antibody fragments, such as Fab fragments can also be made using recombinant techniques known in the art and described herein. Exemplary methods for making recombinant antibody fragment in mammalian, bacteria or other cells lines are disclosed in Frenzel et al., *Front Immunol.* 4: 217, 2013, incorporated herein by reference.

Additional antibody fragments include a domain antibody (dAb) fragment (Ward et al., *Nature* 341:544-546, 1989) which consists of a V$_H$ domain. Diabodies are bivalent antibodies in which V$_H$ and V$_L$ domains are expressed on a single polypeptide chain, but using a linker that is too short to allow for pairing between the two domains on the same chain, thereby forcing the domains to pair with complementary domains of another chain and creating two antigen binding sites (see e.g., EP 404,097; WO 93/11161; Holliger et al., *Proc. Natl. Acad. Sci. USA* 90:6444-6448, 1993, and Poljak et al., *Structure* 2:1121-1123, 1994). Diabodies can be bispecific or monospecific.

Functional heavy-chain antibodies devoid of light chains are naturally occurring in nurse sharks (Greenberg et al., *Nature* 374:168-73, 1995), wobbegong sharks (Nuttall et al., *Mol Immunol.* 38:313-26, 2001) and Camelidae (Hamers-Casterman et al., *Nature* 363: 446-8, 1993; Nguyen et al., *J. Mol. Biol.* 275: 413, 1998), such as camels, dromedaries, alpacas and llamas. The antigen-binding site is reduced to a single domain, the VHH domain, in these animals. These antibodies form antigen-binding regions using only heavy chain variable region, i.e., these functional antibodies are homodimers of heavy chains only having the structure H$_2$L$_2$ (referred to as "heavy-chain antibodies" or "HCAbs"). Camelid V$_{HH}$ reportedly recombines with IgG2 and IgG3 constant regions that contain hinge, CH2, and CH3 domains and lack a CH1 domain (Hamers-Casterman et al., supra). For example, llama IgG1 is a conventional (H$_2$L$_2$) antibody isotype in which V$_H$ recombines with a constant region that contains hinge, CH1, CH2 and CH3 domains, whereas the llama IgG2 and IgG3 are heavy chain-only isotypes that lack CH1 domains and that contain no light chains. Camelid V$_{HH}$ domains have been found to bind to antigen with high affinity (Desmyter et al., *J. Biol. Chem.* 276:26285-90, 2001) and possess high stability in solution (Ewert et al., *Biochemistry* 41:3628-36, 2002). Classical V$_H$-only fragments are difficult to produce in soluble form, but improvements in solubility and specific binding can be obtained when framework residues are altered to be more VH$_H$-like. (See, e.g., Reichman, et al., *J Immunol Methods* 231:25-38, 1999) Methods for generating antibodies having camelid heavy chains are described in, for example, in U.S. Patent Publication Nos. 20050136049 and 20050037421.

The variable domain of an antibody heavy-chain, a fully functional antigen-binding fragment with a molecular mass of only 15 kDa, is referred to as a nanobody (Cortez-Retamozo et al., *Cancer Research* 64:2853-57, 2004). A nanobody library may be generated from an immunized dromedary as described in Conrath et al., (*Antimicrob Agents Chemother* 45: 2807-12, 2001) or using recombinant methods as described in Revets et al, *Expert Opin. Biol. Ther.* 5(1): 111-24, 2005.

Production of bispecific Fab-scFv ("bibody") and trispecific Fab-(scFv)(2) ("tribody") are described in Schoonjans et al. (*J Immunol.* 165:7050-57, 2000) and Willems et al. (*J Chromatogr B Analyt Technol Biomed Life Sci.* 786:161-76, 2003). For bibodies or tribodies, a scFv molecule is fused to one or both of the VL-CL (L) and VH-CH$_1$ (Fd) chains, e.g., to produce a tribody two scFvs are fused to C-term of Fab while in a bibody one scFv is fused to C-term of Fab. Additional Fab-based bispecific formats are described in Wu et al (mAbs 7: 470-482, 2015).

A "minibody" consisting of scFv fused to CH3 via a peptide linker (hingeless) or via an IgG hinge has been described in Olafsen, et al., *Protein Eng Des Sel.* 17(4):315-23, 2004.

Intrabodies are single chain antibodies which demonstrate intracellular expression and can manipulate intracellular protein function (Biocca, et al., *EMBO J.* 9:101-108, 1990; Colby et al., *Proc Natl Acad Sci USA.* 101:17616-21, 2004). Intrabodies, which comprise cell signal sequences which retain the antibody construct in intracellular regions, may be produced as described in Mhashilkar et al. *EMBO J* 14:1542-51, 1995, and Wheeler et al. *FASEB J.* 17:1733-5. 2003. Transbodies are cell-permeable antibodies in which a protein transduction domain (PTD) is fused with single chain variable fragment (scFv) antibodies Heng et al. *Med Hypotheses.* 64:1105-8, 2005.

Further contemplated are antibodies that are SMIPs or binding domain immunoglobulin fusion proteins specific for an antigen. These constructs are single-chain polypeptides comprising antigen binding domains fused to immunoglobulin domains necessary to carry out antibody effector functions. See e.g., WO03/041600, U.S. Patent publication 20030133939 and US Patent Publication 20030118592.

One or more CDRs may be incorporated into a molecule either covalently or noncovalently to make it an immunoadhesin. An immunoadhesin may incorporate the CDR(s) as part of a larger polypeptide chain, may covalently link the CDR(s) to another polypeptide chain, or may incorporate the CDR(s) noncovalently. The CDRs permit the immunoadhesin to specifically bind to a particular antigen of interest.

In yet another embodiment, the antibody or antigen-binding compound comprises a constant region and one or more heavy and light chain variable framework regions of a human antibody sequence. In a related embodiment, the antibody comprises a modified or unmodified constant region of a human IgG1, IgG2, IgG3 or IgG4.

Alternatively, antibody fragments may be fused to a protein scaffold. Libraries of protein scaffolds include, but are not limited to, Adnectins, Affibodies, Anticalins, DARPins, engineered Kunitz-type inhibitors, tetranectins, A-domain proteins, lipocalins, repeat proteins such as ankyrin repeat proteins, immunity proteins, α2p8 peptide, insect defensin A, PDZ domains, charybdotoxins, PHD fingers, TEM-1 β-lactamase, fibronectin type III domains, CTLA-4, T-cell resptors, knottins, neocarzinostatin, carbohydrate binding module 4-2, green fluorescent protein, thioredoxin (Gebauer & Skerra, *Curr. Opin. Chem. Biol.* 13:245-55, 2009; Gill & Damle, *Curr. Opin. Biotech* 17: 653-58, 2006; Hosse et al, *Protein Sci.* 15:14-27, 2006; Skerra, *Curr. Opin. Biotech* 18: 295-304, 2007).

Thus, a variety of compositions comprising one, two, and/or three CDRs of a heavy chain variable region or a light chain variable region of an antibody may be generated by techniques known in the art.

Chimeric and Humanized Antibodies

Because chimeric or humanized antibodies are less immunogenic in humans than the parental mouse monoclonal antibodies, they can be used for the treatment of humans with far less risk of anaphylaxis.

Chimeric monoclonal antibodies, in which the variable Ig domains of a mouse monoclonal antibody are fused to human constant Ig domains, can be generated using standard procedures known in the art (See Morrison et al., *Proc. Natl. Acad. Sci. USA* 81, 6841-6855, 1984; and, Boulianne et al, *Nature* 312, 643-646, 1984). Although some chimeric monoclonal antibodies have proved less immunogenic in humans, the mouse variable Ig domains can still lead to a significant human anti-mouse response.

Humanized antibodies may be achieved by a variety of methods including, for example: (1) grafting the non-human complementarity determining regions (CDRs) onto a human framework and constant region (a process referred to in the art as humanizing through "CDR grafting") (2) transplanting the entire non-human variable domains, but "cloaking" them with a human-like surface by replacement of surface residues (a process referred to in the art as "veneering"), or, alternatively, (3) substituting human amino acids at positions determined to be unlikely to adversely affect either antigen binding or protein folding, but likely to reduce immunogenicity in a human environment (a process referred to in the art as HUMAN ENGINEERING™. In the present disclosure, humanized antibodies will include both "humanized", "veneered" and "HUMAN ENGINEERED™" antibodies. These methods are disclosed in, e.g., Jones et al., *Nature* 321:522 525, 1986; Morrison et al., *Proc. Natl. Acad. Sci., U.S.A.,* 81:6851-6855, 1984; Morrison and Oi, *Adv. Immunol.,* 44:65-92, 1988; Verhoeyer et al., *Science* 239: 1534-1536, 1988; Padlan, *Molec. Immun.* 28:489-498, 1991; Padlan, *Molec. Immunol.* 31:169-217, 1994; Kettleborough et al., *Protein Eng.* 4:773-783, 1991; Studnicka et al. U.S. Pat. No. 5,766,886; Studnicka et al., *Protein Eng* 7: 805-814, 1994, each of which is incorporated herein by reference.

CDR grafting techniques are known in the field, see for example, Riechmann, et al. 1988 *Nature* 332:323-27). Additional antibody humanization methods are reviewed by Safdan et al., *Biotech. Gen. Eng. Rev.* 29: 175-86, 2013.

Human Antibodies from Transgenic Animals

Human antibodies to antigen can also be produced using transgenic animals that have no endogenous immunoglobulin production and are engineered to contain human immunoglobulin loci. For example, WO 98/24893 discloses transgenic animals having a human Ig locus wherein the animals do not produce functional endogenous immunoglobulins due to the inactivation of endogenous heavy and light chain loci. WO 91/00906 also discloses transgenic non-primate mammalian hosts capable of mounting an immune response to an immunogen, wherein the antibodies have primate constant and/or variable regions, and wherein the endogenous immunoglobulin encoding loci are substituted or inactivated. WO 96/30498 and U.S. Pat. No. 6,091,001 disclose the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions. See also, U.S. Pat. Nos. 6,114,598; 6,657,103; and 6,833,268.

Using a transgenic animal described above, an immune response can be produced to a selected antigen, and antibody producing cells can be removed from the animal and used to produce hybridomas that secrete human monoclonal antibodies. Immunization protocols, adjuvants, and the like are known in the art, and are used in immunization of, for example, a transgenic mouse as described in WO 96/33735. This publication discloses monoclonal antibodies against a variety of antigens including IL-6, IL-8, TNFa, human CD4, L selectin, gp39, and tetanus toxin. The monoclonal antibodies can be tested for the ability to inhibit or neutralize the biological activity or physiological effect of the corresponding protein. WO 96/33735 discloses that monoclonal antibodies against IL-8, derived from immune cells of transgenic mice immunized with IL-8, blocked IL-8 induced functions of neutrophils. Human monoclonal antibodies with specificity for the antigen used to immunize transgenic animals are also disclosed in WO 96/34096 and U.S. Patent Publication No. 20030194404; and U.S. Patent Publication No. 20030031667.

Additional transgenic animals useful to make monoclonal antibodies include the Medarex HuMAb-MOUSE®, described in U.S. Pat. No. 5,770,429 and Fishwild, et al., *Nat. Biotechnol.* 14:845-851, 1996, which contains gene sequences from unrearranged human antibody genes that code for the heavy and light chains of human antibodies. Immunization of a HuMAb-MOUSE® enables the production of fully human monoclonal antibodies to the antigen.

Also, Ishida et al., *Cloning Stem Cells.* 4:91-102, 2002, describes the TransChromo Mouse (TCMOUSE™) which comprises megabase-sized segments of human DNA and which incorporates the entire human immunoglobulin (hIg) loci. The TCMOUSE™ has a fully diverse repertoire of hIgs, including all the subclasses of IgGs (IgG1-G4). Immunization of the TCMOUSE™ with various human antigens produces antibody responses comprising human antibodies.

See also Jakobovits et al., *Proc. Natl. Acad. Sci. USA,* 90:2551, 1993; Jakobovits et al., *Nature,* 362:255-258, 1993; Bruggermann et al., *Year in Immunol.*, 7:33, 1993; Green et al., *Current Drug Discovery Technologies*, 11: 74-84, 2014; and U.S. Pat. No. 5,591,669, U.S. Pat. No. 5,589,369, U.S. Pat. No. 5,545,807; and U.S. Patent Publication No. 20020199213. U.S. Patent Publication No. 20030092125 describes methods for biasing the immune response of an animal to the desired epitope. Human antibodies may also be generated by in vitro activated B cells (see U.S. Pat. Nos. 5,567,610 and 5,229,275).

Human Antibodies from Display Technology

The development of technologies for making repertoires of recombinant human antibody genes, and the display of the encoded antibody fragments on the surface of filamentous bacteriophage, has provided a means for making human antibodies directly. The antibodies produced by phage display technology are produced as antigen binding fragments-usually Fv or Fab fragments-in bacteria and thus lack effector functions. Effector functions can be introduced by one of two strategies: The fragments can be engineered either into complete antibodies for expression in mammalian cells, or into bispecific antibody fragments with a second binding site capable of triggering an effector function.

Methods are available for producing antigen-specific antibody or antigen-binding portion thereof comprising the steps of synthesizing a library of human antibodies on phage, screening the library with antigen or a portion thereof, isolating phage that bind antigen, and obtaining the antibody from the phage. By way of example, one method for preparing the library of antibodies for use in phage display techniques comprises the steps of immunizing a non-human animal comprising human immunoglobulin loci with antigen or an antigenic portion thereof to create an immune response, extracting antibody producing cells from the immunized animal; isolating RNA from the extracted cells, reverse transcribing the RNA to produce cDNA, amplifying the cDNA using a primer, and inserting the cDNA into a phage display vector such that antibodies are expressed on the phage. Recombinant antigen-specific antibodies useful herein may be obtained in this way. In another example, antibody producing cells can be extracted from non-immunized animals, RNA isolated from the extracted cells and reverse transcribed to produce cDNA, which is amplified using a primer, and inserted into a phage display vector such that antibodies are expressed on the phage. Phage-display processes mimic immune selection through the display of antibody repertoires on the surface of filamentous bacteriophage, and subsequent selection of phage by their binding to an antigen of choice. One such technique is described in WO 99/10494, which describes the isolation of high affinity and functional agonistic antibodies for MPL and msk receptors using such an approach. Antibodies can be isolated by screening of a recombinant combinatorial antibody library, for example a scFv or Fab phage display library, prepared using human $V_L$ and $V_H$ cDNAs prepared from mRNA derived from human lymphocytes. Methodologies for preparing and screening such libraries are known in the art. See e.g., U.S. Pat. No. 5,969,108. There are commercially available kits for generating phage display libraries (e.g., the Pharmacia Recombinant Phage Antibody System, catalog no. 27-9400-01; and the Stratagene SurfZAP™ phage display kit, catalog no. 240612). There are also other methods and reagents that can be used in generating and screening antibody display libraries (see, e.g., Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. *Bio/Technology* 9:1370-1372, 1991; Hay et al. *Hum. Antibod. Hybridomas* 3:81-85, 1992; Huse et al. *Science* 246:1275-1281, 1989; McCafferty et al., *Nature* 348:552-554, 1990; Griffiths et al. *EMBO J* 12:725-734, 1993; Hawkins et al. *J. Mol. Biol.* 226:889-896, 1992; Clackson et al. *Nature* 352:624-628, 1991; Gram et al. *Proc. Natl. Acad. Sci. USA* 89:3576-3580, 1992; Garrad et al. *Bio/Technology* 9:1373-1377, 1991; Hoogenboom et al. *Nuc Acid Res* 19:4133-4137, 1991; Barbas et al. *Proc. Natl. Acad. Sci. USA* 88:7978-7982, 1991, and Omidfar & Daneshpour, Exp. Op. Drug Disc. 10: 651-669, 2015.

In one embodiment, to isolate human antibodies specific for an antigen, with the desired binding characteristics, a human $V_H$ and $V_L$ library are screened to select for antibody fragments having the desired specificity. The antibody libraries used in this method may be scFv libraries prepared and screened as described herein and in the art (McCafferty et al., PCT Publication No. WO 92/01047, McCafferty et al., *Nature* 348:552-554, 1990; Griffiths et al., *EMBO J* 12:725-734, 1993 and Schwimmer et al, *J. Immunol. Methods* 391: 60-71, 2013). The antibody libraries preferably are screened using the antigen.

Alternatively, the Fd fragment ($V_H$-$C_H1$) and light chain ($V_L$-$C_L$) of antibodies are separately cloned by PCR and recombined randomly in combinatorial phage display libraries, which can then be selected for binding to a particular antigen. The Fab fragments are expressed on the phage surface, i.e., physically linked to the genes that encode them. Thus, selection of Fab by antigen binding co-selects for the Fab encoding sequences, which can be amplified subsequently. Through several rounds of antigen binding and re-amplification, a procedure termed panning, Fab specific for the antigen are enriched and finally isolated.

In 1994, an approach for the humanization of antibodies, called "guided selection", was described. Guided selection utilizes the power of the phage display technique for the humanization of mouse monoclonal antibody (See Jespers, L. S., et al., *Bio/Technology* 12, 899-903, 1994). For this, the Fd fragment of the mouse monoclonal antibody can be displayed in combination with a human light chain library, and the resulting hybrid Fab library may then be selected with antigen. The mouse Fd fragment thereby provides a template to guide the selection. Subsequently, the selected human light chains are combined with a human Fd fragment library. Selection of the resulting library yields entirely human Fab.

A variety of procedures have been described for deriving human antibodies from phage-display libraries (See, for example, Hoogenboom et al., *J. Mol. Biol.*, 227:381, 1991; Marks et al., *J. Mol. Biol*, 222:581-597, 1991; U.S. Pat. Nos. 5,565,332 and 5,573,905; Clackson, T., and Wells, J. A., *TIBTECH* 12, 173-184, 1994). In particular, in vitro selection and evolution of antibodies derived from phage display libraries has become a powerful tool (See Burton, D. R., and Barbas III, C. F., *Adv. Immunol.* 57, 191-280, 1994; Winter, G., et al., *Annu. Rev. Immunol.* 12, 433-455, 1994; U.S. Patent Publication No. 20020004215 and WO 92/01047; U.S. Patent Publication no. 20030190317; and U.S. Pat. Nos. 6,054,287 and 5,877,293.

Fv fragments are displayed on the surface of phage, by the association of one chain expressed as a phage protein fusion (e.g., with M13 gene III) with the complementary chain expressed as a soluble fragment. It is contemplated that the phage may be a filamentous phage such as one of the class I phages: fd, M13, f1, If1, Ike, ZJ/Z, Ff and one of the class II phages Xf, Pf1 and Pf3. The phage may be M13, or fd or a derivative thereof.

Once initial human $V_L$ and $V_H$ segments are selected, "mix and match" experiments, in which different pairings of the selected $V_L$ and $V_H$ segments are screened for antigen binding to select preferred $V_L/V_H$ pair combinations (See, for example, Kang et al (1991) *Proc. Natl. Acad. Sci.* 88: 11120-11123). Additionally, to further improve the quality of the antibody, the $V_L$ and $V_H$ segments of the preferred $V_L/V_H$ pair(s) can be randomly mutated, preferably within the any of the CDR1, CDR2 or CDR3 region of $V_H$ and/or $V_L$, in a process analogous to the in vivo somatic mutation process responsible for affinity maturation of antibodies during a natural immune response. This in vitro affinity maturation can be accomplished by amplifying $V_L$ and $V_H$ regions using PCR primers complimentary to the $V_H$ CDR1, CDR2, and CDR3, or $V_L$ CDR1, CDR2, and CDR3, respectively, which primers have been "spiked" with a random mixture of the four nucleotide bases at certain positions such that the resultant PCR products encode $V_L$ and $V_H$ segments into which random mutations have been introduced into the $V_H$ and/or $V_L$ CDR3 regions. These randomly mutated $V_L$ and $V_H$ segments can be rescreened for binding to antigen.

Following screening and isolation of a target-specific antibody from a recombinant immunoglobulin display library, nucleic acid encoding the selected antibody can be recovered from the display package (e.g., from the phage genome) and subcloned into other expression vectors by standard recombinant DNA techniques. If desired, the nucleic acid can be further manipulated to create other antibody forms, as described below. To express a recombinant human antibody isolated by screening of a combinatorial library, the DNA encoding the antibody is cloned into a recombinant expression vector and introduced into a mammalian host cell, as described herein.

It is contemplated that the phage display method may be carried out in a mutator strain of bacteria or host cell. A mutator strain is a host cell which has a genetic defect which causes DNA replicated within it to be mutated with respect to its parent DNA. Example mutator strains are NR9046mutD5 and NR9046 mut T1.

It is also contemplated that the phage display method may be carried out using a helper phage. This is a phage which is used to infect cells containing a defective phage genome and which functions to complement the defect. The defective phage genome can be a phagemid or a phage with some function encoding gene sequences removed. Examples of helper phages are M13K07, M13K07 gene III no. 3, hyperphage; and phage displaying or encoding a binding molecule fused to a capsid protein.

Antibodies may also be generated via phage display screening methods using the hierarchical dual combinatorial approach as disclosed in WO 92/01047 in which an individual colony containing either an H or L chain clone is used to infect a complete library of clones encoding the other chain (L or H) and the resulting two-chain specific binding member is selected in accordance with phage display techniques such as those described therein. This technique is also disclosed in Marks et al, *Bio/Technology*, 10:779-783, 1992.

Methods for display of polypeptides on the surface of viruses, yeast, microbial and mammalian cells have also been used to identify antigen specific antibodies. See, for example, U.S. Pat. Nos. 5,348,867; 5,723,287; 6,699,658; Wittrup, *Curr Op. Biotech.* 12:395-99, 2001; Lee et al, *Trends in Biotech.* 21(1) 45-52, 2003; Surgeeva et al, *Adv. Drug Deliv. Rev.* 58: 1622-54, 2006. Antibody libraries may be attached to yeast proteins, such as agglutinin, effectively mimicking the cell surface display of antibodies by B cells in the immune system.

In addition to phage display methods, antibodies may be isolated using in vitro display methods including ribosome display and mRNA display (Amstutz et al, *Curr. Op. Biotech.* 12: 400-05, 2001). Selection of polypeptide using ribosome display is described in Hanes et al., *Proc. Natl Acad Sci USA*, 94:4937-4942, 1997 and U.S. Pat. Nos. 5,643,768 and 5,658,754 issued to Kawasaki. Ribosome display is also useful for rapid large scale mutational analysis of antibodies. The selective mutagenesis approach also provides a method of producing antibodies with improved activities that can be selected using ribosomal display techniques.

Altered Glycosylation

Antibody variants can also be produced that have a modified glycosylation pattern relative to the parent antibody, for example, deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. The presence of either of these tripeptide sequences in a polypeptide creates a potential glycosylation site. Thus, N-linked glycosylation sites may be added to an antibody by altering the amino acid sequence such that it contains one or more of these tripeptide sequences. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used. O-linked glycosylation sites may be added to an antibody by inserting or substituting one or more serine or threonine residues to the sequence of the original antibody.

Fc glycans influence the binding of IgG to Fc receptors and C1q, and are therefore important for IgG effector functions. Antibody variants with modified Fc glycans and altered effector function may be produced. For example, antibodies with modified terminal sugars such as sialic acids, core fucose, bisecting N-acetylglucosamine, and mannose residues may have altered binding to the FcγRIIIa receptor and altered ADCC activity. In a further example, antibodies with modified terminal galactose residues may have altered binding to C1q and altered CDC activity (Raju, *Curr. Opin. Immunol.* 20: 471-78, 2008).

Also contemplated are antibody molecules with absent or reduced fucosylation that exhibit improved ADCC activity. A variety of ways are known in the art to accomplish this. For example, ADCC effector activity is mediated by binding of the antibody molecule to the FcγRIII receptor, which has been shown to be dependent on the carbohydrate structure of the N-linked glycosylation at the Asn-297 of the CH2 domain. Non-fucosylated antibodies bind this receptor with increased affinity and trigger FcγRIII-mediated effector functions more efficiently than native, fucosylated antibodies. For example, recombinant production of non-fucosylated antibody in CHO cells in which the alpha-1,6-fucosyl transferase enzyme has been knocked out results in antibody with 100-fold increased ADCC activity (Yamane-Ohnuki et al., *Biotechnol Bioeng.* 87:614-22, 2004). Similar effects can be accomplished through decreasing the activity of this or other enzymes in the fucosylation pathway, e.g., through siRNA or antisense RNA treatment, engineering cell lines to knockout the enzyme(s), or culturing with selective glycosylation inhibitors (Rothman et al., *Mol Immunol.* 26:1113-23, 1989). Some host cell strains, e.g. Lec13 or rat hybridoma YB2/0 cell line naturally produce antibodies with lower fucosylation levels. (Shields et al., *J Biol Chem.* 277:26733-40, 2002; Shinkawa et al., *J Biol Chem.* 278: 3466-73, 2003). An increase in the level of bisected carbohydrate, e.g. through recombinantly producing antibody in cells that overexpress GnTIII enzyme, has also been determined to increase ADCC activity (Umana et al., *Nat Biotechnol.* 17:176-80, 1999). It has been predicted that the absence of only one of the two fucose residues may be sufficient to increase ADCC activity (Ferrara et al., *Biotechnol Bioeng.* 93:851-61, 2006). Glycosylation of antibodies and methods are reviewed in Niewa and Satoh, *J. Pharmaceutical Sciences* 104:930-41, 2015.

Variants with Altered Effector Function

Other modifications of the antibody are contemplated. In one aspect, it may be desirable to modify the antibody useful in the methods, e.g., with respect to effector function, for example, to enhance the effectiveness of the antibody in treating cancer and other conditions (Natsume et al, *Drug Design Dev't & Ther.* 3: 7-16, 2009). Exemplary effector functions include C1q binding; CDC; Fc receptor binding; ADCC; phagocytosis; down regulation of cell surface receptors (e.g. B cell receptor; BCR), etc. One method for modifying effector function teaches that cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176: 1191-1195, 1992, and Shopes, B. *J. Immunol.* 148: 2918-2922, 1992. Homodimeric antibodies with enhanced anti-tumor activity may also be prepared using heterobifunctional cross-linkers as described in Wolff et al., *Cancer Research* 53: 2560-2565, 1993. Alternatively, an antibody can be engineered which has dual Fc regions and may thereby have enhanced complement lysis and ADCC capabilities. See Stevenson et al., *Anti-Cancer Drug Design* 3: 219-230, 1989. In certain embodiments of the disclosure, it may be desirable to use an antibody fragment, rather than an intact antibody. In this case, it may be desirable to modify the antibody fragment in order to increase its serum half-life, for example, adding molecules such as PEG or other water soluble polymers, including polysaccharide polymers, to antibody fragments to increase the half-life. This may also be achieved, for example, by incorporation of a salvage receptor binding epitope into the antibody fragment (e.g., by mutation of the appropriate region in the antibody fragment or by incorporating the epitope into a peptide tag that is then fused to the antibody fragment at either end or in the middle, e.g., by DNA or peptide synthesis) (see, e.g., WO96/32478).

Thus, antibodies contemplated herein may comprise a human Fc portion, a human consensus Fc portion, or a variant thereof that retains the ability to interact with the Fc salvage receptor, including variants in which cysteines involved in disulfide bonding are modified or removed, and/or in which the a methionine is added at the N-terminus and/or one or more of the N-terminal 20 amino acids are removed, and/or regions that interact with complement, such as the C1q binding site, are removed, and/or the ADCC site is removed (see, e.g., Sarmay et al., *Molec. Immunol.* 29:633-9, 1992).

Previous studies mapped the binding site on human and murine IgG for FcR primarily to the lower hinge region composed of IgG residues 233-239. Other studies proposed additional broad segments, e.g. Gly316-Lys338 for human Fc receptor I, Lys274-Arg301 and Tyr407-Arg416 for human Fc receptor III, or found a few specific residues outside the lower hinge, e.g., Asn297 and Glu318 for murine IgG2b interacting with murine Fc receptor II. The report of the 3.2-Å crystal structure of the human IgG1 Fc fragment with human Fc receptor IIIA delineated IgG1 residues Leu234-Ser239, Asp265-Glu269, Asn297-Thr299, and Ala327-Ile332 as involved in binding to Fc receptor IIIA. It has been suggested based on crystal structure that in addition to the lower hinge (Leu234-Gly237), residues in IgG CH2 domain loops FG (residues 326-330) and BC (residues 265-271) might play a role in binding to Fc receptor IIA. See Shields et al., *J. Biol. Chem.*, 276:6591-604, 2001), incorporated by reference herein in its entirety. Mutation of residues within Fc receptor binding sites can result in altered effector function, such as altered ADCC or CDC activity, or altered half-life. As described above, potential mutations include insertion, deletion or substitution of one or more residues, including substitution with alanine, a conservative substitution, a non-conservative substitution, or replacement with a corresponding amino acid residue at the same position from a different IgG subclass (e.g. replacing an IgG1 residue with a corresponding IgG2 residue at that position).

Shields et al. reported that IgG1 residues involved in binding to all human Fc receptors are located in the CH2 domain proximal to the hinge and fall into two categories as follows: 1) positions that may interact directly with all FcR include Leu234-Pro238, Ala327, and Pro329 (and possibly Asp265); 2) positions that influence carbohydrate nature or position include Asp265 and Asn297. The additional IgG1 residues that affected binding to Fc receptor II are as follows: (largest effect) Arg255, Thr256, Glu258, Ser267, Asp270, Glu272, Asp280, Arg292, Ser298, and (less effect) His268, Asn276, His285, Asn286, Lys290, Gln295, Arg301, Thr307, Leu309, Asn315, Lys322, Lys326, Pro331, Ser337, Ala339, Ala378, and Lys414. A327Q, A327S, P329A, D265A and D270A reduced binding. In addition to the residues identified above for all FcR, additional IgG1 residues that reduced binding to Fc receptor IIIA by 40% or more are as follows: Ser239, Ser267 (Gly only), His268, Glu293, Gln295, Tyr296, Arg301, Val303, Lys338, and Asp376. Variants that improved binding to FcRIIIA include T256A, K290A, S298A, E333A, K334A, and A339T. Lys414 showed a 40% reduction in binding for FcRIIA and FcRIIB, Arg416 a 30% reduction for FcRIIA and FcRIIIA, Gln419 a 30% reduction to FcRIIA and a 40% reduction to FcRIIB, and Lys360 a 23% improvement to FcRIIIA See also Presta et al., *Biochem. Soc. Trans.* 30:487-490, 2001, incorporated herein by reference in its entirety, which described several positions in the Fc region of IgG1 were found which improved binding only to specific Fc gamma receptors (R) or simultaneously improved binding to one type of Fc gamma R and reduced binding to another type. Selected IgG1 variants with improved binding to Fc gamma RIIIa were then tested in an in vitro antibody-dependent cellular cytotoxicity (ADCC) assay and showed an enhancement in ADCC when either peripheral blood mononuclear cells or natural killer cells were used.

For example, U.S. Pat. No. 6,194,551, incorporated herein by reference in its entirety, describes variants with altered effector function containing mutations in the human IgG Fc region, at amino acid position 329, 331 or 322 (using Kabat numbering), some of which display reduced C1q binding or CDC activity.

Covalent Modifications

Covalent modifications of the polypeptide binding agents, e.g., antibodies, are also included within the scope of this disclosure. They may be made by chemical synthesis or by enzymatic or chemical cleavage of the polypeptide binding agent, if applicable. Other types of covalent modifications of the polypeptide binding agent are introduced into the molecule by reacting targeted amino acid residues of the polypeptide binding agent with an organic derivatizing agent that is capable of reacting with selected side chains or the N- or C-terminal residues.

Other modifications include histidyl, lysinyl arginyl, tyrosyl, glutaminyl and asparaginyl hydroxylation of proline and lysine. Methods for making such modifications are disclosed in U.S. Pat. No. 8,926,976, incorporated herein by reference, and in the art.

Derivatives

Derivative refers to polypeptide binding agents, including antibodies, chemically modified by such techniques as ubiquitination, labeling (e.g., with radionuclides or various enzymes), covalent polymer attachment such as pegylation (derivatization with polyethylene glycol) and insertion or substitution by chemical synthesis of amino acids such as ornithine. Derivatives of the polypeptide binding agents described herein, such as an antibody, are also useful as therapeutic agents and may be produced by methods described herein The conjugated moiety can be incorporated in or attached to a polypeptide binding agent either covalently, or through ionic, van der Waals or hydrogen bonds, e.g., incorporation of radioactive nucleotides, or biotinylated nucleotides that are recognized by streptavadin.

Polyethylene glycol (PEG) may be attached to the polypeptide binding agents to provide a longer half-life in vivo. The PEG group may be of any convenient molecular weight and may be linear or branched. The average molecular weight of the PEG will preferably range from about 2 kiloDalton ("kD") to about 100 kDa, more preferably from about 5 kDa to about 50 kDa, most preferably from about 5 kDa to about 10 kDa. The PEG groups will generally be attached to the polypeptide binding agents via acylation or reductive alkylation through a natural or engineered reactive group on the PEG moiety (e.g., an aldehyde, amino, thiol, or ester group) to a reactive group on the polypeptide binding agent (e.g., an aldehyde, amino, or ester group). Addition of PEG moieties to polypeptide binding agents can be carried out using techniques well-known in the art. See, e.g., International Publication No. WO 96/11953 and U.S. Pat. No. 4,179,337.

Ligation of the polypeptide binding agent with PEG usually takes place in aqueous phase and can be easily monitored by reverse phase analytical HPLC. The PEGylated substances are purified by preparative HPLC and characterized by analytical HPLC, amino acid analysis and laser desorption mass spectrometry.

Antibody Conjugates

A polypeptide binding agent may be administered in its "naked" or unconjugated form, or may be conjugated directly to other therapeutic or diagnostic agents, or may be conjugated indirectly to carrier polymers comprising such other therapeutic or diagnostic agents. In some embodiments the polypeptide binding agent is conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). Suitable chemotherapeutic agents include: daunomycin, doxorubicin, methotrexate, and vindesine (Rowland et al., 1986, supra). Suitable toxins include: bacterial toxins such as diphtheria toxin; plant toxins such as ricin; small molecule toxins such as geldanamycin (Mandler et al J. Natl. Cancer Inst. 92(19):1573-81, 2000; Mandler et al., Bioorg. Med. Chem. Letters 10:1025-1028, 2000; Mandler et al., Bioconjugate Chem. 13.786-91, 2002), maytansinoids (EP 1391213; Liu et al., Proc. Natl. Acad. Sci. USA 93:8618-23, 1996), auristatins (Doronina et al., Nat. Biotech. 21: 778-84, 2003) and calicheamicin (Lode et al., Cancer Res. 58:2928, 1998; Hinman et al., Cancer Res. 53:3336-3342, 1993, see also Brandon et al., Nature Rev. Clin. Oncol. 11: 637-648, 2014).

Polypeptide binding agents can be detectably labeled through the use of radioisotopes, affinity labels (such as biotin, avidin, etc.), enzymatic labels (such as horseradish peroxidase, alkaline phosphatase, etc.) fluorescent or luminescent or bioluminescent labels (such as FITC or rhodamine, etc.), paramagnetic atoms, and the like. Procedures for accomplishing such labeling are well known in the art; for example, see (Sternberger, L. A. et al., J. Histochem. Cytochem. 18:315, 1970; Bayer, E. A. et al., Meth. Enzym. 62:308, 1979; Engval, E. et al., Immunol. 109:129, 1972; Goding, J. W. J. Immunol. Meth. 13:215, 1976).

Conjugation of polypeptide binding agent moieties is described in U.S. Pat. No. 6,306,393. General techniques are also described in Shih et al., Int. J. Cancer 41:832-839, 1988; Shih et al., Int. J. Cancer 46:1101-1106, 1990; and Shih et al., U.S. Pat. No. 5,057,313. This general method involves reacting a polypeptide binding agent component having an oxidized carbohydrate portion with a carrier polymer that has at least one free amine function and that is loaded with a plurality of drug, toxin, chelator, boron addends, or other therapeutic agent. This reaction results in an initial Schiff base (imine) linkage, which can be stabilized by reduction to a secondary amine to form the final conjugate.

The carrier polymer may be, for example, an aminodextran or polypeptide of at least 50 amino acid residues. Various techniques for conjugating a drug or other agent to the carrier polymer are known in the art. A polypeptide carrier can be used instead of aminodextran, but the polypeptide carrier should have at least 50 amino acid residues in the chain, preferably 100-5000 amino acid residues. At least some of the amino acids should be lysine residues or glutamate or aspartate residues. The pendant amines of lysine residues and pendant carboxylates of glutamine and aspartate are convenient for attaching a drug, toxin, immunomodulator, chelator, boron addend or other therapeutic agent. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier and conjugate.

Alternatively, conjugated polypeptide binding agents can be prepared by directly conjugating a polypeptide binding agent component with a therapeutic agent. The general procedure is analogous to the indirect method of conjugation except that a therapeutic agent is directly attached to an oxidized polypeptide binding agent component. For example, a carbohydrate moiety of a polypeptide binding agent can be attached to polyethyleneglycol to extend half-life.

Alternatively, a therapeutic agent can be attached at the hinge region of a reduced antibody component via disulfide bond formation, or using a heterobifunctional cross-linker, such as N-succinyl 3-(2-pyridyldithio)proprionate (SPDP). Yu et al., *Int. J. Cancer* 56:244, 1994. General techniques for such conjugation are well-known in the art. See, for example, Wong, Chemistry Of Protein Conjugation and Cross-Linking, CRC Press, 1991; Upeslacis et al., "Modification of Antibodies by Chemical Methods," in Monoclonal Antibodies: Principles and Applications, Birch et al. (eds.), pages 187-230, Wiley-Liss, Inc., 1995; Price, "Production and Characterization of Synthetic Peptide-Derived Antibodies," in Monoclonal Antibodies: Production, Engineering and Clinical Application, Ritter et al. (eds.), pages 60-84, Cambridge University Press, 1995. A variety of bifunctional protein coupling agents are known in the art, such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

Antibody Fusion Proteins

Methods of making antibody fusion proteins are well known in the art. See, e.g., U.S. Pat. No. 6,306,393. Antibody fusion proteins comprising an interleukin-2 moiety are described by Boleti et al., *Ann. Oncol.* 6:945, 1995; Nicolet et al., *Cancer Gene Ther.* 2:161, 1995; Becker et al., *Proc. Nat'l Acad. Sci. USA* 93:7826, 1996; Hank et al., *Clin. Cancer Res.* 2:1951, 1996; and Hu et al., *Cancer Res.* 56:4998, 1996. In addition, Yang et al., *Hum. Antibodies Hybridomas* 6:129, 1995, describe a fusion protein that includes an F(ab')$_2$ fragment and a tumor necrosis factor alpha moiety. Further examples of antibody fusion proteins are described by Pastan et al, *Nat. Reviews Cancer* 6: 559-65, 2006, and Alewine et al. *The Oncologist*, 20: 176-185, 2015.

Methods of making antibody-toxin fusion proteins in which a recombinant molecule comprises one or more antibody components and a toxin or chemotherapeutic agent also are known to those of skill in the art. For example, antibody-*Pseudomonas* exotoxin A fusion proteins have been described by Chaudhary et al., *Nature* 339:394, 1989, Brinkmann et al., *Proc. Nat'l Acad. Sci. USA* 88:8616, 1991, Batra et al., *Proc. Nat'l Acad. Sci. USA* 89:5867, 1992, Friedman et al., *J. Immunol.* 150:3054, 1993, Wels et al., *Int. J. Can.* 60:137, 1995, Fominaya et al., *J. Biol. Chem.* 271:10560, 1996, Kuan et al., *Biochemistry* 35:2872, 1996, and Schmidt et al., *Int. J. Can.* 65:538, 1996. Antibody-toxin fusion proteins containing a diphtheria toxin moiety have been described by Kreitman et al., *Leukemia* 7:553, 1993, Nicholls et al., *J. Biol. Chem.* 268:5302, 1993, Thompson et al., *J. Biol. Chem.* 270:28037, 1995, and Vallera et al., *Blood* 88:2342, 1996. Deonarain et al., *Tumor Targeting* 1:177, 1995, have described an antibody-toxin fusion protein having an RNase moiety, while Linardou et al., *Cell Biophys.* 24-25:243, 1994, produced an antibody-toxin fusion protein comprising a DNase I component. Gelonin was used as the toxin moiety in the antibody-toxin fusion protein of Wang et al., *Abstracts of the 209th ACS National Meeting*, Anaheim, Calif., Apr. 2-6, 1995, Part 1, BIOT005. As a further example, Dohlsten et al., *Proc. Nat'l Acad. Sci. USA* 91:8945, 1994, reported an antibody-toxin fusion protein comprising Staphylococcal enterotoxin-A.

Illustrative of toxins which are suitably employed in the preparation of such fusion proteins are ricin, abrin, ribonuclease, DNase I, Staphylococcal enterotoxin-A, pokeweed antiviral protein, gelonin, diphtherin toxin, *Pseudomonas* exotoxin, and *Pseudomonas* endotoxin. See, for example, Pastan et al., *Cell* 47:641, 1986, and Goldenberg, C A *A Cancer Journal for Clinicians* 44:43, 1994. Other suitable toxins are known to those of skill in the art.

Antibodies herein may also be used in ADEPT by conjugating the antibody to a prodrug-activating enzyme which converts a prodrug (e.g., a peptidyl chemotherapeutic agent, See WO81/01145) to an active anti-cancer drug. See, for example, WO88/07378 and U.S. Pat. No. 4,975,278.

The enzyme component of the immunoconjugate useful for ADEPT includes any enzyme capable of acting on a prodrug in such a way so as to convert it into its more active, cytotoxic form.

Enzymes that are useful for purposes of the disclosure include, but are not limited to: alkaline phosphatase; arylsulfatase; cytosine deaminase, 5-fluorouracil; proteases, such as *serratia* protease, thermolysin, subtilisin, carboxypeptidases and cathepsins (such as cathepsins B and L); D-alanylcarboxypeptidases; carbohydrate-cleaving enzymes such as β-galactosidase and neuraminidase; β-lactamase; and penicillin amidases, such as penicillin V amidase or penicillin G amidase. Alternatively, antibodies with enzymatic activity, also known in the art as abzymes, can be used to convert prodrugs into free active drugs (See, e.g., Massey, *Nature* 328: 457-458, 1987. Antibody-abzyme conjugates can be prepared as described herein for delivery of the abzyme to a tumor cell population.

The enzymes above can be covalently bound to the antibodies by techniques well known in the art such as the use of the heterobifunctional crosslinking reagents discussed above. Alternatively, fusion proteins comprising at least the antigen binding region of an antibody described herein linked to at least a functionally active portion of an enzyme can be constructed using recombinant DNA techniques well known in the art (See, e.g., Neuberger et al., *Nature* 312: 604-608, 1984).

Amino Acid Sequence Variants

It is contemplated that modified polypeptide compositions comprising one, two, three, four, five, and/or six CDRs of an antibody or polypeptide binding agent are generated, wherein a CDR or non-CDR region is altered to provide increased specificity or affinity to the antigen, or to provide increased modulation of binding affinity between the target and its signaling partner. For example, sites within antibody CDRs are typically modified in series, e.g., by substituting first with conservative choices (e.g., hydrophobic amino acid substituted for a non-identical hydrophobic amino acid) and then with more dissimilar choices (e.g., hydrophobic amino acid substituted for a charged amino acid), and then deletions or insertions may be made at the targeted site. It is contemplated that conservative substitutions within the CDR allow the variable region to retain biological activity. For example, using the conserved framework sequences surrounding the CDRs, PCR primers complementary to these consensus sequences are generated to amplify the antigen-specific CDR sequence located between the primer regions. Techniques for cloning and expressing nucleotide and polypeptide sequences are well-established in the art [see, e.g., Sambrook et al., Molecular Cloning: A Laboratory Manual, 2nd Edition, Cold Spring Harbor, N.Y., 1989]. The amplified CDR sequences are ligated into an appropriate plasmid. The plasmid comprising one, two, three, four, five and/or six cloned CDRs optionally contains additional polypeptide encoding regions linked to the CDR.

Polypeptide binding agents comprising the modified CDRs are screened for binding affinity for the original antigen. Additionally, the antibody or polypeptide is further tested for its ability to neutralize the activity of its antigen. For example, antibodies herein may be analyzed as set out in the Examples to determine their ability to interfere with the biological activity of the target.

Modifications may be made by conservative or non-conservative amino acid substitutions described in greater detail below. "Insertions" or "deletions" are preferably in the range of about 1 to 20 amino acids, more preferably 1 to 10 amino acids. The variation may be introduced by systematically making substitutions of amino acids in an antibody polypeptide molecule using recombinant DNA techniques and assaying the resulting recombinant variants for activity. Nucleic acid alterations can be made at sites that differ in the nucleic acids from different species (variable positions) or in highly conserved regions (constant regions). Methods for altering antibody sequences and expressing antibody polypeptide compositions useful in the invention are described in greater detail below.

Amino acid sequence insertions include amino- and/or carboxyl-terminal fusions ranging in length from one residue to polypeptides containing a hundred or more residues, as well as intra-sequence insertions of single or multiple amino acid residues. Examples of terminal insertions include an antibody with an N-terminal methionyl residue or the antibody (including antibody fragment) fused to an epitope tag or a salvage receptor epitope. Other insertional variants of the antibody molecule include the fusion to a polypeptide which increases the serum half-life of the antibody, e.g. at the N-terminus or C-terminus.

The term "epitope tagged" refers to the antibody fused to an epitope tag. The epitope tag polypeptide has enough residues to provide an epitope against which an antibody there against can be made, yet is short enough such that it does not interfere with activity of the antibody. The epitope tag preferably is sufficiently unique so that the antibody there against does not substantially cross-react with other epitopes. Suitable tag polypeptides generally have at least 6 amino acid residues and usually between about 8-50 amino acid residues (preferably between about 9-30 residues). Examples include the flu hemagglutinin (HA) tag polypeptide and its antibody 12CA5 (Field et al., *Mol. Cell. Biol.* 8: 2159-2165, 1988); the c-myc tag and the 8F9, 3C7, 6E10, G4, B7 and 9E10 antibodies thereto (Evan et al., *Mol. Cell. Biol.* 5:3610-16, 1985); and the Herpes Simplex virus glycoprotein D (gD) tag and its antibody (Paborsky et al., *Protein Engineering* 3:547-53, 1990). Other exemplary tags are a poly-histidine sequence, generally around six histidine residues, that permits isolation of a compound so labeled using nickel chelation. Other labels and tags, such as the FLAG® tag (Eastman Kodak, Rochester, N.Y.), well known and routinely used in the art, are embraced by the invention.

As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Another type of variant is an amino acid substitution variant. These variants have at least one amino acid residue in the antibody molecule removed and a different residue inserted in its place. Substitutional mutagenesis within any of the hypervariable or CDR regions or framework regions is contemplated. Conservative substitutions involve replacing an amino acid with another member of its class. Non-conservative substitutions involve replacing a member of one of these classes with a member of another class.

Conservative amino acid substitutions are made on the basis of similarity in polarity, charge, solubility, hydrophobicity, hydrophilicity, and/or the amphipathic nature of the residues involved. For example, nonpolar (hydrophobic) amino acids include alanine (Ala, A), leucine (Leu, L), isoleucine (Ile, I), valine (Val, V), proline (Pro, P), phenylalanine (Phe, F), tryptophan (Trp, W), and methionine (Met, M); polar neutral amino acids include glycine (Gly, G), serine (Ser, S), threonine (Thr, T), cysteine (Cys, C), tyrosine (Tyr, Y), asparagine (Asn, N), and glutamine (Gln, Q); positively charged (basic) amino acids include arginine (Arg, R), lysine (Lys, K), and histidine (His, H); and negatively charged (acidic) amino acids include aspartic acid (Asp, D) and glutamic acid (Glu, E).

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

Formulation of Pharmaceutical Compositions

To administer polypeptide binding agents to human or test mammals, it is preferable to formulate the polypeptide binding agent in a sterile composition comprising one or more sterile pharmaceutically acceptable carriers. The phrase "pharmaceutically or pharmacologically acceptable" refer to molecular entities and compositions that do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like.

The polypeptide binding agent is administered by any suitable means, including parenteral, subcutaneous, intraperitoneal, intrapulmonary, and intranasal, and, if desired for local treatment, intralesional administration. Parenteral infusions include intravenous, intraarterial, intraperitoneal, intramuscular, intradermal or subcutaneous administration. Preferably the dosing is given by injections, most preferably intravenous or subcutaneous injections, depending in part on whether the administration is brief or chronic. Other administration methods are contemplated, including topical, particularly transdermal, transmucosal, rectal, oral or local administration e.g. through a catheter placed close to the desired site infusion pump or depot, and optionally including the use of delivery devices such pumps, smart devices, and sensors.

Pharmaceutical compositions useful in the present invention containing a polypeptide binding agent described herein as an active ingredient may contain sterile pharmaceutically acceptable carriers or additives depending on the route of administration. Examples of such carriers or additives include water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, glycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof, as appropriate, depending on the dosage form used herein. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers. A variety of aqueous carriers are suitable, e.g., sterile phosphate buffered saline solutions, bacteriostatic water, water, buffered water, 0.4% saline, 0.3% glycine, and the like, and may include other proteins for enhanced stability, such as albumin, lipoprotein, globulin, etc., subjected to mild chemical modifications or the like.

Therapeutic formulations of the polypeptide binding agent are prepared for storage by mixing the polypeptide binding agent having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, succinate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed., 1980.

The formulations to be used for in vivo administration must be sterile. This is readily accomplished by filtration through sterile filtration membranes.

Aqueous suspensions may contain the active compound in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate.

In certain embodiments, an polypeptide binding agent used in the methods is in a pharmaceutical composition comprising one or more of a surfactant, an antioxidant, a stabilizer, an amino acid, and/or a sugar.

In various embodiments, the pharmaceutical composition comprising an antibody further comprises, for example, from 1-20 mM histidine, from 1-20 mM methionine, from 150 to 500 mM sorbitol, or from 0.5% to 7% sorbitol, from 0.005 to 0.1% polysorbate 20, at pH 6.8 to 5.5 or 7.2 to 5.5. In various embodiments, the composition also comprises a buffer, such as a succinate buffer, sodium phosphate buffer, acetate buffer or other buffer useful in a therapeutic composition.

The antibodies described herein can be lyophilized for storage and reconstituted in a suitable carrier prior to use. This technique has been shown to be effective with conventional immunoglobulins. Any suitable lyophilization and reconstitution techniques can be employed. It will be appreciated by those skilled in the art that lyophilization and reconstitution can lead to varying degrees of antibody activity loss and that use levels may have to be adjusted to compensate.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above.

The concentration of polypeptide binding agent in these formulations can vary widely, for example from less than about 0.5%, usually at or at least about 1% to as much as 15 or 20% by weight and will be selected primarily based on fluid volumes, viscosities, etc., in accordance with the particular mode of administration selected. Thus, a typical pharmaceutical composition for parenteral injection could be made up to contain 1 ml sterile buffered water, and 50 mg of polypeptide binding agent. A typical composition for intravenous infusion could be made up to contain 250 ml of sterile Ringer's solution, and 150 mg of polypeptide binding agent. Actual methods for preparing parenterally administrable compositions will be known or apparent to those skilled in the art and are described in more detail in, for example, Remington's Pharmaceutical Science, 15th ed., Mack Publishing Company, Easton, Pa., 1980. An effective dosage of polypeptide binding agent is within the range of 0.01 mg to 25 mg per kg of body weight per administration.

The pharmaceutical compositions may be in the form of a sterile injectable aqueous, oleaginous suspension, dispersions or sterile powders for the extemporaneous preparation of sterile injectable solutions or dispersions. The suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. The carrier can be a solvent or dispersion medium containing, for example, water, ethanol, polyol (for example, glycerol, propylene glycol, and liquid polyethylene glycol, and the like), suitable mixtures thereof, vegetable oils, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

In all cases the form must be sterile and must be fluid to the extent that easy syringability exists. The proper fluidity can be maintained, for example, by the use of a coating, such as lecithin, by the maintenance of the required particle size in the case of dispersion and by the use of surfactants. It must be stable under the conditions of manufacture and storage and must be preserved against the contaminating action of microorganisms, such as bacteria and fungi. The prevention of the action of microorganisms can be brought about by various antibacterial and antifungal agents, for example, parabens, chlorobutanol, phenol, sorbic acid, thimerosal, and the like. In many cases, it will be desirable to include isotonic agents, for example, sugars or sodium chloride. Prolonged absorption of the injectable compositions can be brought about by the use in the compositions of agents delaying absorption, for example, aluminum monostearate and gelatin.

Compositions useful for administration may be formulated with uptake or absorption enhancers to increase their efficacy. Such enhancers include for example, salicylate, glycocholate/linoleate, glycholate, aprotinin, bacitracin, SDS, caprate and the like. See, e.g., Fix, *J. Pharm. Sci.* 85:1282-1285, 1996) and Oliyai and Stella, *Ann. Rev. Pharmacol. Toxicol.,* 32:521-544, 1993.

Administration and Dosing

In one aspect, the disclosure provides methods of administering a pharmaceutical composition comprising a negative modulator antibody as described herein.

Methods of the invention are performed using any medically-accepted means for introducing a therapeutic directly or indirectly into a mammalian subject, including but not limited to injections, infusions, oral ingestion, intranasal, topical, transdermal, parenteral, inhalation spray, vaginal, or rectal administration. The term parenteral as used herein includes subcutaneous, intravenous, intramuscular, and intracisternal injections, as well as catheter or infusion techniques. Administration by, intradermal, intramammary, intraperitoneal, intrathecal, retrobulbar, intrapulmonary injection and or surgical implantation at a particular site is contemplated as well. Suitable delivery devices may include those developed for the delivery of insulin (see, e.g., Owens et al *Diabetic Med.* 20(11):886-898, 2003; US20140128803; and Peyser et al., *Annals NY Acad Sci,* 1311:102-123, 2014).

In one embodiment, administration is performed at the site of an affected tissue needing treatment by direct injection into the site or via a sustained delivery or sustained release mechanism, which can deliver the formulation internally. For example, biodegradable microspheres or capsules or other biodegradable polymer configurations capable of sustained delivery of a composition (e.g., a soluble polypeptide, antibody, or small molecule) can be included in the formulations useful in the disclosure implanted at the site.

Therapeutic compositions may also be delivered to the patient at multiple sites. The multiple administrations may be rendered simultaneously or may be administered over a period of time. In certain cases it is beneficial to provide a continuous flow of the therapeutic composition. Additional therapy may be administered on a period basis, for example, hourly, daily, weekly, every 2 weeks, every 3 weeks, or monthly.

Also contemplated in the present methods is the administration of multiple agents, such as an antibody composition in conjunction with a second agent as described herein.

The amounts of antibody composition in a given dosage will vary according to the size of the individual to whom the therapy is being administered as well as the characteristics of the disorder being treated. In exemplary treatments, it may be necessary to administer about 0.1 to about 25 mg/kg per dose or per day, or from about 0.05 to 10 mg/kg, from about 0.3 to 6 mg/kg, or from about 0.1 to 3 mg/kg. Exemplary doses include, 0.1 mg/kg, 0.3 mg/kg, 0.5 mg/kg 1 mg/day, 0.75 mg/kg, 1.0 mg/kg, 1.5 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, or 25 mg/kg. Other doses include 1 mg/day, 2.5 mg/day, 5 mg/day, 10 mg/day, 20 mg/day, 25 mg/day, 50 mg/day, 75 mg/day, 100 mg/day, 150 mg/day, 200 mg/day, 250 mg/day, 500 mg/day or 1000 mg/day. These concentrations may be administered as a single dosage form or as multiple doses or continuously. Standard dose-response studies, first in animal models and then in clinical testing, reveal optimal dosages for particular disease states and patient populations.

Combination Therapy

It one embodiment, an antibody described herein is administered with a second agent useful to treat a disease or disorder as described herein. Compositions comprising one or more antibody described herein may be administered to persons or mammals suffering from, or predisposed to suffer from, a condition or disorder to be treated associated with the target polypeptide.

Concurrent administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks.

A second agent may be other therapeutic agents, such as anti-diabetic agents, cytokines, growth factors, other anti-inflammatory agents, anti-coagulant agents, agents that will lower or reduce blood pressure, agents that will reduce cholesterol, triglycerides, LDL, VLDL, or lipoprotein(a) or increase HDL, agents that will increase or decrease levels of cholesterol-regulating proteins, anti-neoplastic drugs or molecules. For patients with a hyperproliferative disorder, such as cancer or a tumor, combination with second therapeutic modalities such as radiotherapy, chemotherapy, photodynamic therapy, or surgery is also contemplated.

Exemplary agents include, but are not limited to, insulin, glucagon, acarbose, octreotide, verapamil, diazoxide and other agents useful to treat hypoglycemia or side effects associated with hypoglycemia. In various embodiments, an antibody described herein is administered with insulin and/or glucagon, optionally in a delivery device, e.g., a smart delivery device (see, e.g., US20140128803) or dual sensor/pump (e.g., a bionic pancreas system).

Any of the foregoing antibodies or fragments thereof described herein may be concurrently administered with a second agent that is an anti-diabetic agent known in the art or described herein, as adjunct therapy. Compositions comprising any of the foregoing antibodies or polypeptides of the invention together with other anti-diabetic agents are also contemplated.

A number of anti-diabetic agents are known in the art, including but not limited to: 1) sulfonylureas (e.g., glimepiride, glisentide, sulfonylurea, AY31637); 2) biguanides (e.g., metformin); 3) alpha-glucosidase inhibitors (e.g., acarbose, miglitol); 4) thiazol-idinediones (e.g., troglitazone, pioglitazone, rosiglitazone, glipizide, balaglitazone, rivoglitazone, netoglitazone, troglitazone, englitazone, AD 5075, T 174, YM 268, R 102380, NC 2100, NIP 223, NIP 221, MK 0767, ciglitazone, adaglitazone, CLX 0921, darglitazone, CP 92768, BM 152054); 5) glucagon-like-peptides (GLP) and GLP analogs or agonists of GLP-1 receptor (e.g., exendin) or stabilizers thereof (e.g., DPP4 inhibitors, such as sitagliptin); 6) insulin or analogues or mimetics thereof (e.g., LANTUS®); and 7) glucagon (e.g. GlucaGen hypoKit).

It is contemplated the antibody and the second agent may be given simultaneously, in the same formulation. It is further contemplated that the agents are administered in a separate formulation and administered concurrently, with concurrently referring to agents given within 30 minutes of each other.

In another aspect, the second agent is administered prior to administration of the antibody composition. Prior administration refers to administration of the second agent within the range of one week prior to treatment with the antibody, up to 30 minutes before administration of the antibody. It is further contemplated that the second agent is administered subsequent to administration of the antibody composition. Subsequent administration is meant to describe administration from 30 minutes after antibody treatment up to one week after antibody administration.

It is further contemplated that other adjunct therapies may be administered, where appropriate. For example, the patient may also be administered a diet or food plan designed for a hypoglycemic patient, surgical therapy, or radiation therapy where appropriate.

It will also be apparent that dosing may be modified if traditional therapeutics are administered in combination with therapeutics described herein.

Methods of Use

It is contemplated herein that a negative modulator antibody that binds the INSR is useful to treat and prevent symptoms associated with hypoglycemia and hyperinsulinemia. In various embodiments, the disorder or condition to be treated or prevented is selected from the group consisting of Kaposi's sarcoma, insulinoma, brittle diabetes, post-artificial pancreas procedure hypoglycemia, abnormal glucose metabolism, post-bariatric surgery hypoglycemia, exercise-induced hypoglycemia, diabetic renal disease, cancer, hypoglycemia, nocturnal hypoglycemia, sulfonylurea-induced hypoglycemia, insulin-induced hypoglycemia, nesidioblastosis (KATP-H1 Diffuse Disease, KATP-H1 Focal Disease, or "PHHI"), GDH-H1 (Hyperinsulinism/Hyperammonaemia Syndrome (HI/HA), leucine-sensitive hypoglycemia, or diazoxide-sensitive hypoglycemia), islet cell dysregulation syndrome, idiopathic hypoglycemia of infancy, Persistent Hyperinsulinemic Hypoglycemia of Infancy (PHHI), Congenital Hyperinsulinism, (intentional) insulin overdose, hypoglycemia due to renal failure (acute or chronic), hypoglycemia due to inherited metabolic diseases (see, e.g., Douillard et al., Orphanet J Rare Disease, 7:26, 2012), Nissen fundoplication, hypoglycemia due to autologous transplant of pancreatic islet cells into the liver, and chronic kidney disease, e.g., type III, IV or V.

Other conditions of hypoglycemia are recognized in the art and are discussed below. Certain of these symptoms are observed in post-prandial hypoglycemia and can inform how to treat and monitor treatment of post-prandial hypoglycemia with the antibodies described herein.

Sulfonylurea-Induced Hypoglycemia and Insulin-Induced Hypoglycemia

Hypoglycemia is a condition characterized by abnormally low blood glucose (blood sugar) levels, usually less than 70 mg/dl, and can be life-threatening. Approximately 5-15% of all EMT calls are due to insulin-induced hypoglycemia and approximately 10% of all ED visits are due to insulin-related hypoglycemia.

Hypoglycemia can be induced by administration of certain drugs, including sulphonylurea-induced hypoglycemia and insulin itself. Insulin- and sulfonylurea-induced hypoglycemia are two of the most common types of medication-induced hypoglycemia.

Sulfonylurea-Induced Hypoglycemia is caused by sulfonylurea (SU) medication, used to treat type 2 diabetes by increasing serum insulin levels. Sulfonylureas act by stimulating insulin release from beta cells in pancreas. Currently used sulfonylureas include acetohexamide, chlorpropamide, tolazamide, tolbutamide, glibenclamide, gliclazide, glipizide, and glimepiride. Glibenclamide and chlorpropamide are associated with higher risk of hypoglycemia First-generation SUs (acetohexamide, chlorpropamide, tolazamide, tolbutamide) are more affected by drug-drug interactions that increase the risk of hypoglycemia. Second-generation SUs (glibenclamide, gliclazide, glipizide, glimepiride) have reduced likelihood of drug-drug interactions that induce hypoglycemia.

Insulin-Induced Hypoglycemia (Iatrogenic hypoglycemia) is caused by exogenous insulin administration, e.g. by an overdose of insulin which can cause a harmful decline in plasma glucose. Severe hypoglycemia occurs much more frequently in patients taking insulin than sulfonylurea compounds. Different types of insulin can cause overdose to occur: Rapid acting insulin works ~15 minutes after injection whereas regular acting insulin: works ~30 minutes after injection. In long acting insulin onset is several hours post-injection and effects last evenly over 24 hour period. Insulin overdose can occur if patient accidentally injects the wrong dose or wrong type of insulin, or misses a meal/snack after having injected an otherwise correct dose. Taking the wrong insulin product is most commonly reported by patients mixing up long-acting and rapid-acting products. Miscalculation of dietary carbohydrate content can also cause insulin overdose. Meal-related errors include neglecting to eat shortly after insulin administration or not adjusting insulin regimen in presence of reduced caloric intake. Intentional insulin overdose can also occur. A recent study found that each year in the U.S. an estimated 100,000 people go to emergency rooms because of hypoglycemia and roughly a third of these (30,000) end up hospitalized. In this study, blood glucose levels of 50 mg/dL or less were identified in over half the cases and severe neurologic manifestations in almost two-thirds (Geller A I, JAMA Intern Med. 175(5): 678-686, 2014).

Typical treatment for both SU- and insulin-induced hypoglycemia consists of consumption of 15-20 grams of glucose or simple carbohydrates. For more severe hypoglycemia glucagon and/or dextrose 50% (D50) are administered. Glucagon is unstable, not easy to prepare and acts within 10 min, but is often too short acting (20-60 min). Glucagon has multiple side-effects (flushing, vomiting, nausea) and is ineffective in high dose insulin rescue or in sustained hypoglycemia, and is contraindicated in insulinoma subjects. Glucagon requires glycogen stores which may be depleted and can be relatively easily overcome by insulin.

Dextrose is administered intravenously so it cannot be administered at a home (or school). It is viscous, has limited 'power' (e.g. for high insulin overdose) and is transient, e.g., 20% of adult hypoglycemic patients treated by EMTs will have a subsequent event within 24 hr. Dextrose also has side effects such as phlebitis and thrombosis at site of injection, hyperosmolar syndrome risk, fluid overload and rebound hypoglycemia. For insulin overdose—neither glucagon nor D50 can overcome the resulting hypoglycemia.

Nocturnal Hypoglycemia.

Nocturnal hypoglycemia is common in diabetes patients treated with insulin. Young children are particularly susceptible to severe and prolonged episodes of nocturnal hypoglycemia (Matyka et al., Horm Res. 57(suppl 1):85-90, 2002). Since blood glucose is not routinely monitored during sleep, nocturnal hypoglycemia is usually undetected, which makes it even more dangerous than daytime hypoglycemia. Nocturnal hypoglycemia usually leads to vivid dreams or nightmares, poor sleep quality or restless during sleep, morning headache, chronic fatigue, mood changes, increased muscle tone, night sweats, convulsions and enuresis in children (Stephen A Brunton, MedGenMed. 9(2):38, 2007). Frequent, undetected nocturnal hypoglycemia also contributes to hypoglycemia unawareness and causing neurocognitive deficits in long-term. Severe episodes of nocturnal hypoglycemia have been implicated as a precipitating factors in cardiac arrhythmias resulting in sudden death-the "dead-in-bed syndrome" in elderly patients (Allen K V, Frier B M. Endoc Pract. 9 (6):530-43, 2003). In fear of severe nocturnal hypoglycemia episode, patients often reduce their insulin dose before bed, which leads to inadequate glycemic control and change of morning insulin regiment. Additionally, hypoglycemia can be exacerbated in children by overexertion and physical activity combined with the difficulty in regulating food intake. Current treatment for nocturnal hypoglycemia is bedside snack for awake individuals and Glucagon for patients that can't be aroused. Antibodies herein may have application as prophylaxis in patients at high risk for severe episodes. Importantly, effective prophylaxis may permit better (tighter) glucose control (as the risk of hypoglycemia is mitigated).

Persistent Hyperinsulinemic Hypoglycemia of Infancy (PHHI) and Neonatal Hypoglycemia.

Hypoglycemia is a common metabolic issue in newborns, particularly in the first 2 days of life, and is a leading cause of admission to the NICU. Importantly, infants with prolonged low blood glucose levels are at higher risk for developmental problems later in childhood.

There is still some debate on the best approach to screen for, diagnose, and manage neonatal hypoglycemia, and to identify the levels of low glucose concentrations could be potentially damaging. Newborns at risk for, and frequently screened for hypoglycemia include late preterm, large for gestational age, small for gestational age, growth restricted, and infants of diabetic mothers. Most hypoglycemia is mild, transient and resolves without incident. Typical treatment includes supplementation with formula or, in some cases, intravenous glucose administration. A recently developed option is buccal delivery of dextrose gel.

Antibodies described herein may be useful for patients that are not responding adequately to glucose and/or in which hypoglycemia does not resolve (e.g. in the first 48 to 72 hours).

There is a higher incidence of hypoglycemia in elderly population due to altered kidney function, polypharmacy, and reduced sensitivity to warning signs. For example, the risk is twice as high in patients above 80 years old.

Treatment can be used in patients with poor response to current treatment options or in those individuals in which the current treatment is counter-indicated, e.g., venous access for dextrose solution. For example, current therapies may not be effective in individuals having glycogen depletion due to alcohol abuse or alcoholism or patients with depletion of glycogen from the liver have no expected effect with glucagon.

An alternative therapy for hypoglycemia contemplated in the field includes use of a bionic pancreas, which combine an insulin pump, continuous glucose monitoring (CGM), and automatically administer required doses of insulin, e.g., Medtronic MiniMed 670G hybrid closed-loop system. It is contemplated that a bionic pancreas could be supplemented with an antibody or Fab as described herein.

Congenital Hyperinsulinemia

Congenital hyperinsulinism is a condition that causes individuals to have abnormally high levels of insulin, resulting in frequent instances of low blood sugar (hypoglycemia). Repeated incidences of low blood sugar increase the risk for serious events such as breathing difficulties, seizures, intellectual disability, vision loss, brain damage, and coma. Mutations in several genes have been found to cause congenital hyperinsulinism and these mutations often result in over-secretion of insulin from beta cells and depletion of glucose from the blood stream.

There are currently only a few treatment approaches for persistent Congenital Hyperinsulinemia (CHI) [Arnoux J., et al. Orphanet Journal of Rare Diseases 6:63 (2011); Yorifuji T., Ann Pediatr Endocrinol Metab. 19:57-68 (2014)]. Diazoxide, a KATP channel activator, inhibits insulin secretion in pancreatic β-cells. The most frequent adverse effect is hypertrichosis (hirsutism). Other side effects include sodium and fluid retention which may precipitate congestive heart failure. Diazoxide is generally ineffective for those patients that have CHI due to KATP channel mutations, one of the most common causes of CHI. Octreotide is a somatostatin analog that inhibits insulin release. Although not approved for CHI, octreotide is utilized for diazoxide-unresponsive CHI. It is administered subcutaneously (SC) as multiple daily injections or continuously with a pump, or intravenously (IV) because of its short half-life (1 to 2 hours). Common adverse events include gastrointestinal symptoms and gall bladder complications. Partial pancreatectomy is an option for focal lesions and may be curative in a majority of the cases. However, lesions are not always visible or palpable at sites indicated by preoperative imaging. Patients with diffuse forms are primarily treated via continuous glucose feeds or off-label medications. Near-total pancreatectomy has been considered as a treatment, but this is characterized by a high risk of diabetes.

Insulinoma

Insulinoma is a tumor of the pancreas often starting in the beta cells, resulting in increased secretion of insulin. Treatment options for patients with insulinoma include medical therapy with diazoxide or somatostatin analogs to control hypoglycemic symptoms, but only surgical removal/partial pancreatectomy is curative. Insulinoma-induced hypoglycemia can recur years later after successful surgical removal (recurrence rate 5-7% in patients with sporadic insulinoma).

Approximately 5-10% of insulinomas (corresponding to ~125 new patients annually) are malignant and metastatic. Malignant insulinomas generally respond poorly to traditional chemotherapeutic agent regimens; therefore, there is a high unmet need for glycemic control in this population. In addition, an insulin-targeting treatment that could be administered simultaneously with chemotherapy to control hypoglycemia would be of interest.

Post-Prandial Hypoglycemia

Post-prandial hyperinsulinemic hypoglycemia has recently been observed as a side effect or complication of gastric bypass surgery (Singh et al., *Diabetes Spectrum* 25: 217-221, 2012; Patti et al., *Diabetologia* 48:2236-2240, 2005; Service et al. *N Engl J Med* 353:249-254, 2005). Common methods for gastric bypass surgery include the Roux-en-Y gastric bypass method (RYGB), sleeve gastrectomy (Li et al., *Surgical Laparoscopy, Endoscopy & Percutaneous Techniques* 24:1-11, 2014), gastric banding or gastroplasty. An often observed side effect of gastric bypass surgery is "dumping" which is consequence of the ingestion of simple sugars and rapid emptying of food into the small intestine. This is often characterized by vasomotor symptoms (flushing, tachycardia), abdominal pain, and diarrhea. Late dumping, or a form of reactive hypoglycemia, can occur up to a few hours after eating and results from insulin response to hyperglycemia resulting from rapid absorption of simple sugars from the proximal small intestine. In contrast to dumping, which is noted soon after surgery and improves with time, hyperinsulinemic hypoglycemia presents several months to years (usually around 1 year, up to 3 yrs) after gastric bypass surgery. This syndrome is differentiated from dumping by onset of severe post-prandial neuroglycopenia, which is typically absent in dumping, as well as pancreatic nesidioblastosis (islet cell enlargement, β-cells budding from ductal epithelium, and islets in apposition to ducts). Unlike with dumping, nutrition modification does not alleviate the symptoms of post-prandial hypoglycemia (PPH).

Diagnosis and confirmation of hyperinsulinemic hypoglycemia after bariatric surgery is often based on observation of elevated insulin (>3 μU/ml) and C-peptide (>0.6 ng/ml) and a negative oral hypoglycemic agent screen (Service F. J., *Endocrinol Metab Clin North Am* 28:501-517, 1999).

In general, hypoglycemia may be mild and lead to symptoms such as anxiety and hunger, but patients are also at risk for severe hypoglycemia, which can cause seizures, coma, and even death. Typical symptoms associated with hypoglycemia that patients complain about include tiredness, weakness, tremulous and hunger. Many patients have to eat frequently to prevent symptoms from the low blood sugar. Some patients may develop psychiatric symptoms because of the low blood sugar.

It is contemplated that administration of an antibody that is a negative modulator of insulin signaling will be beneficial in the treatment of PPH after bariatric surgery. It is contemplated that the method is useful after any of the gastric surgeries known in the art and described herein, including but not limited to, Roux-en-Y gastric bypass method (RYGB), sleeve gastrectomy, gastric banding or gastroplasty. In one aspect, the hypoglycemia/hyperinsulinemia is treated using a monoclonal antibody to the human insulin receptor (INSR) that negatively modulates insulin actions. In one aspect, the antibody has one or more of the following characteristics selected form the group consisting of binding to both forms of the INSR (A and B), inhibiting INSR auto-phosphorylation, inhibiting INSR signaling via Akt, is specific, can inhibit binding of insulin, and does not bind to IGF-1R or affect IGF-1R signaling.

It is hypothesized that an antibody contemplated for use herein will confer cellular resistance to insulin through negative modulation of the INSR, thereby increasing and normalizing blood glucose levels in hyperinsulinemic patients. In various embodiments, the antibody reduces hyperinsulinemia or excess insulin signaling. In various embodiments, the administration increases post-prandial blood glucose in the subject by 1.5 to 10 fold, or 10 to 40%. In various embodiments, the administration increases post-prandial blood glucose in the subject by approximately 10 mg/dL. In various embodiments, the administration increases blood glucose back into the normal range.

It is further contemplated that the administration stabilizes blood glucose levels for about 1, 2, 3, 4, 5, 6, 7, 8 and up to 12 hours after administration of the antibodies herein. It is also provided that the administration described herein reverses hypoglycemia in a subject without causing hyperglycemia in the subject receiving treatment.

Additionally, the kinetics for hypoglycemia following meals can be ameliorated by an antibody described herein. For example, post-meal hypoglycemia of approximately <70 mg/dL or <60 mg/dL may occur 1-4 hrs post-meal. Treatment with an antibody as described herein is contemplated to reduce such post meal levels toward normal, non-symptomatic ranges. Such reduction can be by about 10-30 mg/dL, e.g., reduction may be about 10, 15, 20, 25, or 30 mg/dL or ore, or any amount in between these numbers. Effects of administration of negative modulator antibodies to subjects are measured in vivo and in vitro. In one embodiment, it is contemplated that antibodies that negatively modulate insulin/insulin receptor activity decrease insulin sensitivity and in vivo levels of HbA1c, and glucose. These factors are measured using techniques common to those of skill in the art.

Subjects receiving a negative modulator antibody also may show improved: insulin secretion, glycemic control (as measured by glucose tolerance test (GTT) or mixed meal test (MMT)), insulin sensitivity as measured by insulin tolerance test (ITT)), beta-cell function (as measured by, e.g., cell mass, insulin secretion, C-peptide levels), beta-cell dormancy, and/or dyslipidemia.

For example, the ADA recommends a HbA1c target level of less than 7% in adults. For children, the ADA recommends higher target levels of A1c. In children younger than 6 years old, the recommended level is from 7.5% to 8.5%. In children 6 to 12 years old, the recommended level is less than 8%. the recommended level for teens 13 to 19 years old, is less than 7.5%. A1c is a measure of how well blood sugar levels have remained within a target range over the previous 2 to 3 months. (American Diabetes Association, *Diabetes Care,* 28(1): 186-212, 2005) It is contemplated that administration of an antibody to treat PPH brings A1c levels towards that observed in a non-hypoglycemic individual, e.g., increasing A1c levels in a patient by an absolute HbA1c percentage measurement of at least 0.5%, 0.7%, 1.0% or 1.5% or more. Beta cells in the pancreatic islets of Langerhans make and release insulin, a hormone that controls the level of glucose in the blood. There is a baseline level of insulin maintained by the pancreas, but it can respond quickly to spikes in blood glucose by releasing stored insulin while simultaneously producing more. The response time is fairly rapid. For example, in Type 1 diabetes, progressive and extensive loss of beta cells results in decreased levels of secreted insulin, eventually leading to hyperglycemia (abnormally high level of glucose in the blood). In Type 2 diabetes, beta cells initially compensate for insulin resistance in a subject by increasing insulin output, but, over time, the cells become unable to produce enough insulin to maintain normal glucose levels. It is thought that both resistance of target tissues to the action of insulin and decreased insulin secretion, in part due to beta cell failure, occur.

EXAMPLES

The present invention is additionally described by way of the following illustrative, non-limiting Examples.

Example 1

Construction of XPA.15.247.2.018 Variant

To construct the XPA.15.247.2.018 antibody and Fab variants, the heavy chain and light chain of XPA.15.247 (see WO2011/038302, incorporated herein by reference) were amplified and mutated using standard site-directed mutagenesis protocol using a Stratagene kit. The residues mutated in the VH were Aspartate 54 to Serine in CDR2 as it can cause isomerization with the neighboring residue Glycine. In CDR3, methionine 105 was mutated to Phenylalanine as it is a potential oxidation site. The third residue mutated was Valine 107 to Tyr. All these three residues were changed to germline (D54S, M105F, V107Y), which was intended to improve manufacturability, but surprisingly improved the affinity to the INSR and potency of the variant compared to the parent antibody. The XPA.15.247 variant heavy chain is termed XPA.15.247.2 (SEQ ID NO: 2).The heavy and light chain sequences of XPA.15.247 (SEQ ID NO: 1 and 3) and XPA.15.247.2.018 (SEQ ID NO: 2 and 4) are shown in Table 2 below, with the CDRs underlined and the amino acid modifications in bold italics.

TABLE 2

| | Sequence |
|---|---|
| XPA.15.247 VH | EVQLVETGGGVVQPGRSLRLSCAAS<u>GFT FSSYAMH</u>WVRQAPGKGLEWVAV<u>ISYDGS NKYYADSVKG</u>RFTISRDNSKNTLYLQMN SLRAEDTAVYYC<u>ARHEWGFGMDV</u>WGQGT TVTVSS (SEQ ID NO: 1) |
| XPA.15.247.2 VH | EVQLVETGGGVVQPGRSLRLSCAAS<u>GFT FSSYAMH</u>WVRQAPGKGLEWVAV<u>ISYGS NKYYADSVKG</u>RFTISRDNSKNTLYLQMN SLRAEDTAVYY<u>ARHEWGFGFDY</u>WGQG TTVTVSS (SEQ ID NO: 2) |
| XPA.15.247 VL | DVVMTQSPLSLSVTGQPASISCRSS<u>SL VYGDENTYL</u>NWFQQRPGQSPRRLLY<u>KVS DRDS</u>GVPDRFSGSGSGTDFTLKISRVEA DDVGVYYC<u>MQGTHWPYT</u>FGQGTKLEIKR TVAAPS (SEQ ID NO: 3) |
| XPA.15.247.2.018 VL | DVVMTQSPLSLPVTLGQPASISCRSS <u>QSLVYGDGNTY</u>LNWFQQRPGQSPRRL L<u>YKVSN</u>RDSGVPDRFSGSGSGTEFTLK ISRVEAEDVGVYFC<u>MQGTYWPGTFG G</u>GTKLEIKRTVAAPS (SEQ ID NO: 4) |

Example 2

Binding Assays

In order to determine the ability of the modified Fab to bind to the insulin receptor, binding assays were carried out.

CHOK1 cells over-expressing the INSR human, rat, and cyno orthologs were plated in 96-well round bottom plates (Costar, cat#3799) at 25,000 cells per well. To assess parent antibody binding, on the day before the assay, the cells were washed with PBS, resuspended at 1×10⁶ cells/mL in "Starvation Medium" containing RPMI 1640 (Invitrogen), 2 mM L-Glutamine, and 0.5% BSA, and incubated for 16-20 hours in a 37° C., 5% $CO_2$ incubator, and then incubated with concentrations of antibody ranging from 0.001 to 100 ug/ml in 50 ul FACS buffer (PBS+0.5% BSA+0.1 mM sodium azide) for 40 minutes at 4° C. For Fab staining, cells were stained with a secondary antibody, mouse anti-c-myc IgG (Roche, Basel, Switzerland). After washing twice with FACS buffer, cells were then stained with either goat anti-human IgG Allophycocyanin (Jackson Immuno Research, West Grove, Pa.) (for IgG analysis) or with goat anti-mouse IgG Allophycocyanin (Jackson Immuno Research, West Grove, Pa.) (For Fab analysis) at a 1:100 dilution for 20 minutes at 4° C. Cells were washed twice with FACS buffer and the cells were analyzed on a FACSCanto II™ flow cytometer (Becton Dickinson). Data were analyzed using both FlowJo™ (Tristar, Paso Robles, Calif.) and GraphPad Prism 5 (GraphPad Software, La Jolla, Calif.).

Figure 2:
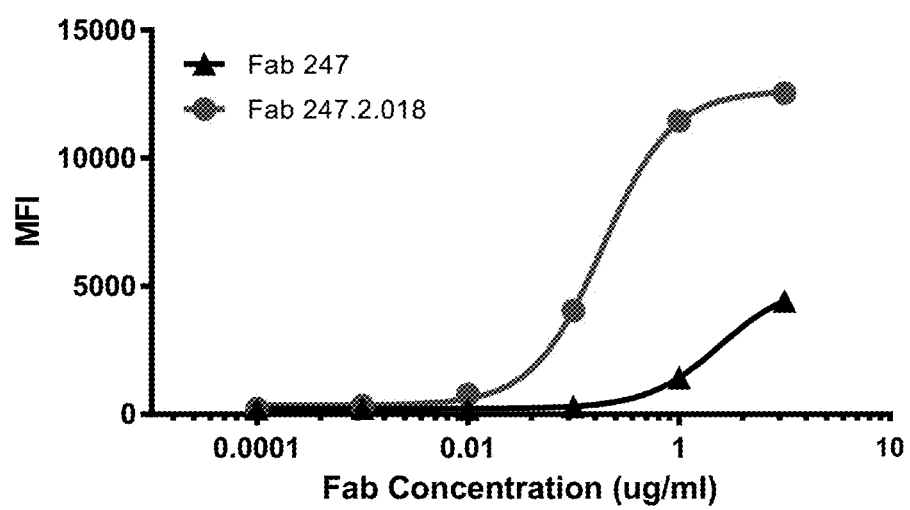
FIG. 2 depicts representative results comparing binding of XPA.15.247 parent Fab (Fab247) and its variant XPA.15.247.2.018 Fab (Fab 247.2.018) on CHO cells expressing the human INSR employing flow cytometry.

The XPA.15.247 antibody had an EC50 of 32.35, compared to 0.7514 for the XPA.15.247.2.018 antibody (FIG. 1), demonstrating that the XPA.15.247.2.018 IgG had about 43-fold higher affinity to INSR than the parent molecule. For the Fab fragments, the XPA.15.247 Fab had an EC50 of 2.530, compared to 0.1864 for the XPA.15.247.2.018 (FIG. 2), demonstrating that the XPA.15.247.2.018 Fab had a more than 13-fold higher affinity to INSR than the parent Fab.

Kinetics and binding affinity of anti-human INSR modulating antibodies were determined by surface plasmon resonance (SPR) performed on the ProteOn XPR36 instrument (Bio-Rad) at 25° C. using the one-shot kinetics method. SPR measures biomolecular interactions in real-time in a label-free environment. CHO-hINSR-B cells were solubilized in Tris lysis buffer (TLB) consisting of 150 mM NaCl, 20 mM Tris pH 7.5, 1 mM EDTA, 1 mM EGTA, and 1% Triton™ X-100 supplemented with a protease inhibitor cocktail (Roche, #05892791001). Briefly, 1 ml of TBL was added to ~2×10⁶ cells, and the cell suspensions were agitated on a rocker at 4° C. After 2 hours, this solution was centrifuged at 4° C. for 20 min at 14 000 rpm using a tabletop centrifuge. The supernatant containing solubilized INSR was filtered and kept frozen at −80° C. until it was thawed just prior to analysis. To prepare the SPR detection surface for INSR capture, CT-3 mAb (Fisher, #MS-636-PABX), which recognizes the carboxy-terminal moiety of INSR, was covalently immobilized on the sensor chip (Bio-Rad GLM, #176-5012) using standard amine-coupling chemistry. Briefly, the GLM sensor chip was preconditioned with successive injections of 10 mM SDS, 50 mM NaOH, 100 mM Tris pH 9.5, and running buffer consisting of 10 mM HEPES, 150 mM sodium chloride, 3 mM EDTA, 0.05% Polysorbate 20 (Teknova, #H8022) at a flow rate of 100 μL per min. The chip surface was then activated with a five min injection of a freshly prepared 1:1 solution of 0.1M N-hydroxysuccinimide (NHS) and 0.4 M 1-ethyl-3-(3-dimethylaminopropyl) carbodiimide at a flow rate of 25 μL per min. Following activation, 10m/mL of CT-3 antibody in pH 4.5 acetate buffer was injected at a flow rate of 30 μL per min until ~10,000 RU of the capture antibody was immobilized on the sensor surface. To block the surface, 1 M ethanolamine hydrochloride-NaOH pH 8.5 was injected for five min. Solubilized INSR diluted 1:1 in running buffer supplemented with 1 mg/ml BSA, with or without 1 μm/ml human insulin (Sigma, #A30590), was captured at a density of 1000-1200 RU on a vertical flow channel coated with the CT-3 antibody. After switching to a horizontal orientation and following 10 min of baseline stabilization, anti-human INSR modulating antibodies were injected over the captured solubilized INSR at concentrations of 133, 44, 14.7, 4.9, and 1.64 nM at a flow rate of 30 μl per min. Association was monitored for 5 min, and dissociation was monitored for 10 min. Surfaces were regenerated with 100 mM HCl following the anti-human INSR modulating antibody injections. Double-referenced data were curve fit with a simple 1:1 binding model using ProteOn™ software to yield kinetic parameters for on-rate (ka) and off-rate (kd). Equilibrium binding constant ($K_D$) values were calculated from a ratio of the kinetic parameters (kdka). Table 3 shows the binding kinetic and affinity parameters of the anti-human INSR modulating XPA.15.247 parent antibody and its variant XPA.15.247.2.018 to the human INSR in presence and absence of insulin.

TABLE 3

| Antibody | On rate ka (M-1s-1) | Off rate kd (1/s) | Affinity $K_D$ (nM) |
|---|---|---|---|
| XPA.15.247 | 3.85E+04 | 4.71E−04 | 10 ± 2 |
| XPA.15.247 + insulin | 4.25E+04 | 1.31E−03 | 29 ± 2 |
| XPA.15.247.2.018 | 1.85E+05 | 1.22E−03 | 6.6 ± 0.6 |
| XPA.15.247.2.018 + insulin | 1.96E+05 | 1.68E−03 | 8.5 ± 0.16 |

XPA.15.247 bound hINSR in the absence of insulin with an affinity of about 10 nM. The on rate was $3.8 \times 10^4$ $M^{-1}$ $sec^{-1}$ and the off-rate was $4.7 \times 10^{-4}$ $sec^{-1}$. In the presence of insulin the affinity of XPA.15.247 was ~3-fold lower (KD=29 nM). With insulin, the on-rate for XPA.15.247 binding to the hINSR was $4.25 \times 10^4$ $M^{-1}$ $sec^{-1}$ and the off-rate was $1.3 \times 10^{-3}$ $sec^{-1}$. In contrast, XPA.15.247.2.018 bound hINSR in the absence of insulin with an affinity of about 6 nM. The on rate was $1.85 \times 10^5$ $M^{-1}$ $sec^{-1}$ and the off-rate was $1.22 \times 10^{-34}$ $sec^{-1}$. In the presence of insulin, the affinity of XPA.15.247.2.018 was less than 2-fold lower (KD=8.5 nM). With insulin, the on-rate for XPA.15.247.2.018 binding to the hINSR was $1.96 \times 10^5$ $M^{-1}$ $sec^{-1}$ and the off-rate was $1.68 \times 10^{-3}$ $sec^{-1}$. The variant exhibited a higher affinity compared to the XPA.15.247 parent antibody, due to an increase in on-rate parameters. Moreover, in contrast to the parent antibody, the presence of insulin did not significantly decrease either the on-rate or the off-rate of the variant.

Example 3

Effects of Anti-INSR Modulating Antibodies on INSR-Induced Phosphorylation of AKT The INSR is a tyrosine kinase that undergoes autophosphorylation after insulin binding and subsequently catalyzes the phosphorylation of intracellular proteins such as insulin receptor substrate (IRS) family members, Shc, and Gab1. Each of these proteins serves as a docking site for the recruitment of downstream signaling molecules resulting in the activation of various signaling pathways including the PI(3)K/AKT and MAP kinase (MAPK) pathways. These pathways ultimately coordinate to regulate cell growth and differentiation, gene expression, glycogen, protein and lipid synthesis, and glucose metabolism.

The effects of a test antibody on signaling via the INS/INSR complex can be measured by assessing the ability of the antibody to augment insulin-induced serine or tyrosine phosphorylation of specific intracellular proteins, such as AKT and MAPK (ERK1/2), which are specific to the INSR signaling pathway. The phosphorylation of these proteins can be measured and quantified by electrochemiluminescence, Western blotting, ELISA, and other techniques known in the art.

CHOK1 cells engineered to express the B form of human INSR were used in the signaling assay. These cells were maintained in Growth Medium containing EX-CELL 302 Serum-Free Medium for CHO Cells (Sigma-Aldrich, St. Louis, Mo.), 4 mM L-glutamine, and 0.4 mg/mL GENETICIN® (Invitrogen, Carlsbad, Calif.). The parental CHOK1 cells were used as a control and were maintained in Growth Medium without GENETICIN®.

On the day before the assay, the cells were washed with PBS, resuspended at $1 \times 10^6$ cells/mL in "Starvation Medium" containing RPMI 1640 (Invitrogen), 2 mM L-Glutamine, 0.4 mg/mL GENETICIN®, and 0.5% BSA, and incubated for 16-20 hours in a 37° C., 5% $CO_2$ incubator. The parental CHOK1 cells were incubated in "Starvation Medium" without GENETICIN®. The next day, cells were resuspended in PBS with 0.5% BSA and $1 \times 10^5$ cells were added to wells of a 96-well plate. The test antibody was added at a saturating concentration of 500 nM, 15 minutes prior to the addition of insulin. Recombinant human insulin (rhInsulin, Sigma, St. Louis, Mo.) was then added at 7 concentrations ranging between 0.0008 and 200 nM. After incubation for an additional 10 minutes in the presence of insulin in a 37° C., 5% $CO_2$ incubator, the treated cells were centrifuged, media decanted, and cells lysed in a buffer containing 20 mM Tris-HCl (pH 7.5), 150 mM NaCl, 1 mM EDTA, 1 mM EGTA, 1% Triton X-100, 10 mM NaF, Phosphatase Inhibitor Cocktails 1 and 2 (Sigma-Aldrich), and Complete Mini Protease Inhibitor (Roche Diagnostics Corporation, Indianapolis, Ind.) for 1 hour with shaking at 4° C. The lysates were clarified by centrifugation at 485×g for 3 minutes. Electrochemiluminescence ELISA using the MesoScale Discovery Multi-spot Assay System (Meso Scale Discovery, Gaithersburg, Md.) was used to quantify the amount of phosphorylated AKT present within the lysates. Data were analyzed using GraphPad Prism® (GraphPad Software Inc., La Jolla, Calif.) software to calculate EC50 values from a 4-parameter logistic equation.

Figure 3A:
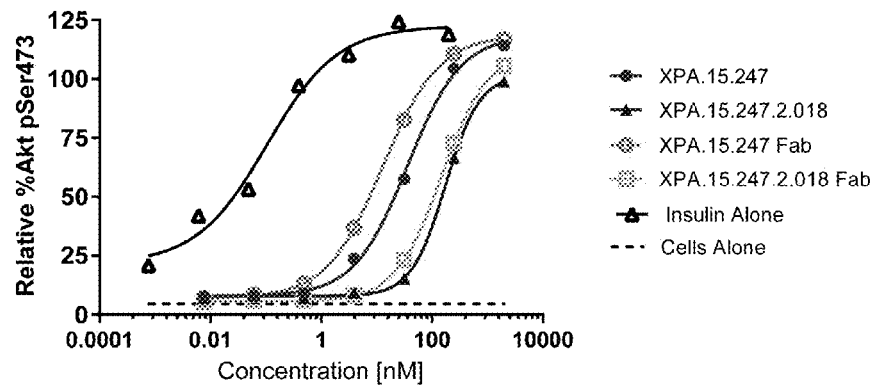
FIGS. 3A-B.
Figure 3B:
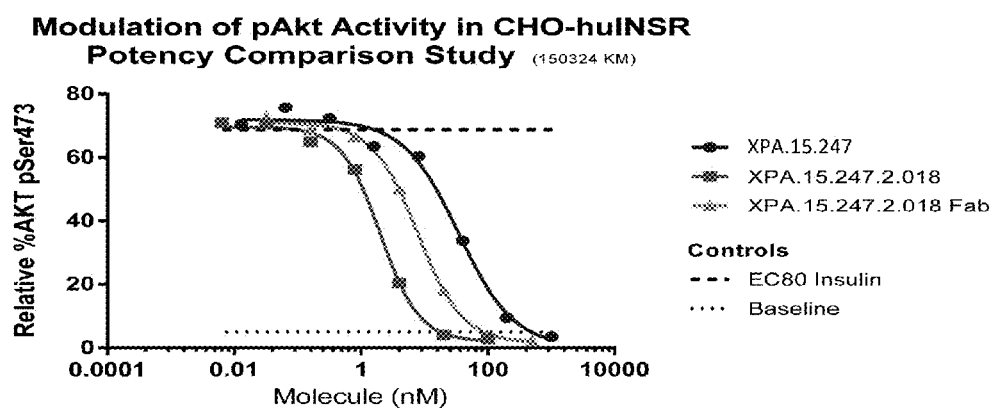

FIG. 3 shows pAKT assay results for XPA.15.247 and XPA.15.247.2.018 antibody as either an IgG antibody or a Fab fragment. Both the XPA.15.247.2.018 IgG antibody and Fab showed a markedly enhanced inhibition of insulin-mediated AKT phosphorylation. The potency of the XPA.15.247 antibody and XPA.15.247.2.018 antibody or Fab were compared at the EC80 and EC65 concentrations of insulin. At the EC80 concentration of insulin, the EC50 was 34.7 nM for the XPA.15.247 antibody, compared to 2.0 for the XPA.15.247.2.018 antibody and 7.7 for the XPA.15.247.2.018 Fab, demonstrating a more than 17-fold higher potency for the XPA.15.247.2.018 antibody and more than 4-fold higher potency for the XPA.15.247.2.018 Fab, compared to the parent antibody (FIG. 3B). The XPA.15.247.2.018 antibody and XPA.15.247.2.018 Fab also exhibited improved functional activity over the parent antibody when tested across cynomologous and rat INSR orthologs.

Example 4

Effects of Anti-INSR Modulating Antibodies on Sulphonylurea-Induced Hypoglycemia The effect of XPA.15.247.2.018 IgG and XPA.15.247.2.018 Fab on glibenclamide-induced hypoglycemia was evaluated. Wistar male rats, 7 weeks old, were fasted for 2.5 hours and then dosed with vehicle 1 (PO) or 10 mg/kg glibenclamide (PO). After 60 minutes, the animals were dosed with vehicle 2 (IV), 30 mg/kg XPA.15.247 antibody (IV), 3 mg/kg or 10 mg/kg XPA.15.247.2.018 IgG, or 3 mg/kg or 10 mg/kg XPA.15.247.2.018 Fab. The blood glucose was read before the first dosing, as well as 30 minutes, 60 minutes, 90 minutes, 120 minutes, 180 minutes, 240 minutes, 6 hours, 8 hours, 24 hours, and 48 hours post dose.

Figure 4A:
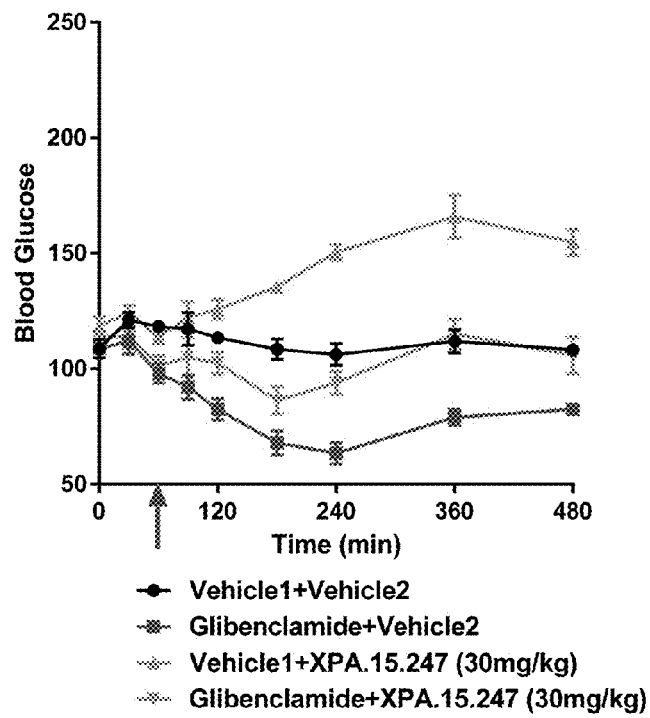
FIGS. 4A-4D.
Figure 4B:
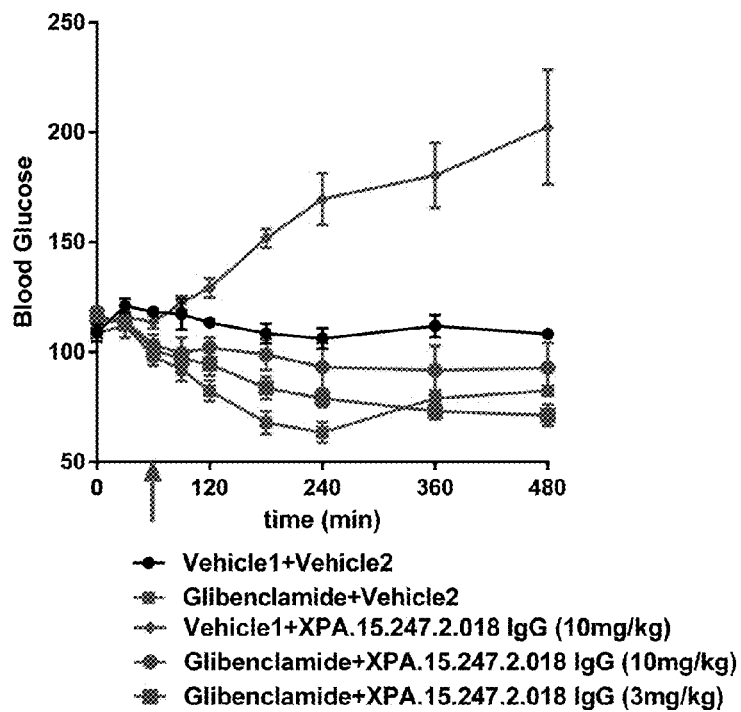
Figure 4C:
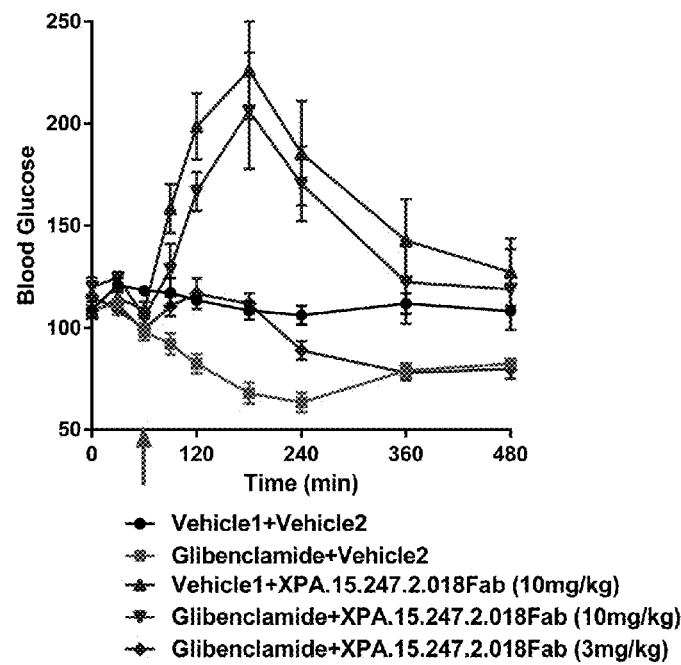
Figure 4D:
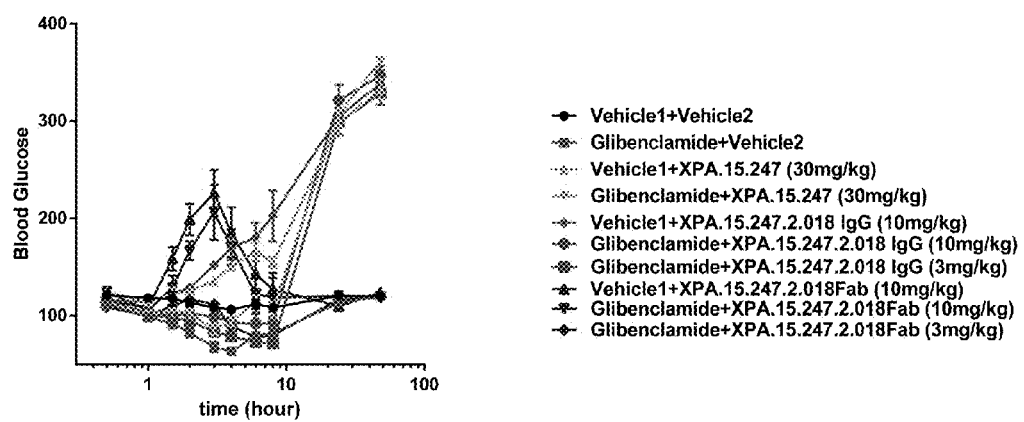

Glibenclamide induced a slow and steady decrease of blood glucose, which was reversed by 30 mg/kg XPA.15.247 antibody (FIG. 4A), which seemed to be the efficacious threshold dose. In comparison, XPA.15.247.2.018 IgG and XPA.15.247.2.018 Fab effectively reversed the hypoglycemia at both 3 mg/kg and 10 mg/kg doses in a significant dose-dependent manner (FIGS. 4B and C). In comparison with XPA.15.247 and XPA.15.247.2.018 IgG, XPA.15.247.2.018 Fab has faster onset of action (~30 minute) and shorter duration (FIG. 4D).

Example 5

Effects of Anti-INSR Modulating Antibodies on Insulin-Induced Hypoglycemia

The effect of XPA.15.247.2.018 Fab on insulin-induced hypoglycemia was also evaluated. Male Sprague Dawley rats, 7 weeks old, were fasted and then dosed with insulin (Humulin R, Eli Lilly, Indianapolis, Ind.) subcutaneously at 1 U/kg. After 20 minutes, the animals were dosed with 30 mg/kg XPA.15.247 antibody (IV) or 3 mg/kg or 10 mg/kg XPA.15.247.2.018 Fab (IV). The blood glucose was measured every 10 minutes for the first 90 minutes post insulin administration, then every 30 minutes up to 4 hours.

Figure 5A:
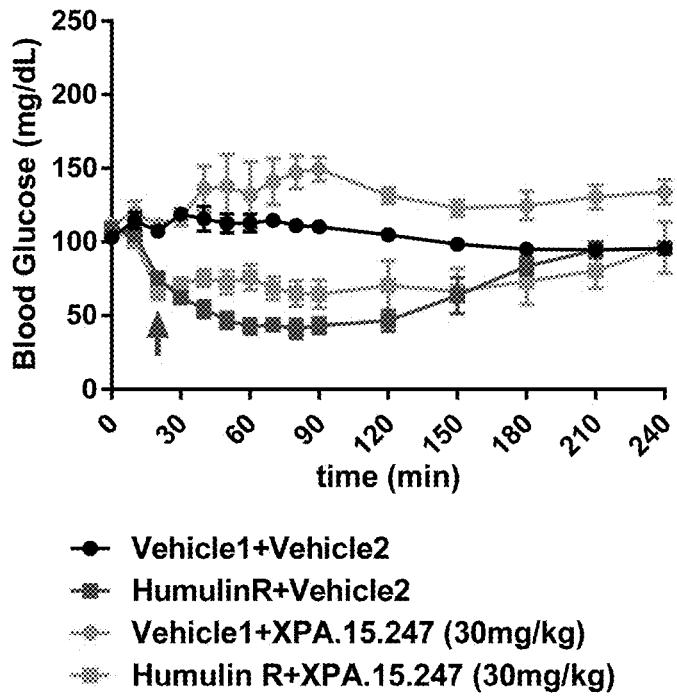
FIGS. 5A-5B.
Figure 5B:
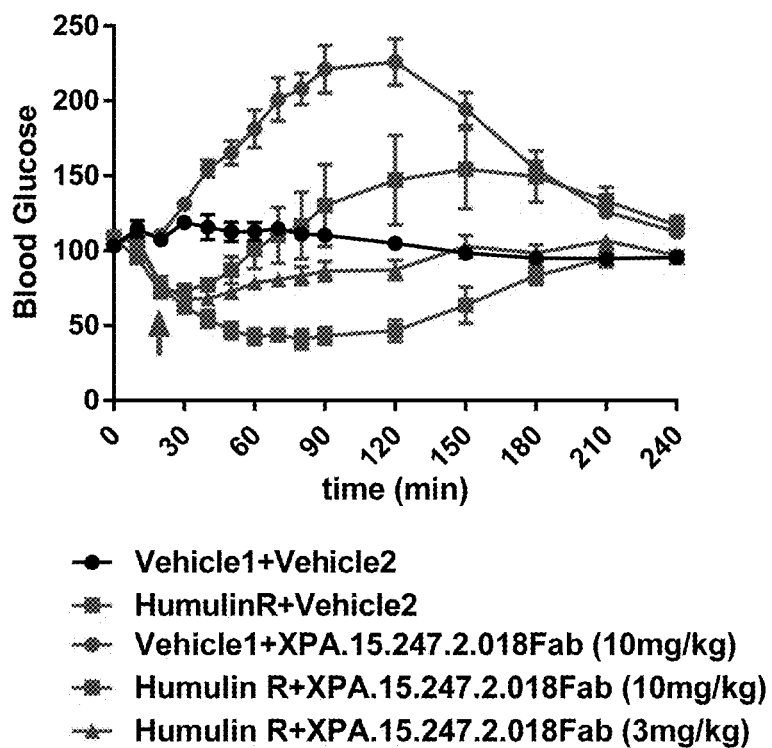

The insulin induced a rapid decrease of blood glucose. XPA.15.247 antibody effectively reversed insulin-induced hypoglycemia at 30 mg/kg (FIG. 5A). In comparison, the XPA.15.247.2.018 Fab effectively reversed the hypoglycemia at both the 3 mg/kg and 10 mg/kg doses (FIG. 5B), with rapid onset within 10 minutes after a 10 mg/kg dose and at 20 minutes following a 3 mg/kg dose. There was a significant dose-dependent efficacy observed in XPA.15.247.2.018 Fab-treated groups between 3 mg/kg and 10 mg/kg. Overall, the XPA.15.247.2.018 Fab has similar kinetics in both rat strains. In comparison to XPA.15.247 parent antibody, XPA.15.247.2.018 IgG has higher potency and XPA.15.247.2.018 Fab has faster onset of action and shorter duration.

Example 6

Additional Binding Assays

In order to determine the ability of XPA.15.247.2.018 to bind to the minipig insulin receptor, further binding assays were carried out. Two additional variants of XPA.15.247, 15.247.2.011 and 15.247.2.014, were also tested in binding assays using various insulin receptor orthologs. The binding assays were performed as described in Example 2, except that a goat anti-human kappa Fluorescein isothiocyanate secondary antibody (Life Technologies, Grand Island, N.Y.) was used to detect Fabs. The secondary antibody for experiments examining IgGs in this table was the same anti-human IgG antibody from Example 2/FIG. 1 (goat anti-human IgG Allophycocyanin (Jackson Immuno Research, West Grove, Pa.).

Table 4 shows the EC50 values in nM of XPA.15.247, XPA.15.247.2.018, and two additional variant antibodies, binding to insulin receptor orthologs.

TABLE 4

|  | human | Rat | cyno | minipig |
| --- | --- | --- | --- | --- |
| Fab |  |  |  |  |
| XPA.15.247 | 34.8 | 11.8 | 93.0 | 39.8 |
| XPA.15.247.2.018 | 1.6 | 1.9 | 21.9 | 2.0 |
| XPA.15.247.2.011 | 2.7 | 1.9 | 17.2 | 5.8 |
| XPA.15.247.2.014 | 1.8 | 1.7 | 10.2 | 2.9 |
| IgG |  |  |  |  |
| XPA.15.247 | 8.8 | 9.7 | 13.6 | 12.0 |
| XPA.15.247.2.018 | 0.3 | 0.4 | 1.4 | 0.5 |
| XPA.15.247.2.011 | 1.0 | 1.3 | 3.3 | 1.5 |
| XPA.15.247.2.014 | 0.7 | 0.7 | 1.1 | 0.9 |

Example 7

Effects of Anti-INSR Modulating Antibodies on INSR Ortholog-Induced Phosphorylation of AKT XPA.15.247 and three variant antibodies were tested in the pAKT signaling assay described in Example 3 using CHOK1 cells engineered to express various INSR orthologs, e.g., rat, monkey and minipig INSR. The results are shown in Table 5.

TABLE 5

| | EC50 (nM) | | | |
| --- | --- | --- | --- | --- |
|  | human | Rat | cyno | minipig |
| Fab |  |  |  |  |
| XPA.15.247 | 44.0 | 46.6 | 82.4 | 20.7 |
| XPA.15.247.2.018 | 3.3 | 4.2 | 2.8 | 2.5 |
| XPA.15.247.2.011 | 5.0 | 7.8 | 6.2 | 4.4 |
| XPA.15.247.2.014 | 9.6 | ~15.63 | ~15.09 | 8.4 |
| IgG |  |  |  |  |
| XPA.15.247 | 34.5 | 46.2 | 30.7 | 20.7 |
| XPA.15.247.2.018 | 0.3 | 0.4 | 0.2 | 0.3 |
| XPA.15.247.2.011 | 1.5 | 3.1 | 1.3 | 1.7 |
| XPA.15.247.2.014 | 2.1 | 4.2 | 1.7 | 2.3 |

Example 8

Kinetic Analysis of Binding of XPA.15.247 Variant Fabs to Human INSR in the Presence and Absence of Insulin Kinetic analysis of antibody binding was performed using surface plasmon resonance using the ProteOn™ XPR36 (BioRad, Hercules, Calif.). Human INSR solubilized using Tris lysis buffer (150 mM NaCl, 20 mM Tris pH 7.5, 1 mM EDTA, 1 mM EGTA, and 1% Triton™ X-100 supplemented with a protease inhibitor cocktail (Roche, #05892791001)) from CHO cells expressing the B isoform of the insulin receptor was captured on the sensor surface via an immobilized monoclonal anti-INSRβ subunit antibody (clone CT-3, Fisher, #MS-636-PABX). Increasing concentrations of Fab ranging from 3.7-300 nM were injected over the captured receptor to obtain association and dissociation kinetics. The results are shown in Table 6.

TABLE 6

| Fab | On-rate (1/Ms) | Off-rate (1/s) | Affinity (nM) |
|---|---|---|---|
| −insulin | | | |
| XPA.15.247 | 3.74E+04 | 2.11E−03 | 56 ± 3.5 |
| XPA.15.247.2.018 | 9.48E+04 | 6.55E−04 | 6.9 ± 0.4 |
| XPA.15.247.2.011 | 7.04E+04 | 7.05E−04 | 10 ± 0.3 |
| XPA.15.247.2.014 | 1.37E+05 | 7.05E−04 | 3.7 ± 0.2 |
| +insulin | | | |
| XPA.15.247 | 2.61E+04 | 2.41E−03 | 92 ± 13 |
| XPA.15.247.2.018 | 6.84E+04 | 1.18E−03 | 17 ± 1.0 |
| XPA.15.247.2.011 | 6.62E+04 | 1.08E−03 | 16 ± 0.2 |
| XPA.15.247.2.014 | 1.09E+05 | 9.98E−04 | 9.2 ± 0.2 |

Example 9 pI Measurement of XPA.15.247 Variant Fabs

Fab samples were prepared using Pharmalyte® 3-10 carrier ampholytes (GE Healthcare) according to the manufacturer's instructions. Samples were separated using cIEF Pharmalyte Basic Separation and compared to synthetic peptide pI markers (9.77, 9.5 and 6.61) or Beckman Coulter pI Markers 10.0, 7.0 or 6.7). Qualitative Analysis in the 32 Karat software was used to calculate the experimental pI value of a sample. The theoretical (naïve) and experimental (CE IEF) pI values for XPA.15.247 variant Fabs are shown in Table 7.

TABLE 7

| Fab (or IgG?) | Naïve pI value | Experimental pI value |
|---|---|---|
| XPA.15.247 | 8.41 | 7.71 |
| XPA.15.247.2.018 | 8.63 | 9.45 |
| XPA.15.247.2.011 | 8.63 | 9.47 |
| XPA.15.247.2.014 | 8.74 | 9.62 |

Example 10

Binding of XPA.15.247 Variant Fabs to Heparin

Proteins with lower pIs generally exhibit lower non-specific protein binding and therefore experience less non-specific clearance from the body. This reduced non-specific binding can have a positive effect on half-life of the molecule in vivo. See e.g., Datta-Mannan et al. (mAbs, 7:483-493, 2015), which describes that proteins with lower pIs have less binding to heparin and less non-specific clearance in vivo, but cautions that changing the charge and pI of an antibody to reduce non-specific binding can affect other properties of the antibody, such as reduced binding to target.

Figure 7:
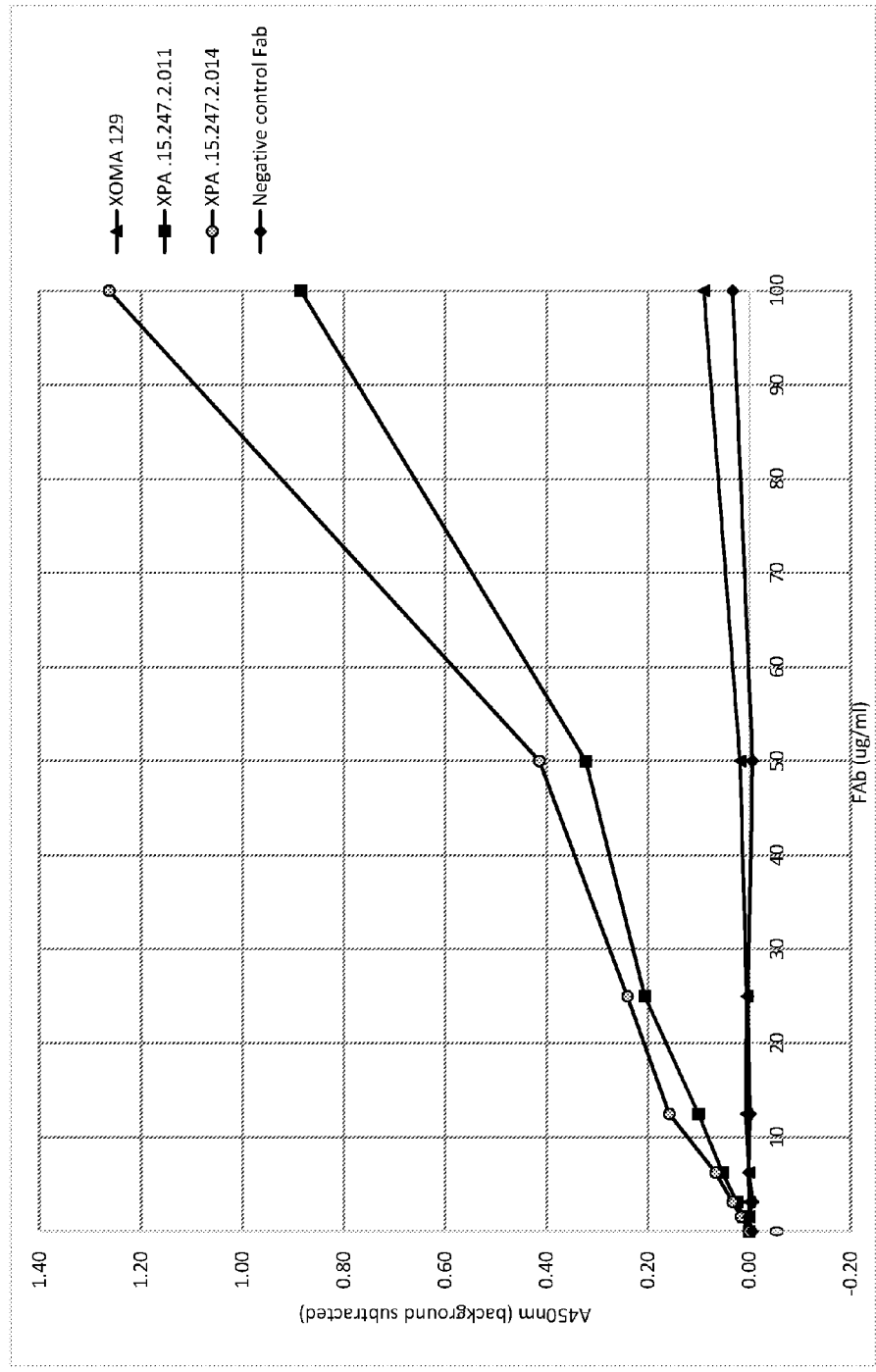
FIG. 7 shows that XPA.15.247.2.018 does not bind heparin while two other Fab variants do bind heparin non-specifically.

The relatively high pI values of the variant Fabs described herein raised the possibility that they would have high levels of non-specific binding to proteins such as heparin. Therefore, an ELISA assay for heparin binding was developed. Poly-D-lysine plates were coated with 25 ug/ml heparin (Sigma) and blocked with Casein blocker (Thermo Fisher). Test protein binding was carried out at 37° C. for 2 hours. Fabs were detected with goat anti human Fab (Caltag) diluted 1:2000 in assay buffer) followed by HRP conjugated donkey anti goat antibody (Santa Cruz Biotechnology). Recombinant IL-8 (R&D Systems) was used as a positive control, since it is known to bind heparin. IL-8 was detected with biotinylated anti IL-8 antibody (R&D Systems) followed by streptavidin HRP (Southern Biotech) diluted 1:5000 in assay buffer. The ELISA was developed with 100 μL TMB (Calbiochem) and stopped with 50 μL 2M sulfuric acid. Plates were read on a SpectraMax® Plus microplate reader (Molecular Devices) at 450 nm and background readings from a control poly-D-lysine plate were subtracted. The results are shown in Table 8 and FIG. 7.

Surprisingly, despite its relatively high pI, XPA.15.247.2.018 did not bind to heparin, in contrast to 15.247.2.011 and 15.247.2.014.

TABLE 8

| IL-8 ug/ml | Mean A450 IL-8 | Fab ug/ml | Mean A450 .018 | Mean A450 .011 | Mean A450 .014 | Mean A450 Low pI Fab |
|---|---|---|---|---|---|---|
| 1.00 | 1.03 | 100 | 0.09 | 0.88 | 1.26 | 0.03 |
| 0.50 | 0.61 | 50 | 0.02 | 0.32 | 0.41 | −0.01 |
| 0.25 | 0.23 | 25 | 0.01 | 0.21 | 0.24 | 0.00 |
| 0.125 | 0.09 | 12.5 | 0.01 | 0.10 | 0.16 | 0.00 |
| 0.063 | −0.01 | 6.25 | 0.00 | 0.05 | 0.07 | 0.00 |
| 0.03125 | 0.01 | 3.125 | 0.00 | 0.02 | 0.03 | −0.01 |
| 0.015625 | −0.05 | 1.56 | 0.00 | 0.01 | 0.02 | 0.00 |
| 0.000 | 0.05 | 0 | 0.00 | 0.00 | 0.00 | −0.01 |

Example 11

Figure 8:
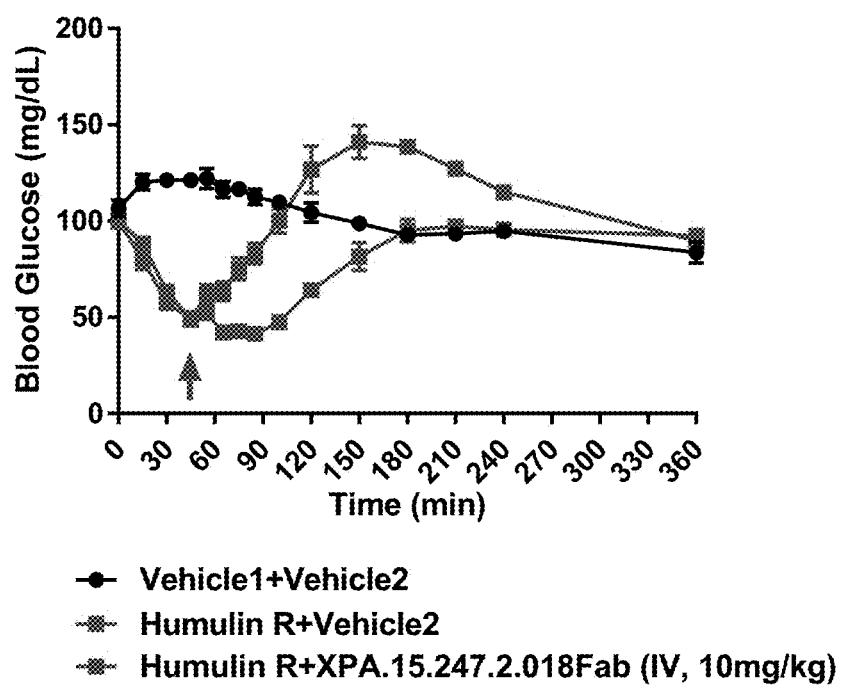
FIG. 8 shows the effect of XPA.15.247.2.018 Fab on reversing insulin-induced severe hypoglycemia.

Effects of Anti-INSR Modulating Antibodies on Severe Insulin-Induced Hypoglycemia To assess the effect of XPA.15.247.2.018 Fab on severe insulin-induced hypoglycemia, the XPA.15.247.2.018 Fab was evaluated in Sprague Dawley rats as described in Example 5, except that Fab was added 45 minutes after insulin dosing, rather than 20 minutes after insulin dosing. The results are shown in FIG. 8. XPA.15.247.2.018 Fab at 10 mg/kg effectively reversed insulin-induced severe hypoglycemia (in less than 20 minutes). The duration of effect lasted for several hours. This indicated that XPA.15.247.2.018 Fab can not only reverse insulin-induced hypoglycemia when administered early, but successfully rescue severe hypoglycemia in a timely fashion even when the blood glucose is already lower than 50 mg/dL.

Example 12

Pharmacokinetics of XPA.15.247.2.018 Fab in Rats

Figure 9A:
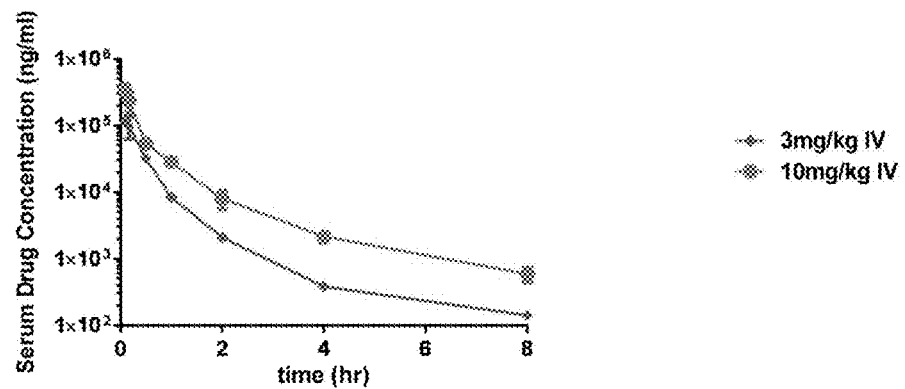
FIGS. 9A-9B show the pharmacokinetics of XPA.15.247.2.018 Fab in rat via intravenous administration.
Figure 9B:
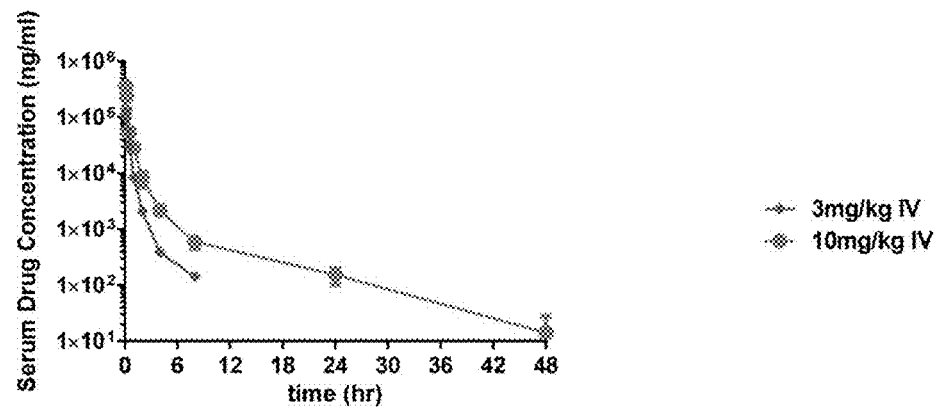

Male Sprague Dawley rats, 7 weeks old, were fasted for 2.5 hours and then XPA.15.247.2.018 Fab formulated in succinate buffer (5 mM NaSuccinate, 150 mM NaCl, pH 6.0) was administered intravenously. Samples for PK analysis were taken prior to dosing (pre-dose) and at 5 min, 15 min, 30 min, 1 hr, 2 hr, 4 hr, 8 hr, 24 hr, and 48 hr post dose. The results are shown in Table 9 and FIGS. 9A and 9B. After an intravenous administration of XPA.15.247.2.018 Fab, in general, the maximum concentrations (143 μg/ml for 3 mg/kg group and 360 μg/ml for 10 mg/kg group) was observed at the first sampling time, 5 minutes post-dose (Table 9). Serum concentrations declined thereafter with an average half-life of 4.9 hr for 10 mg/kg group and 1.4 hr for 3 mg/kg group.

TABLE 9

| Group | N | Cmax (ug/ml) | AUClast (ug*hr/ml) | Tmax (hr) | T½ (hr) | CL (ml/kg/hr) | Vss (ml/kg) |
|---|---|---|---|---|---|---|---|
| 3 mg/kg | 3 | 143 (24) | 63 (10) | ~0.1 | 1.4 (0.3) | 48 (7) | 26 (5) |
| 10 mg/kg | 3 | 360 (127) | 175 (43) | ~0.1 | 4.9 (0.5) | 59 (15) | 82 (67) |

Example 13

Pharmacokinetics of XPA.15.247.2.018 Fab in Minipigs

In order to study the effects of the XMet Fab variants in vivo, an insulin-induced hypoglycemia minipig model was used. Four male Gottingen minipigs, (approximately 10 kg) were fasted for 2.5 hours (6:00 am feeding, remove food). XPA.15.247.2.018 Fab was administered at 10 mg/kg either intravenously, intramuscularly or subcutaneously at t0. XPA.15.247.2.018 Fab was formulated in sodium phosphate buffer. Samples for pharmacokinetics were collected at the following timepoints: Pre-dose, 5, 10, 30, 60, 120, 240 min, 8 hr (return food), and 24 hr post dose.

Figure 10C:
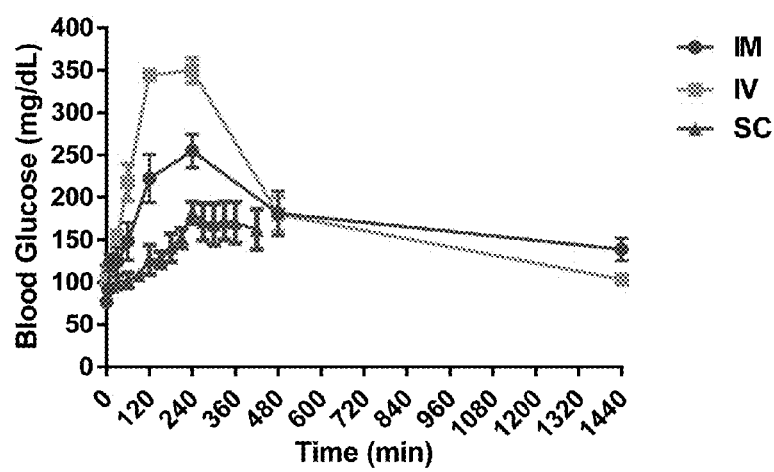

FIGS. 10A-10C show the kinetics of serum drug concentration of all three routes. With intravenous administration, XPA.15.247.2.018 Fab reached the maximum concentration at the first sampling time, 5 minutes post-dose with an average half-life of 3.3 hours. After intramuscular administration, the absorption of XPA.15.247.2.018 Fab was slower and maximum concentrations (mean—24.1 µg/mL) was observed at 2.0 h post-dose. After reaching Cmax, the serum concentrations declined thereafter with an average half-life of 5.6h and the bioavailability was 66.9%. After subcutaneous administration of XPA.15.247.2.018 Fab, the mean maximum concentration was 15.9 µg/mL, which is the lowest of the three routes, and was observed at 1.7 h post-dose, with an average half-life of 10.5 h and the bioavailability of 65.5%. In conclusion, comparing to IV administration of XPA.15.247.2.018 Fab, IM and SC administration of XPA.15.247.2.018 Fab yielded a later $T_{max}$, lower $C_{max}$.

Effect of XPA.15.247.2.018 Fab in normal minipig was measured by the change of blood glucose (FIG. 10C). Four male Gottingen minipigs, (approximately 10 kg) were fasted for 2.5 hours. XPA.15.247.2.018 Fab was administered at 10 mg/kg either intravenously, intramuscularly or subcutaneously at t0. Blood glucose was measured at the following timepoints for intravenous and intramuscular routes: Pre-dose, 5, 10, 30, 60, 120, 240 min, 8 hr, and 24 hr post dose; and at the following time points for subcutaneous route: pre-dose, 15 minutes, 30 minutes, 1 hour, 1.5 hour, 2 hours, 2.5 hours, 3 hours, 3.5 hours, 4 hours, 4.5 hours, 5 hours, 5.5 hours, 6 hours and 7 hours post dose. As shown in FIG. 10C, intravenous administration of XPA.15.247.2.018 Fab elevated blood glucose the most, up to 350 mg/dL, subcutaneous administration elevated blood glucose the least, only 150 mg/dL, and intramuscular administration in the middle with 250 mg/dL. The effect of XPA.15.247.2.018 Fab lasted about 8 hours in minipigs. This is correlated closely with the PK result as IV route has the highest Cmax and SC route has the lowest Cmax.

Example 14

Efficacy of XPA.15.247.2.018 Fab in Humulin R-Induced Hypoglycemia in Minipigs A minipig experiment was carried to evaluate the effects of the Fab variant after administration of long acting insulin (Humilin R, Eli Lilly, Indianapolis, Ind.). Four male Gottingen minipigs, (approximately 10 kg) were fasted for 2.5 hours (6:00 am feeding, remove food). Insulin (Humulin R) was administered subcutaneously (s.c.) at 0.15 U/kg for pigs 7083, 7084, 7086 and 0.1 U/kg for pig 7085. XPA.15.247.2.018 Fab was administered intramuscularly at 20 min post insulin dosing. Blood glucose levels were measured at the following timepoints: Pre-dose, 10, 20, 30, 40, 50, 60, 75, 90, 105, 120, 150, 180, 210, 240, 270 min, 6 hr (return food), and 24 hr post dose. Rescue of the minipig was carried out if blood glucose level was equal to or below 40 mg/dL. Rescue was performed by feeding pig marshmallow. If more than one marshmallow were needed to increase blood glucose, it was considered a separate rescue event. Results are shown in Table 10. (* Blood glucose reading equal to or below 40 mg/dL.)

TABLE 10

| Minipig | Humulin R (S.C.) t = 0 min | XPA.15.247.2.018Fab (I.M.) t = 20 min | Rescue Needed* (with marshmallow) |
|---|---|---|---|
| 7083 | 0.15 IU/kg | N/A | none |
|  |  | 10 mg/kg | none |
| 7084 | 0.15 IU/kg | N/A | none |
|  |  | 10 mg/kg | none |
| 7085 | 0.1 IU/kg | N/A | 30 min, 40 min |
|  |  | 10 mg/kg | none |
| 7086 | 0.15 IU/kg | N/A | 30 min |
|  |  | 10 mg/kg | none |

These results suggest that XPA.15.247.2.018 Fab rapidly blunts the decrease of blood glucose caused by Humulin R and prevents blood glucose level dropping below 40 mg/dL.

Example 15

Efficacy of XPA.15.247.2.018 Fab in Rescuing Vetsulin-Induced Hypoglycemia in Minipigs Via Different Administration Routes Four male Gottingen minipigs, (approximately 10 kg) were fasted for 2.5 hours (6:00 am feeding, remove food). Either Vetsulin at 0.5 IU/kg (Purified Porcine Insulin) or vehicle control was administered subcutaneously (s.c.) at t0. Blood glucose level was measured at various time points (every 30 minutes for the first 2 hours and then every 20 minutes from 2 hours to 5 hours, then at 5.5, 6, 6.5, 7 and 8 hours for Vetsulin groups; every 20 minutes for the first 5 hours, then at 5.5, 6, 6.5, 7 and 8 hours for vehicle control group).

Figure 11A:
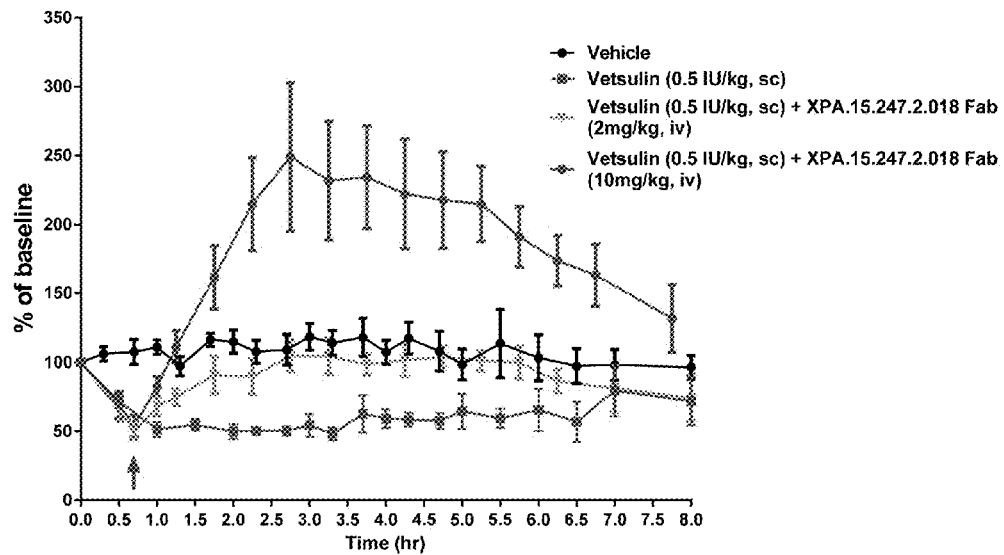
FIGS. 11A-11C show the reversal of Vetsulin-induced hypoglycemia in normal Gottingen minipigs via single intravenous, intramuscular or subcutaneous administration of XPA.15.247.2.018 Fab.

Vetsulin rapidly lowered blood glucose and it reached 50 mg/dL at t45 minutes, and maintained at that level for about 6 to 7 hours. XPA.15.247.2.018 Fab was administered intravenously at either 10 mg/kg or 2 mg/kg dose at t45 minutes. The blood glucose was measured every 15 minutes for the first 2 time points post XPA.15.247.2.018 Fab administration and every 30 minutes to t6 hours and at 7 hours. XPA.15.247.2.018 Fab effectively reversed Vetsulin-induced hypoglycemia within 15 minutes at both doses and showed significant dose-dependent effect (FIG. 11A). XPA.15.247.2.018 Fab at 2 mg/kg not only was efficacious, but also stabilized blood glucose at euglycemia in minipigs that lasted for more than 6 hours. This indicates that with the right dosage, intravenous administration of XPA.15.247.2.018 Fab can stabilize blood glucose without causing significant fluctuations.

Figure 11B:
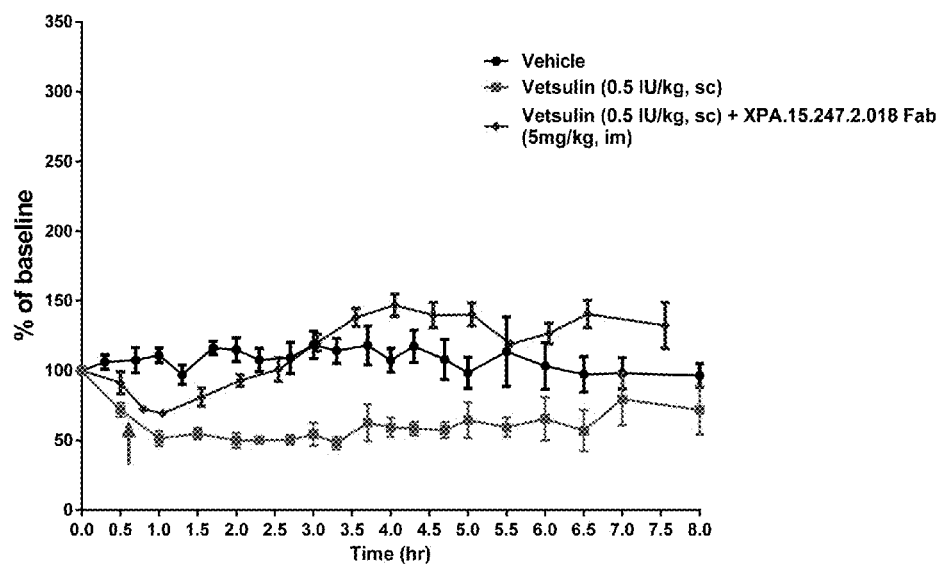

XPA.15.247.2.018 Fab at 5 mg/kg was administered via intramuscular injection at t35 minutes post-Vetsulin. The blood glucose was measured every 15 minutes for the first 2 time points post XPA.15.247.2.018 Fab administration and every 30 minutes to t6 hours and at 7 hours. XPA.15.247.2.018 Fab at 5 mg/kg effectively slowed the drop of blood glucose within 15 minutes and started to reverse the hypoglycemia within about 30 minutes post administration (FIG. 11B). The effect was sustained for several hours. Although there was slight elevation of the blood glucose after 4 hours, it did not exceed 150 mg/dL. This indicates that XPA.15.247.2.018 Fab have sufficient bioavailability via intramuscular administration to slow the blood glucose drop caused by insulin and to reverse severe hypoglycemia without causing hyperglycemia. The success of XPA.15.247.2.018 Fab via intramuscular injection provides a route that could be easily used by both medical professionals and non-medical personnel.

Figure 11C:
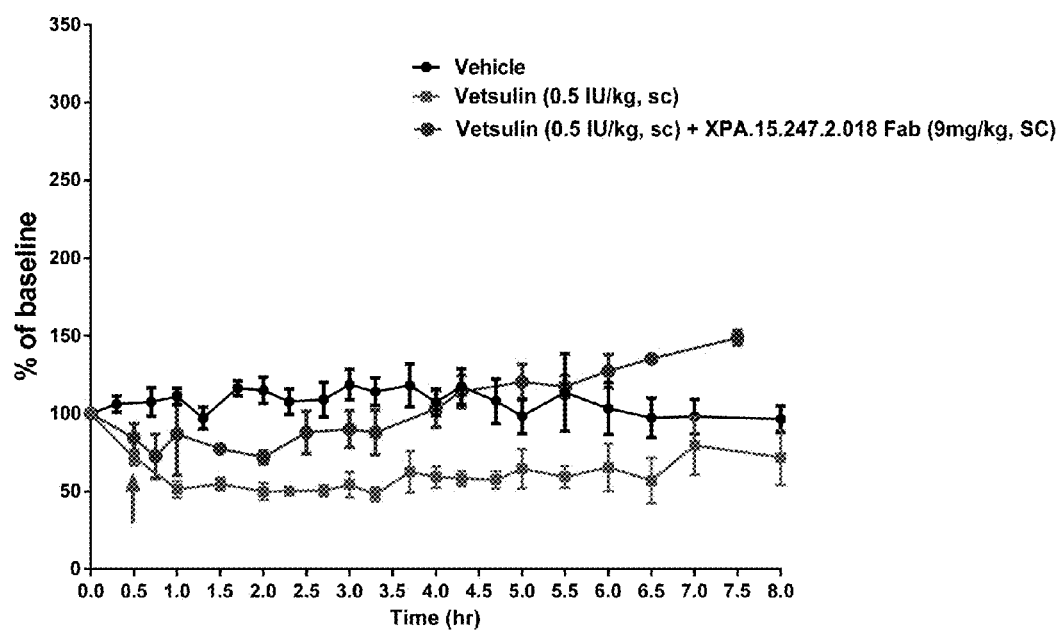

The effect of XPA.15.247.2.018 Fab was also tested via subcutaneous injection in this model. XPA.15.247.2.018 Fab at 9 mg/kg was administered subcutaneously at t30 minutes post Vetsulin. The blood glucose was measured every 15 minutes for the first 2 time points post XPA.15.247.2.018 Fab administration and every 30 minutes to t6 hours and at 7 hours. As showed in FIG. 11C, XPA.15.247.2.018 Fab via subcutaneous administration blunt the blood glucose drop caused by insulin, but only elevated the blood glucose over Vetsulin alone control group within 30-60 min post-administration.

Example 16

Figure 12:
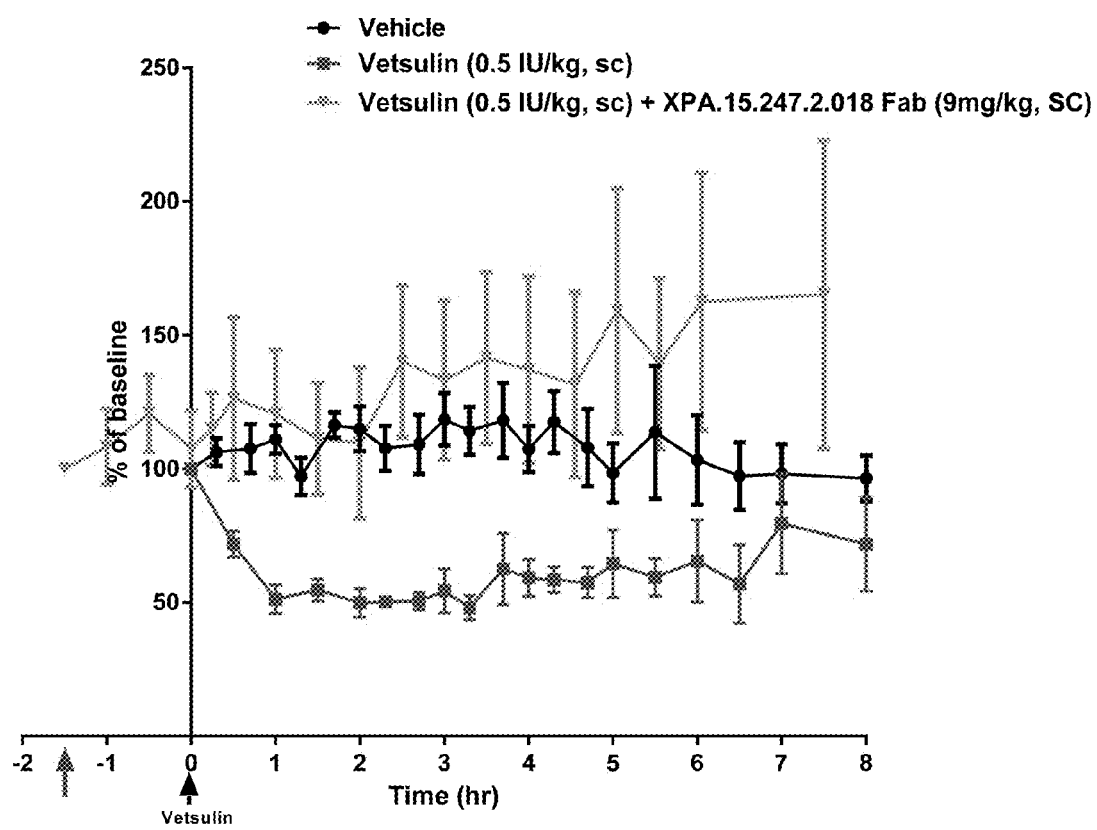
FIG. 12 shows the prevention of Vetsulin-induced hypoglycemia in normal Gottingen minipigs via single subcutaneous administration of XPA.15.247.2.018 Fab at 9 mg/kg.

Efficacy of XPA.15.247.2.018 Fab in Preventing Vetsulin-Induced Hypoglycemia in Minipigs Via Subcutaneous Administration Route The duration and severity of Vetsulin-induced hypoglycemia in minipigs represents a good model for nocturnal hypoglycemia in humans. Therefore, it was also used to evaluate the effect of XPA.15.247.2.018 Fab in preventing nocturnal hypoglycemia. Four male Gottingen minipigs, (approximately 10 kg) were fasted for 2.5 hours (6:00 am feeding, remove food). XPA.15.247.2.018 Fab was administered subcutaneously at t-90 minutes at 9 mg/kg. Vetsulin at 0.5 IU/kg was administered subcutaneously (s.c.) at t0. The blood glucose was measured every 15 minutes for the first 2 time points post XPA.15.247.2.018 Fab administration and every 30 minutes to t6 hours and at 7 hours. As shown in FIG. 12, XPA.15.247.2.018 Fab via subcutaneous administration successfully prevent insulin-induced hypoglycemia. There was no significant blood glucose elevation after XPA.15.247.2.018 Fab administration at any time points during the study. This indicates that subcutaneous administration of XPA.15.247.2.018 Fab can effectively prevent nocturnal hypoglycemia without the risk of causing hyperglycemia.

Example 17

Efficacy of XPA.15.247.2.018 IgG with Repeat-Dosing in Normal Rats

Figure 13A:
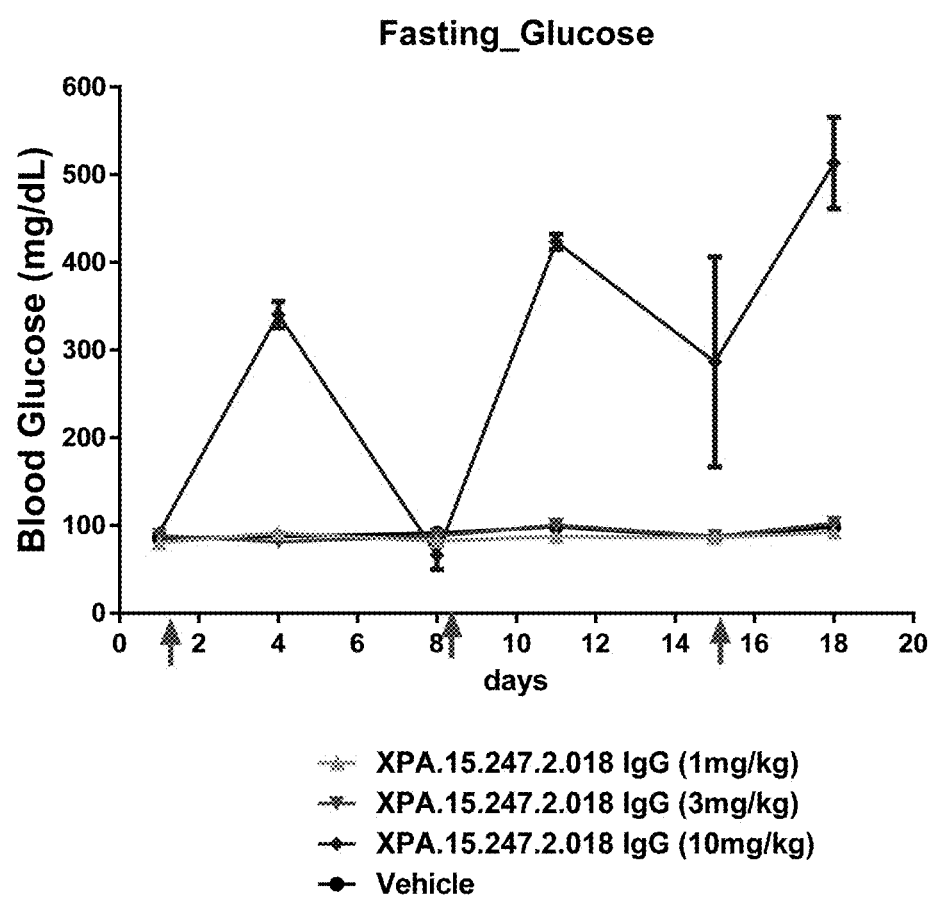
FIGS. 13A-13B show the fasting and fed blood glucose levels in Sprague Dawley rats after intravenous administration of the XPA.15.247.2.018 IgG once every week.
Figure 13B:
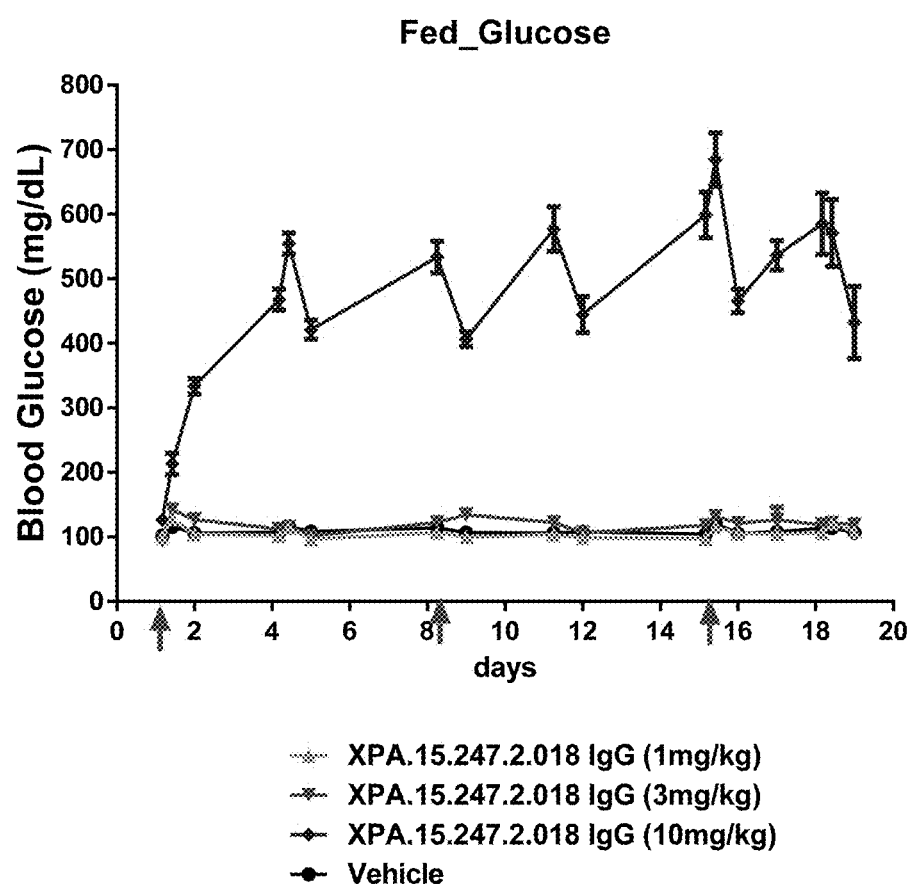

To test the effect of repeat administration of XPA.15.247.2.018 IgG, XPA.15.247.2.018 IgG was administered intravenously to normal Sprague Dawley rats at 1 mg/kg, 3 mg/kg and 10 mg/kg once a week for three weeks. Serum samples were collected and blood glucose levels were measured at various time points either under 8-hour fasting condition or under fed condition. Fasting serum samples and glucose reading were collected at pre-dose, day 4, day 8, day 11, day 15 and day 18 post dose (samples from day 8 and day 15 were pre-second dose and pre-third dose). The fed serum samples and glucose readings were collected at 4 hours, 8 hours, day 2, day 4+4 hours and day 4+10 hours, day 5, day 8+6 hours, day 9, day 11+6 hours, day 12, day 15+4 hours, day 15+10 hours, day 16, day 17, day 18+4 hours, day 18+10 hours and day 19. XPA.15.247.2.018 IgG at 10 mg/kg caused significant hyperglycemia under fasting condition (FIG. 13A) at most of the time points. Improved glucose elevation efficacy was also observed upon multi-dose administration of XPA.15.247.2.018 IgG. XPA.15.247.2.018 IgG caused even more severe hyperglycemia under fed condition at 10 mg/kg (FIG. 13B). However, the blood glucose levels in 1 mg/kg and 3 mg/kg groups were not significantly elevated under fasting conditions and with inconsistent minor elevation in 3 mg/kg group under fed condition (FIGS. 13A and B).

Figure 14A:
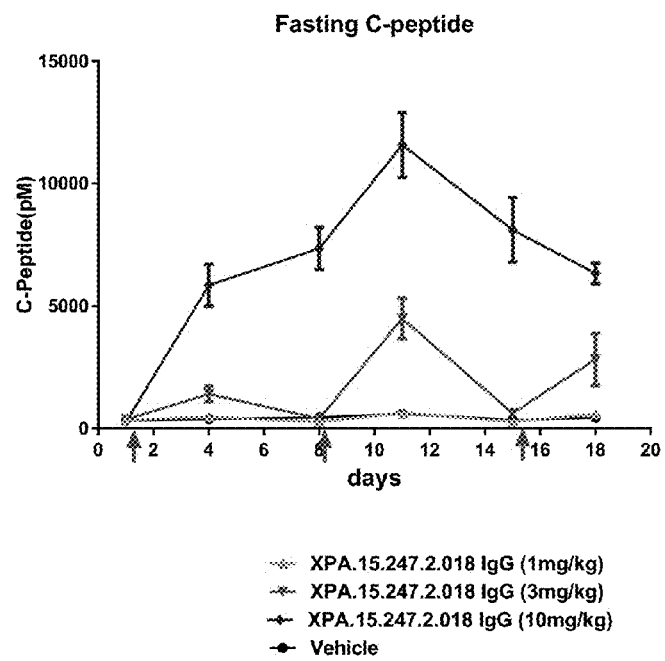
FIGS. 14A-14D show C-peptide and insulin levels during fasting and fed conditions in Sprague Dawley rats after intravenous administration of the XPA.15.247.2.018 IgG once every week.
Figure 14B:
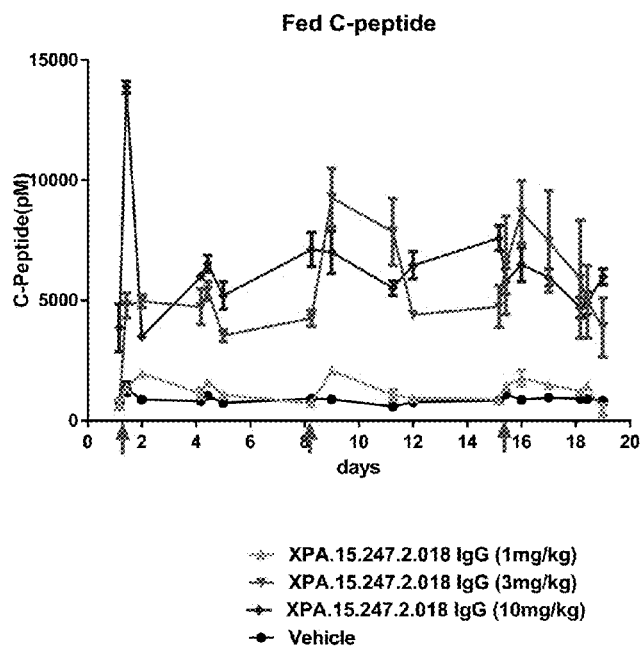

Serum samples were analyzed for c-peptide and insulin levels at all time points. XPA.15.247.2.018 IgG elevated c-peptide levels in a dose-dependent manner (FIG. 14A) under fasting condition and particularly at dose levels wherein glucose was elevated, consistent with a normal physiological response. However, a similar trend was not observed under fed condition. C-peptide levels showed an initial spike at t10 hours post first dose, then were maintained at a steady level (around $5\text{-}6\times10^3$ pM) for both dose groups (FIG. 14B).

Figure 14C:
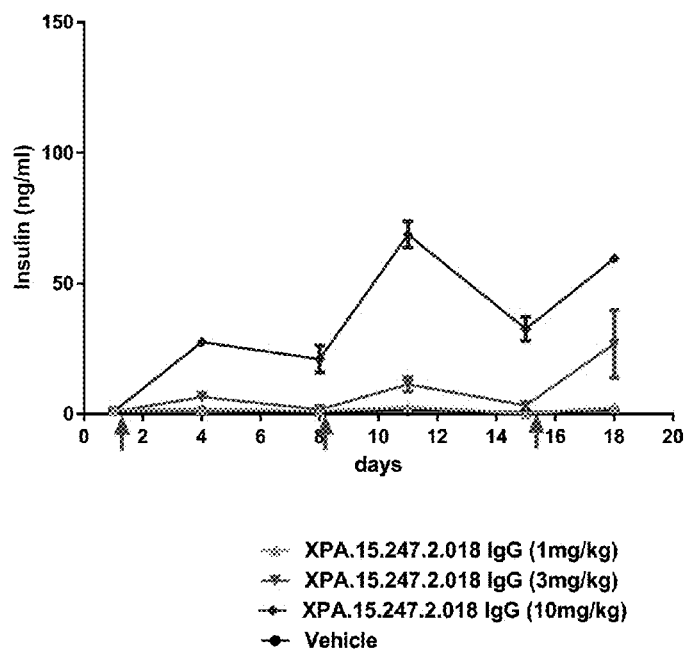
Figure 14D:
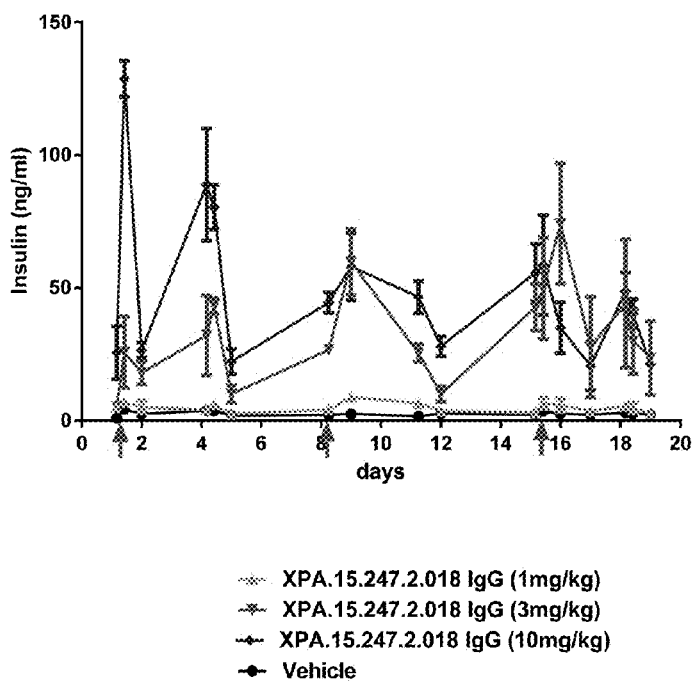

As for insulin levels, XPA.15.247.2.018 IgG also elevated endogenous insulin levels in a dose-dependent manner under fasting condition (FIG. 14C). The peak concentration of insulin level coincided with the peak of c-peptide (FIGS. 14 A and C) at 10 mg/kg dose. However, under fed condition, the insulin levels are almost overlapped between 10 mg/kg and 3 mg/kg groups in week 2 and 3 (FIG. 14D). A significant elevation in insulin level in the 10 mg/kg group was observed, which correlated with the c-peptide levels (FIG. 14B).

Despite the minimal change in blood glucose at 3 mg/kg, XPA.15.247.2.018 IgG significantly elevated both c-peptide and endogenous insulin levels suggesting threshold glucose elevation and with sensitive counter-regulatory insulin secretion.

Figure 15A:
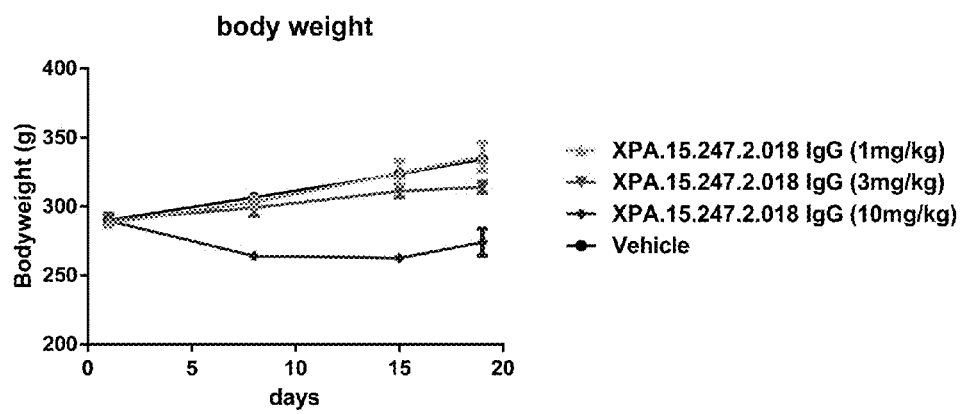
FIGS. 15A-15C show the changes in body weight and weight changes in liver and kidneys after repeated intravenous administration of the XPA.15.247.2.018 IgG once every week for 3 weeks.
Figure 15B:
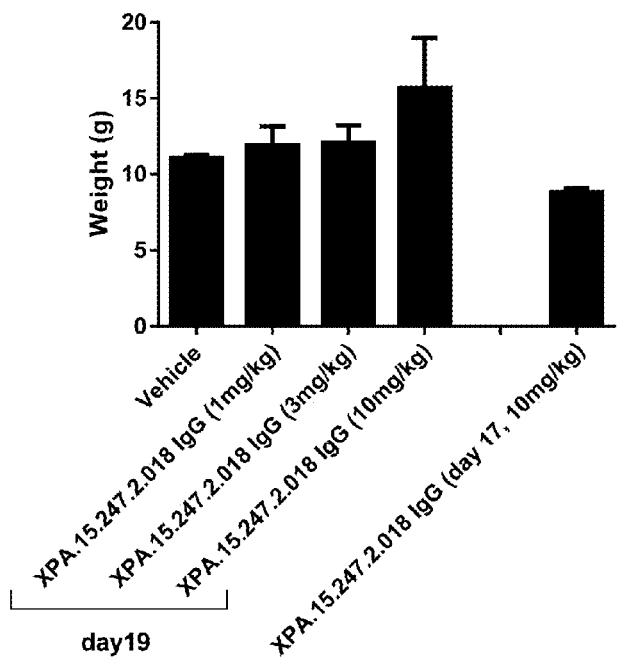
Figure 15C:
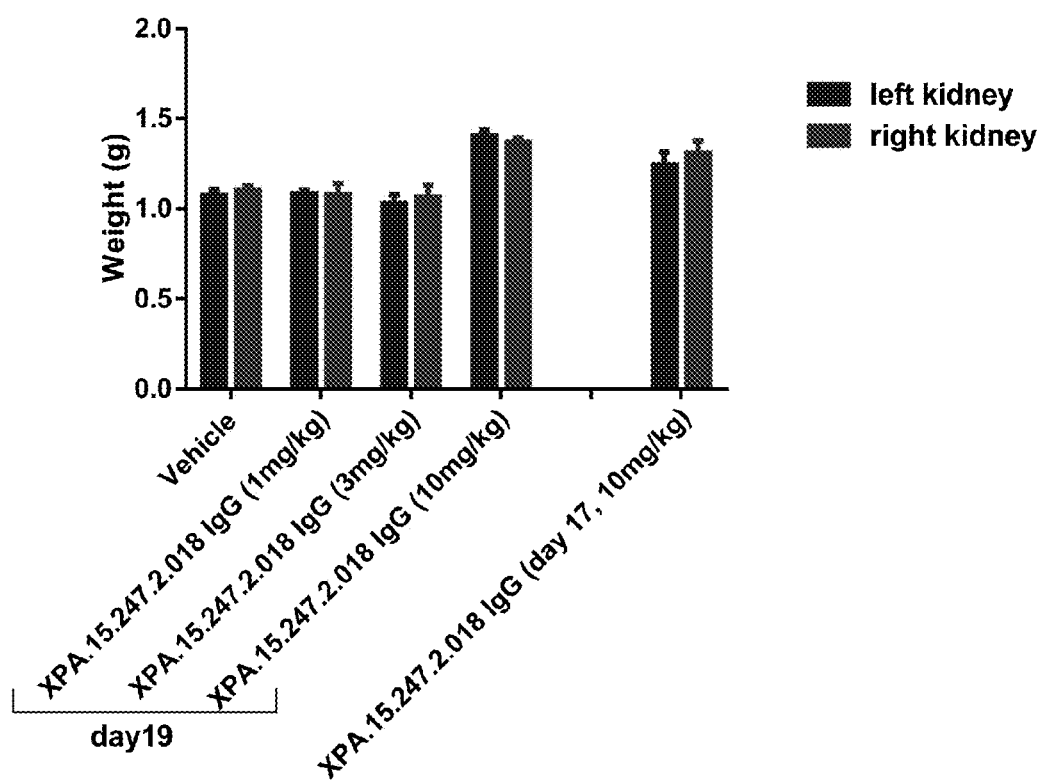

The body weight change during the study was recorded and organs collected (liver and kidney) at the end of the study. XPA.15.247.2.018 IgG did cause some weight loss at the first week in 10 mg/kg group (FIG. 15A). Then, the animals maintained the body weight at the second week and started to gain weight at a similar rate as the rest of the group during the third week (FIG. 15A). XPA.15.247.2.018 IgG at 3 mg/kg showed a trend of less weight gain compared to the 1 mg/kg group and vehicle control group. Based on the mechanism of action of XPA.15.247.2.018 IgG, liver is considered as a target organ with its rich insulin receptor expression. No significant weight change was observed in the livers among all the groups (FIG. 15B). However, there was a slight increase in the weight of the kidneys in the 10 mg/kg groups (FIG. 15C) at the end of the study. Therefore, with 3 repeated dosing of XPA.15.247.2.018 IgG at 10 mg/kg, initial weight loss was observed, which tended to recover as the study continued. XPA.15.247.2.018 IgG did not significantly impact liver weight in this study and only caused slight increase in weight of kidneys.

Example 18

Efficacy of XPA.15.247.2.018 Fab with Repeat-Dosing in Normal Rats

Figure 16A:
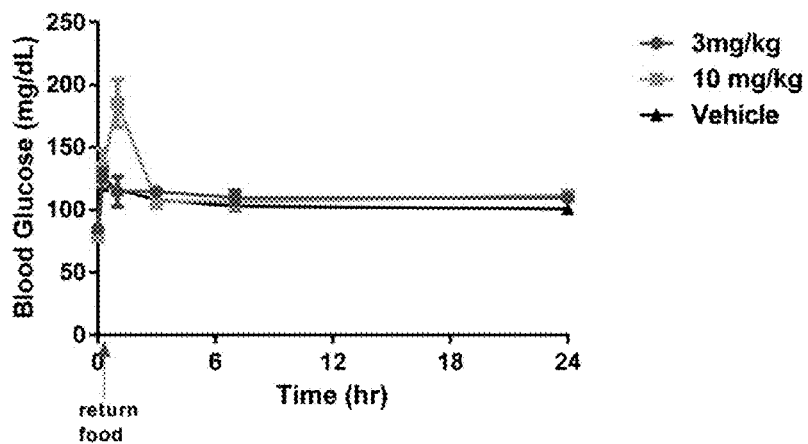
FIGS. 16A-16B show the fasting and fed blood glucose levels in Sprague Dawley rats after intravenous administration of the XPA.15.247.2.018 Fab once a day.
Figure 16B:
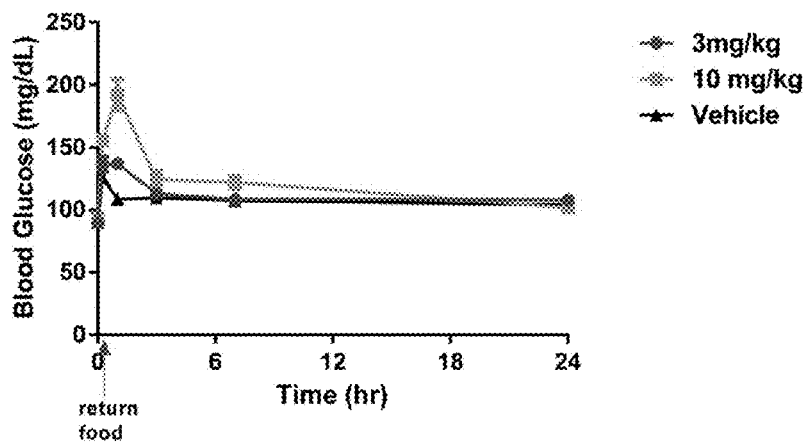
Figure 17A:
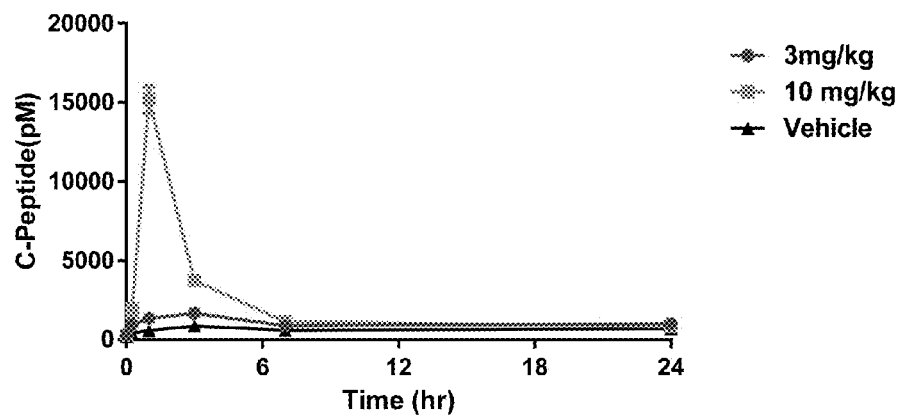
FIGS. 17A-17D show C-peptide and insulin levels in Sprague Dawley rats after intravenous administration of the XPA.15.247.2.018 Fab once a day for 3 days.
Figure 17B:
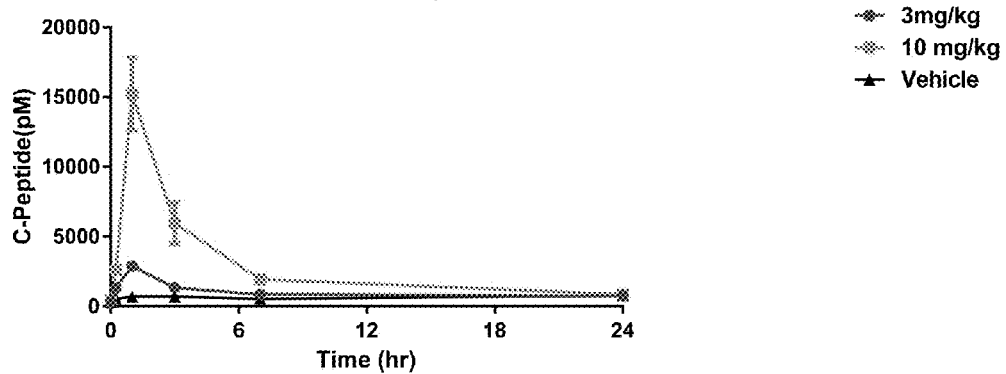
Figure 17C:
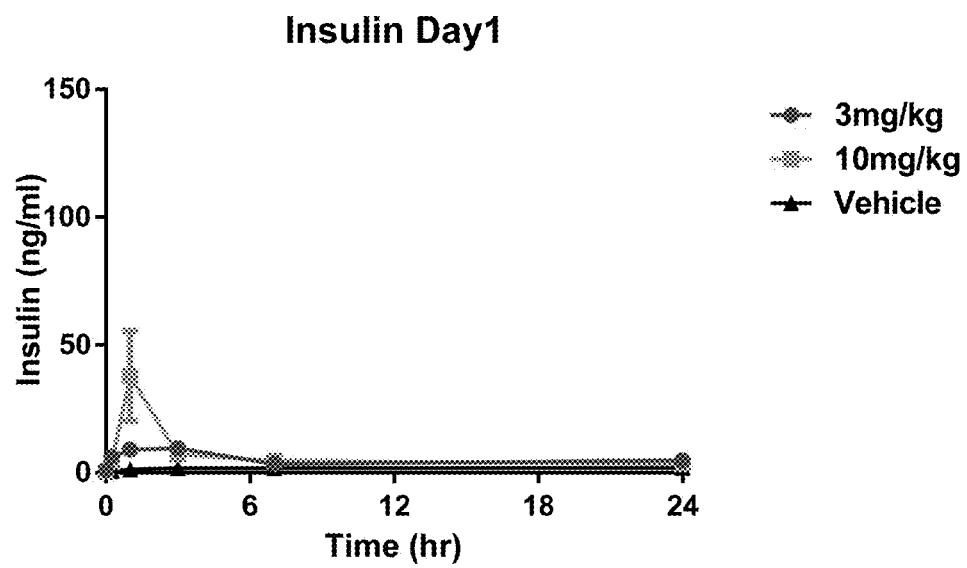
Figure 17D:
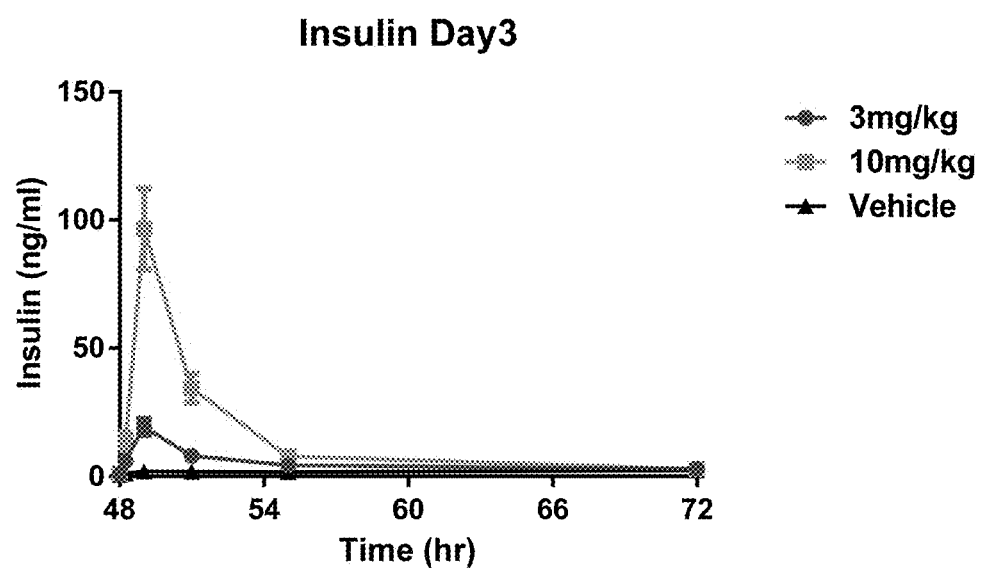

To test the effect of repeat administration of XPA.15.247.2.018 Fab, it was administered intravenously to normal Sprague Dawley rats at 3 mg/kg and 10 mg/kg once a day for three days. Serum samples were collected and blood glucose levels were measured at various time points under a 8-hour fasting condition or under a fed condition. Fasting serum samples and glucose reading were collected at pre-dose, day 3 (pre-third dose). The fed serum samples and glucose readings were collected at 15 minutes, 1 hour, 3 hours and 7 hours, and day 2 (pre-second dose), day 3+15 minutes, day 3+1 hour, day 3+3 hours, day 3+7 hours and day 4. XPA.15.247.2.018 Fab did increase blood glucose level at both 10 mg/kg and 3 mg/kg dose levels and its effects lasted for several hours (FIGS. 16A and B). XPA.15.247.2.018 Fab did not cause any change in blood glucose levels 24 hours post dose (FIGS. 16A and B) nor did it increase the levels of c-peptide and insulin (FIGS. 17A, B, C and D). However, significant elevation of c-peptide and insulin levels were observed during the elevation of blood glucose (FIGS. 17A, B, C and D), which was in a dose-dependent manner.

Figure 18A:
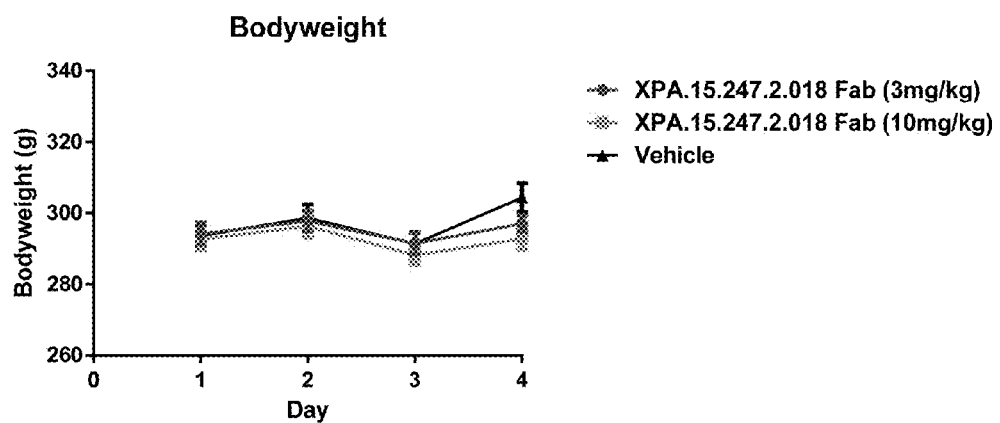
FIGS. 18A-18C show the changes in body weight and weight changes in liver and kidneys after repeated intravenous administration of the XPA.15.247.2.018Fab once a day for 3 days.
Figure 18B:
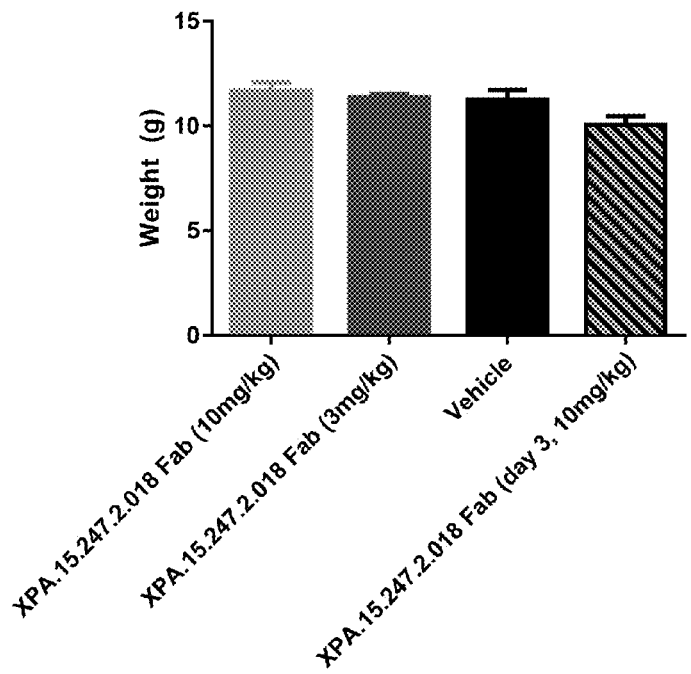
Figure 18C:
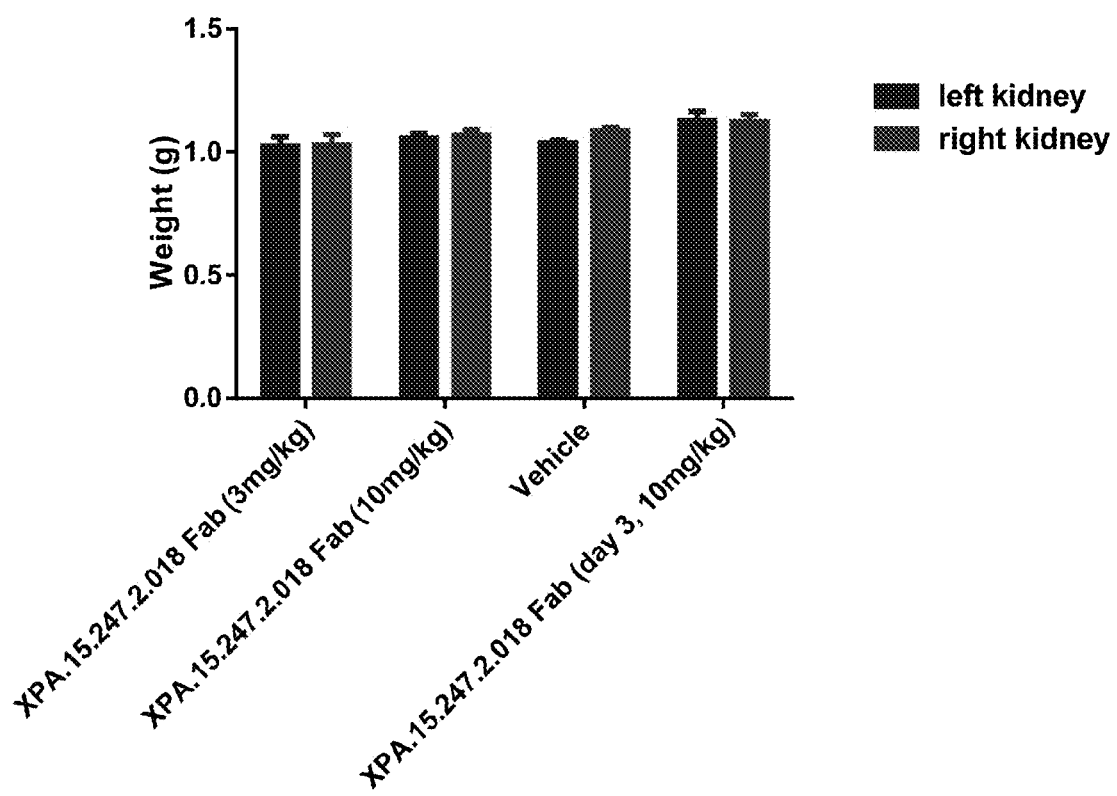

No significant change in animals' body weight was observed throughout the study, nor was any change in the weight of livers and kidneys observed at the end of the study (FIGS. 18A, B and C). Therefore, XPA.15.247.2.018 Fab has minimal impact on the body weight of the animals and liver and kidney weights even at 10 mg/kg dose level.

Example 19

Pharmacokinetics of XPA.15.247.2.018 IgG

Serum samples collected during XPA.15.247.2.018 IgG repeat-dosing study were also used to analyze the serum drug concentration to understand the pharmacokinetics of XPA.15.247.2.018 IgG. The results are shown in Table 11. After an intravenous administration of XPA.15.247.2.018 IgG, the maximum concentrations were observed at the first sampling time point, 5 minutes post-dose (336.7 µg/ml for 10 mg/kg group and 126 µg/ml for 3 mg/kg group). Serum concentrations declined thereafter with an average half-life of 3.8 days for 10 mg/kg group and 1.2 day for 3 mg/kg group.

TABLE 11

|  | n | Cmax (ug/ml) | AUC(ug*hr/ml) | Tmax (hr) | t½ (h) | t½ (day) |
|---|---|---|---|---|---|---|
| 10 mg/kg | 3 | 336.7 | 13457.2 | 10 | 91 | 3.8 |
| 3 mg/kg | 3 | 126 | 2862.2 | 10 | 29 | 1.2 |

Example 20

Affinity Maturation of Clone XPA247.2.018 Heavy Chain Variable Region

XPA15.247.2.018 heavy chain variable region was subjected to affinity maturation to increase its affinity and potency against hINSR. A library of sequence variants generated by targeted affinity enhancement (TAE) of heavy chain was panned using Biotinylated h-INSR. All residues in the VH CDR1, CDR2 and CDR3 were mutated. Each residue was replaced with NHT, VAA, and BGG. These degenerate primers yielded 18 mutants except Cysteine and Methionine (See U.S. Pat. No. 9,102,711).

The desired mutation region was kept in the middle of the primer and about 20 bases of correct sequences on both sides flanking the mutation. Overlap PCR of all four fragments was performed in order to generate H1+H2+H3 CDR combination libraries. A full length fragment was digested with Asc1/Not1 restriction enzyme and ligated into pXHMV31 Kappa phagemid vector and transformed into TG1 cells containing the chaperone cytFKPA.

Three rounds of soluble panning using HC TAE library were performed. For the first round of phage panning, $1.3 \times 10^{9}$ cfu of phage particles were blocked for 1 hour at RT in 1 ml of 5% non-fat dry milk (Marvel, Premier Foods, UK) in PBS buffer with gentle rotation. Blocked phage were twice deselected for 45 minutes against streptavidin-coated magnetic DYNABEADS® M-280 (Invitrogen Dynal AS, Oslo, Norway) blocked with 5% milk in PBS. Biotinylated receptor was captured on deselected Dynal beads to remove un-biotinylated receptor. The amount of biotinylated h-INSR was reduced in each successive round of panning in order to increase stringency.

Selection was done by incubating deselected phage with beads bound by biotinylated h-INSR for one hour at room temperature with gentle rotation, 20 RPM in a KINGFISHER96® system (Thermo Fisher Scientific, Waltham, Mass.) was used for washing beads and eluting phage. Receptor bound phage was washed with PBS-0.05% Tween followed by PBS. The duration of washes was increased in each successive round of panning in order to increase the stringency of selection. In addition, an overnight wash with 100× cold receptor was added.

The h-INSR-bound phage were eluted by incubation for 30 minutes with 100 mM triethylamine (TEA) at room temperature and subsequently neutralized with 1M Tris-HCl (pH 7.4). The phage eluted from each round of panning was used to infect TG1 bacterial cell expressing cyt-FkpA chaperone variant (Levy et al. 2013 J. Immun. Meth. 394(1-2): 10-21) when the $OD_{600}$ was equal to 0.5. TG1 cells were grown in 2YT media supplemented with 34 ug/ml chloramphenicol. Infection was done for 1 hour at 37° C. Cells were spun and cell pellets were resuspended in 2YT growth media supplemented with 100 µg/ml carbenicillin and 2% (w/v) glucose. Resuspended cells were plated on 2YT agar plates containing 100 µg/ml carbenicillin, 34 ug/ml chloramphenicol and 2% glucose and incubated overnight at 30° C.

Phage was rescued with M13K07 helper phage (New England Biolabs) at a multiplicity of infection (MOI) 20. First and second round selection output clones were grown to an OD600~0.5. Cells were infected with helper phage at 37° C. for 1 hour while shaking at 100 RPM. Following infection, cells were spun and cell pellets were re-suspended in 2YT media supplemented with 100 µg/ml Carbenicillin, 50 µg/ml kanamycin and 0.2% arabinose in order to allow the expression of the chaperone cytFkpA and allowed to grow overnight at 25° C. Following overnight growth of bacterial cultures at 25° C., phage was harvested following centrifugation at 4° C. and then PEG-precipitated to be used as input for the next round of panning.

In order to estimate the enrichment resulting from the phage selections, the amount of input and output phage were titered and plated on 2YT agar plates supplemented with the appropriate antibiotics.

Periplasmic Extract (PPE) Preparation:

Clones were picked from Rd3 output and grown in 2YT growth media supplemented with 34 µg/ml chloramphenicol, 100 µg/ml Carbenicillin and 0.1% (w/v) glucose. Clones were allowed to grow for 2-3 hours ~OD600-0.5 and then 0.2% Arabinose was added and the culture was grown at 30° C. After 30 min, isopropyl 3-D-1-thiogalactopyranoside (IPTG) was added to a final concentration of 1 mM and incubated overnight at 25° C. Cells were pelleted and re-suspended in 75 µl ice-cold PPB sucrose buffer (Teknova) at 1:4 dilution and one tablet of EDTA-free protease inhibitor cocktail (Roche). Following incubation at 4° C. for 1 hour, samples were centrifuged for 30 min and the supernatants containing the periplasmic extracts were collected. PPE were then used to screen h-INSR binders by SPR and FACS.

Affinity Ranking of Fab Periplasmic Extracts:

In order to identify Fab fragment variants with enhanced binding affinity to the insulin receptor, a direct binding surface plasmon resonance (SPR) approach was used.

SPR analysis was performed on the Biacore 4000 (GE Healthcare) at 25° C. SPR measures biomolecular interactions in real-time in a label-free environment. Recombinant human insulin receptor (B form) ECD (R&D Systems, Minneapolis Minn.) was used for the SPR analysis. To prepare the SPR detection surface, INSR-ECD was covalently immobilized on the Series S CM5 sensor chip (GE Healthcare) using standard amine-coupling chemistry (reagents used from Amine Coupling kit-GE Healthcare) with a modified protocol including a reactivation step which is detailed below. At a flow rate of 10 µL/minute, the chip surface was activated with a 10 minute injection of a freshly prepared 1:1 solution of 0.1M N-hydroxysuccinimide (NHS) and 0.4 M 1-ethyl-3-(3-dimethylaminopropyl) carbodiimide (EDC). Following activation, 10 µg/mL of the INSR-ECD in 10 mM sodium acetate pH 4.5 was injected at a flow rate of 10 pt per min for 7 minutes and achieved ~4,000 RU of immobilized protein. Next the sensor surface was reactivated with further 5 minute injection of freshly mixed EDC/NHS. This served to further stabilize the immobilized protein complex. The surface was then blocked with, 1 M ethanolamine hydrochloride-NaOH pH 8.5 for 7 minutes. The running buffer for immobilization was 1×HBS-EP+running buffer consisting of 10 mM HEPES, 150 mM sodium chloride, 3 mM EDTA, 0.05% Polysorbate 20 (Teknova, Hollister Calif.).

Periplasmic extracts containing Fabs of interest were diluted 1:1 with HBS-EP+ containing 5 mg/mL BSA, filtered through a 0.2 µM Millex GV filter plate (Millipore) and injected at 30 µL/minute for 240 seconds with a 300 second dissociation. Regeneration after each PPE injection was performed using two 50 second injections of 3M $MgCl_2$. The running buffer used was HBS-EP+with 2.5 mg/mL BSA (Sigma Aldrich, St. Louis Mo.). The stability early report point in the BIACORE 4000 software was used to evaluate PPE binding levels and calculate the dissociation rate constants ($k_d$).

Clones with improved off-rates, or high binding responses suggestive of an improved on-rate, were identified and selected for further analysis. The $k_d$ cutoffs used for selection ranged from $5\times10^{-4}$ to $2.3\times10^{-4}$ (1/s) depending on the distribution of the improved clones in each assay.

Affinity Measurement of Purified Fab Fragment:

In order to measure the on-rate (ka) and off-rate (kd) constants for the various purified Fab fragments, an SPR approach was pursued.

SPR analysis was performed on the Biacore 2000 (GE Healthcare) at 25° C. To prepare the SPR detection surface, INSR-ECD was covalently immobilized on the CMS sensor chip and the chip was activated as described above. Following activation, 10m/mL of the INSR-ECD in 10 mM sodium acetate pH 4.5 was injected at a flow rate of 10 µL per min for 2 minutes and achieved ~1,400 RU of immobilized protein. Next the sensor surface was reactivated and blocked as described above. The running buffer for immobilization was 1×HBS-EP+Kinetic analysis was performed by injecting the Fabs at 40 µL/minute for 240 seconds followed by a 300 second dissociation. Fabs were injected in at least two concentrations of 200 nM and 40 nM. Regeneration after each PPE injection was performed using one 60 second injection of 3 M MgCl2, followed by one 7.5 second injection of 10 mM Glycine pH 2.0. Buffer blank injections were used to double-reference these data (both a control spot and a blank injection were subtracted). These data were then curve fit with a 1:1 binding model using the SCRUBBER 2 (BioLogic Software, Campbell Australia) evaluation software to yield kinetic parameters for on-rate ($k_a$) and off-rate ($k_d$). Equilibrium binding constant ($K_D$) values were calculated from a ratio of the kinetic parameters (kd/ka).

Sixteen clones were selected based on Off rate analysis. A 2-4 fold improvement in comparison to XPA.247.2.018 parent from PPE screen was observed in certain clones. Five additional clones were selected based on Ru binding The twenty-one clones were reformatted into untagged Fabs. Affinity matured Heavy chains were paired with LC 18 for transfections into Expi 293 cells.

Sequences of the affinity matured heavy chain clones are set out in FIG. 19. FIG. 19 also shows the affinity and potency of the different affinity matured clones. The identified affinity mutants had improvements over the parental XPA.15.247.2.018 Fab in both on and off-rates.

Detection of Mutation Hot Spots:

From the additional screening, trends in mutation hot spots in heavy chain CDR1 and CDR3 emerged. Amino acid residue Threonine 28 in HCDR1 was mostly frequently mutated to K and R residues and was mutated in approximately 77% of the selected clones. These mutations and frequency suggest that it has a positive impact on improved $k_{off}$.

Small libraries were made to incorporate only these two residues and T was included as a parental residue (T, K and R). For HCDR3, Phenylalanine 103, Phenylalanine 105 and Tyrosine 107 amino acid residues were mutated 10%, 28% and 52% respectively in selected clones. These three FFY residues were able to mutate to all 20 amino acids, i.e., NNS. Mutation of Tyrosine 107 to R/E suggests the R/E has a positive impact on improved $k_{off}$. The mutation frequency show in FIG. 20 suggests that Q and K could also contribute to improvement. Mutation of Phenylalanine 105 to tyrosine has a strong correlation with improved $k_{on}$, based upon 4 of the 5 clones with improved $k_{on}$ in FIGS. 19 and 20 have this mutation (068,072,075,079) and the clone lacking this mutation (084) has a poor improvement in $k_{on}$. Tryptophan was also observed at this position suggesting an improved affinity from this residue also. Position 103 is not heavily mutated, but based upon the mutation frequency observed, 107, 105 and 103 are likely positions of interaction with the target.

Since mutations were preferred at these hot spots, a new library was designed to combine all these mutations. Combination of two or more of these mutations will probably show a synergistic effect.

Importantly, the HCDR2 was retained as a TAE library with up to 1 mutation per CDR2. The mutation frequency table shows significant mutations across CDR2, but the contribution to binding is unclear. However, the mutation frequency in FIG. 19 does show what amino acids are tolerated within a particular position within the higher affinity pool of antibodies that were selected.

Numerous modifications and variations in the invention as set forth in the above illustrative examples are expected to occur to those skilled in the art. Consequently only such limitations as appear in the appended claims should be placed on the invention.

What is claimed:

1. An antibody or fragment thereof comprising three heavy chain CDRs having the amino acid sequence set out in SEQ ID NOs: 5-7, 8-10 and 50-112 and three light chain CDRs have the amino acid sequences set out in SEQ ID NOs: 14-16 or SEQ ID NOs: 20-28 wherein the antibody or fragment thereof binds to i) insulin receptor or (ii) a complex comprising insulin and insulin receptor, or both (i) and (ii).

2. An antibody or fragment thereof of claim 1 wherein the heavy chain variable region amino acid sequence is set out in SEQ ID NOs: 1, 2 or 29-49, and the light chain variable region amino acid sequence is set out in SEQ ID NOs: 4 or 17-19.

3. The antibody fragment of claim 1 which is a Fab fragment.

4. The antibody or antibody fragment of claim 1, wherein said antibody is a human antibody.

5. An antibody or fragment thereof comprising three heavy chain CDRs having the amino acid sequence set out in SEQ ID NOs: 8-10 and three light chain CDRs have the amino acid sequences set out in SEQ ID NOs: 14-16, wherein the antibody or fragment thereof binds to i) insulin receptor or (ii) a complex comprising insulin and insulin receptor, or both (i) and (ii).

6. The antibody or fragment thereof of claim 5 wherein the heavy chain variable region amino acid sequence is set out in SEQ ID NO: 2 and the light chain variable region amino acid sequence is set out in SEQ ID NO: 4.

7. The antibody fragment of claim 5 wherein the heavy chain variable region amino acid sequence is set out in SEQ ID NO: 1 or 2 and the light chain variable region amino acid sequence is set out in SEQ ID NO: 3 or 4.

8. An antibody fragment comprising three heavy chain CDRs having the amino acid sequences set out in SEQ ID NOs: 5-7 or 8-10 and three light chain CDRs having the amino acid sequences set out in SEQ ID NOs: 11-13 or 14-16, wherein the antibody fragment binds to i) insulin receptor or (ii) a complex comprising insulin and insulin receptor, or both (i) and (ii).

9. The antibody fragment of claim 8 or 7 wherein the three heavy chain CDRs have the amino acid sequences set out in SEQ ID NOs: 8-10 and three light chain CDRs have the amino acid sequences set out in SEQ ID NOs: 14-16.

10. The antibody fragment of claim 8 wherein the heavy chain variable region amino acid sequence is set out in SEQ ID NO: 2 and the light chain variable region amino acid sequences is set out in SEQ ID NO: 4.

11. A sterile composition comprising the antibody of any of one of claims 1 to 3 and 4, and a sterile pharmaceutically acceptable diluent.

12. A method of treating hypoglycemia, comprising administering to a subject in need thereof an antibody fragment according to claim 1, that is a negative modulator of insulin binding to the insulin receptor and/or insulin action at the insulin receptor in an amount effective to ameliorate hypoglycemia.

13. The method of claim 12, wherein the hypoglycemia is selected from the group consisting of sulfonylurea-induced hypoglycemia, insulin-induced hypoglycemia, nocturnal hypoglycemia, hypoglycemia following post-bariatric surgery, and hypoglycemia in subjects with inherited metabolic and insulin sensitivity disorders.

14. A method for treating nocturnal hypoglycemia comprising administering to a subject in need thereof an antibody fragment according to claim 1, that is a negative modulator of insulin binding to the insulin receptor and/or insulin action at the insulin receptor in an amount effective to ameliorate nocturnal hypoglycemia.

15. The method of any one of claims 12 to 14 wherein the antibody fragment comprises three heavy chain CDRs set out in SEQ ID NOs: 5-7, 8-10 or 50-112 and three light chain CDRs set out in SEQ ID NOs: 11-13, 14-16 or 20-28.

16. The method of any one of claims 12 to 14, wherein the antibody fragment comprises a heavy chain variable region selected from the group consisting of SEQ ID NO: 1 or 2 and a light chain variable region selected from the group consisting of SEQ ID NO: 3 or 4.

17. The method of claim 14, wherein the antibody fragment is from a human antibody.

18. The method of claim 14, wherein the antibody fragment is a Fab fragment.

19. The method of claim 14, wherein the antibody fragment reduces hyperinsulinemia or excess insulin signaling in the subject.

20. The method of claim 14, wherein the subject has a blood glucose level of less than 70 mg/dL prior to administration.

21. The method of claim 14, wherein the antibody fragment is administered at a dose of from 0.1 to 25 mg/kg.

22. The method of claim 14, wherein the antibody fragment is administered in a single bolus, once every 12 hours or once per day, until hypoglycemia is eliminated.

23. The method of claim 14, wherein the antibody is administered intravenously, intraarterially, intraperitoneally, intramuscularly, intradermally, subcutaneously or orally.

24. The method of claim 14, wherein administration increases blood glucose in the subject by 1.5 to 10 fold or by 10 to 40%, optionally wherein administration increases blood glucose in the subject by at least 10 mg/dL.

25. The method of claim 14, wherein the subject is also on a restricted diet regimen.

26. The method of claim 14, further comprising administering a second agent.

27. The method of claim 14, wherein the administration ameliorates one or more symptoms of hypoglycemia selected from the group consisting of pancreatic nesidioblastosis, islet cell enlargement, islet cell hyperplasia, β cell budding, tachycardia, diaphoresis, flushing and reduced cognitive function.

28. The method of claim 14, wherein the administration reduces or eliminates hypoglycemia within 20 minutes.

29. The method of claim 14, wherein the antibody fragment has a duration of action of approximately 4 hours.

30. The method of claim 14, wherein the subject is non-responsive to dextrose or glucagon therapy.

31. The method of claim 14, wherein the administration reduces or eliminates hypoglycemia within 15 minutes.

32. The method of claim 26, wherein the second agent is glucagon and/or insulin.

33. A method of preparing a sterile pharmaceutical composition, comprising adding a sterile pharmaceutically acceptable diluent to an antibody of any one of claims 1-3 and 4.

* * * * *

SEQUENCE LISTING

```
<160> NUMBER OF SEQ ID NOS: 112

<210> SEQ ID NO 1
<211> LENGTH: 118
<212> TYPE: PRT
<213> ORGANISM: Homo Sapiens
<220> FEATURE:
<221> NAME/KEY: MISC_FEATURE
<223> OTHER INFORMATION: XPA.15.247 VH

<400> SEQUENCE: 1

Glu Val Gln Leu Val Glu Thr Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Glu Trp Gly Phe Gly Met Asp Val Trp Gly Gln Gly Thr
            100                 105                 110

Thr Val Thr Val Ser Ser
        115

<210> SEQ ID NO 2
<211> LENGTH: 118
<212> TYPE: PRT
<213> ORGANISM: Homo Sapiens
<220> FEATURE:
<221> NAME/KEY: MISC_FEATURE
<223> OTHER INFORMATION: XPA.15.247. 2.018 VH

<400> SEQUENCE: 2

Glu Val Gln Leu Val Glu Thr Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Ser Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Glu Trp Gly Phe Gly Phe Asp Tyr Trp Gly Gln Gly Thr
            100                 105                 110
```

```
Thr Val Thr Val Ser Ser
        115

<210> SEQ ID NO 3
<211> LENGTH: 119
<212> TYPE: PRT
<213> ORGANISM: Homo Sapiens
<220> FEATURE:
<221> NAME/KEY: MISC_FEATURE
<223> OTHER INFORMATION: XPA.15.247 VL

<400> SEQUENCE: 3

Asp Val Val Met Thr Gln Ser Pro Leu Ser Leu Ser Val Thr Leu Gly
1               5                   10                  15

Gln Pro Ala Ser Ile Ser Cys Arg Ser Ser Leu Ser Leu Val Tyr Gly
            20                  25                  30

Asp Glu Asn Thr Tyr Leu Asn Trp Phe Gln Gln Arg Pro Gly Gln Ser
        35                  40                  45

Pro Arg Arg Leu Leu Tyr Lys Val Ser Asp Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Asp Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110

Arg Thr Val Ala Ala Pro Ser
        115

<210> SEQ ID NO 4
<211> LENGTH: 119
<212> TYPE: PRT
<213> ORGANISM: Homo Sapiens
<220> FEATURE:
<221> NAME/KEY: MISC_FEATURE
<223> OTHER INFORMATION: XPA.15.247.2.018 VL

<400> SEQUENCE: 4

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Gly
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Glu Phe Thr Leu Lys Ile
65                  70                  75                  80

Ser Arg Val Glu Ala Glu Asp Val Gly Val Tyr Phe Cys Met Gln Gly
                85                  90                  95

Thr Tyr Trp Pro Gly Thr Phe Gly Gly Gly Thr Lys Leu Glu Ile Lys
            100                 105                 110

Arg Thr Val Ala Ala Pro Ser
        115

<210> SEQ ID NO 5
<211> LENGTH: 8
<212> TYPE: PRT
<213> ORGANISM: Homo Sapiens
```

```
<220> FEATURE:
<221> NAME/KEY: MISC_FEATURE
<223> OTHER INFORMATION: XPA.15.247 VH CDR1

<400> SEQUENCE: 5

Gly Phe Thr Phe Ser Ser Tyr Ala
1               5

<210> SEQ ID NO 6
<211> LENGTH: 8
<212> TYPE: PRT
<213> ORGANISM: Homo Sapiens
<220> FEATURE:
<221> NAME/KEY: MISC_FEATURE
<223> OTHER INFORMATION: XPA.15.247 VH CDR2

<400> SEQUENCE: 6

Ile Ser Tyr Asp Gly Ser Asn Lys
1               5

<210> SEQ ID NO 7
<211> LENGTH: 11
<212> TYPE: PRT
<213> ORGANISM: Homo Sapiens
<220> FEATURE:
<221> NAME/KEY: MISC_FEATURE
<223> OTHER INFORMATION: XPA.15.247 VH CDR3

<400> SEQUENCE: 7

Ala Arg His Glu Trp Gly Phe Gly Met Asp Val
1               5                   10

<210> SEQ ID NO 8
<211> LENGTH: 8
<212> TYPE: PRT
<213> ORGANISM: Homo Sapiens
<220> FEATURE:
<221> NAME/KEY: MISC_FEATURE
<223> OTHER INFORMATION: XPA.15.247.2.018 VH CDR1

<400> SEQUENCE: 8

Gly Phe Thr Phe Ser Ser Tyr Ala
1               5

<210> SEQ ID NO 9
<211> LENGTH: 8
<212> TYPE: PRT
<213> ORGANISM: Homo Sapiens
<220> FEATURE:
<221> NAME/KEY: MISC_FEATURE
<223> OTHER INFORMATION: XPA.15.247.2.018 VH CDR2

<400> SEQUENCE: 9

Ile Ser Tyr Ser Gly Ser Asn Lys
1               5

<210> SEQ ID NO 10
<211> LENGTH: 11
<212> TYPE: PRT
<213> ORGANISM: Homo Sapiens
<220> FEATURE:
<221> NAME/KEY: MISC_FEATURE
<223> OTHER INFORMATION: XPA.15.247.2.018 VH CDR3

<400> SEQUENCE: 10

Ala Arg His Glu Trp Gly Phe Gly Phe Asp Tyr
1               5                   10
```

```
<210> SEQ ID NO 11
<211> LENGTH: 11
<212> TYPE: PRT
<213> ORGANISM: Homo Sapiens
<220> FEATURE:
<221> NAME/KEY: MISC_FEATURE
<223> OTHER INFORMATION: XPA.15.247 VL CDR1

<400> SEQUENCE: 11

Leu Ser Leu Val Tyr Gly Asp Glu Asn Thr Tyr
1               5                   10

<210> SEQ ID NO 12
<211> LENGTH: 3
<212> TYPE: PRT
<213> ORGANISM: Homo Sapiens
<220> FEATURE:
<221> NAME/KEY: MISC_FEATURE
<223> OTHER INFORMATION: XPA.15.247 VL CDR2

<400> SEQUENCE: 12

Lys Val Ser
1

<210> SEQ ID NO 13
<211> LENGTH: 12
<212> TYPE: PRT
<213> ORGANISM: Homo Sapiens
<220> FEATURE:
<221> NAME/KEY: MISC_FEATURE
<223> OTHER INFORMATION: XPA.15.247 VL CDR3

<400> SEQUENCE: 13

Tyr Thr Phe Gly Gln Gly Thr Lys Leu Glu Ile Lys
1               5                   10

<210> SEQ ID NO 14
<211> LENGTH: 11
<212> TYPE: PRT
<213> ORGANISM: Homo Sapiens
<220> FEATURE:
<221> NAME/KEY: MISC_FEATURE
<223> OTHER INFORMATION: XPA.15.247.2.018 VL CDR1

<400> SEQUENCE: 14

Gln Ser Leu Val Tyr Gly Asp Glu Asn Thr Tyr
1               5                   10

<210> SEQ ID NO 15
<211> LENGTH: 3
<212> TYPE: PRT
<213> ORGANISM: Homo Sapiens
<220> FEATURE:
<221> NAME/KEY: MISC_FEATURE
<223> OTHER INFORMATION: XPA.15.247.2.018 VL CDR2

<400> SEQUENCE: 15

Lys Val Ser
1

<210> SEQ ID NO 16
<211> LENGTH: 7
<212> TYPE: PRT
<213> ORGANISM: Homo Sapiens
<220> FEATURE:
<221> NAME/KEY: MISC_FEATURE
<223> OTHER INFORMATION: XPA.15.247.2.018 VL CDR3
```

```
<400> SEQUENCE: 16

Met Gln Gly Thr Tyr Trp Pro
1               5

<210> SEQ ID NO 17
<211> LENGTH: 113
<212> TYPE: PRT
<213> ORGANISM: Homo Sapiens
<220> FEATURE:
<221> NAME/KEY: MISC_FEATURE
<223> OTHER INFORMATION: XPA.15.247.014 VL

<400> SEQUENCE: 17

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Gly
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Lys Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr Tyr Trp Pro Met Thr Phe Gly Gly Gly Thr Lys Leu Glu Ile Lys
            100                 105                 110

Arg

<210> SEQ ID NO 18
<211> LENGTH: 113
<212> TYPE: PRT
<213> ORGANISM: Homo Sapiens
<220> FEATURE:
<221> NAME/KEY: MISC_FEATURE
<223> OTHER INFORMATION: XPA.15.247.011 VL

<400> SEQUENCE: 18

Asp Val Val Met Thr Gln Ser Pro Leu Ser Leu Pro Val Thr Leu Gly
1               5                   10                  15

Gln Pro Ala Ser Ile Ser Cys Arg Ser Ser His Ser Leu Val Tyr Gly
            20                  25                  30

Asp Gly Asn Thr Tyr Leu Asn Trp Phe His Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ala Gly Ser Gly Ser Gly Thr Asp Phe Thr Leu Lys Ile
65                  70                  75                  80

Ser Arg Val Glu Ala Asp Asp Phe Gly Val Phe Tyr Cys Met Gln Gly
                85                  90                  95

Thr His Trp Pro Tyr Thr Phe Gly Gln Gly Thr Lys Leu Glu Ile Lys
            100                 105                 110

Arg

<210> SEQ ID NO 19
<211> LENGTH: 113
<212> TYPE: PRT
<213> ORGANISM: Homo Sapiens
<220> FEATURE:
```

<221> NAME/KEY: MISC_FEATURE
<223> OTHER INFORMATION: XPA.15.247.014 VL CDR1

<400> SEQUENCE: 19

Asp Val Val Met Thr Gln Ser Pro Leu Ser Leu Pro Val Thr Leu Gly
1               5                   10                  15

Gln Pro Ala Ser Ile Ser Cys Arg Ser Ser Glu Ser Leu Val Tyr Gly
            20                  25                  30

Asp Glu Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Ser Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110

Arg

<210> SEQ ID NO 20
<211> LENGTH: 11
<212> TYPE: PRT
<213> ORGANISM: Homo Sapiens
<220> FEATURE:
<221> NAME/KEY: MISC_FEATURE
<223> OTHER INFORMATION: XPA.15.247.014 VL CDR1

<400> SEQUENCE: 20

Gln Ser Leu Val Tyr Gly Asp Gly Asn Thr Tyr
1               5                   10

<210> SEQ ID NO 21
<211> LENGTH: 3
<212> TYPE: PRT
<213> ORGANISM: Homo Sapiens
<220> FEATURE:
<221> NAME/KEY: MISC_FEATURE
<223> OTHER INFORMATION: XPA.15.247.014 VL CDR2

<400> SEQUENCE: 21

Lys Val Ser
1

<210> SEQ ID NO 22
<211> LENGTH: 9
<212> TYPE: PRT
<213> ORGANISM: Homo Sapiens
<220> FEATURE:
<221> NAME/KEY: MISC_FEATURE
<223> OTHER INFORMATION: XPA.15.247.014 VL CDR3

<400> SEQUENCE: 22

Met Gln Gly Thr Tyr Trp Pro Met Thr
1               5

<210> SEQ ID NO 23
<211> LENGTH: 11
<212> TYPE: PRT
<213> ORGANISM: Homo Sapiens
<220> FEATURE:
<221> NAME/KEY: MISC_FEATURE
<223> OTHER INFORMATION: XPA.15.247.011 VL CDR1

<400> SEQUENCE: 23

His Ser Leu Val Tyr Gly Asp Gly Asn Thr Tyr
1               5                   10

<210> SEQ ID NO 24
<211> LENGTH: 3
<212> TYPE: PRT
<213> ORGANISM: Homo Sapiens
<220> FEATURE:
<221> NAME/KEY: MISC_FEATURE
<223> OTHER INFORMATION: XPA.15.247.011 VL CDR2

<400> SEQUENCE: 24

Lys Val Ser
1

<210> SEQ ID NO 25
<211> LENGTH: 9
<212> TYPE: PRT
<213> ORGANISM: Homo Sapiens
<220> FEATURE:
<221> NAME/KEY: MISC_FEATURE
<223> OTHER INFORMATION: XPA.15.247.011 VL CDR3

<400> SEQUENCE: 25

Met Gln Gly Thr His Trp Pro Tyr Thr
1               5

<210> SEQ ID NO 26
<211> LENGTH: 11
<212> TYPE: PRT
<213> ORGANISM: Homo Sapiens
<220> FEATURE:
<221> NAME/KEY: MISC_FEATURE
<223> OTHER INFORMATION: XPA.15.247.019 VL CDR1

<400> SEQUENCE: 26

Glu Ser Leu Val Tyr Gly Asp Glu Asn Thr Tyr
1               5                   10

<210> SEQ ID NO 27
<211> LENGTH: 3
<212> TYPE: PRT
<213> ORGANISM: Homo Sapiens
<220> FEATURE:
<221> NAME/KEY: MISC_FEATURE
<223> OTHER INFORMATION: XPA.15.247.019 VL CDR2

<400> SEQUENCE: 27

Lys Val Ser
1

<210> SEQ ID NO 28
<211> LENGTH: 9
<212> TYPE: PRT
<213> ORGANISM: Homo Sapiens
<220> FEATURE:
<221> NAME/KEY: MISC_FEATURE
<223> OTHER INFORMATION: XPA.15.247.019 VL CDR3

<400> SEQUENCE: 28

Met Gln Gly Thr His Trp Pro Tyr Thr
1               5

<210> SEQ ID NO 29
<211> LENGTH: 118
<212> TYPE: PRT

```
<213> ORGANISM: Homo Sapiens
<220> FEATURE:
<221> NAME/KEY: MISC_FEATURE
<223> OTHER INFORMATION: RHF.15.05896.004 VH

<400> SEQUENCE: 29
```

Glu Val Gln Leu Val Glu Thr Gly Gly Gly Val Val Gln Pro Gly Arg
1               5                   10                  15

Ser Leu Arg Leu Ser Cys Ala Ala Ser Gly Phe Arg Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Ser Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Glu Trp Gly Phe Gly Phe Asp Glu Trp Gly Gln Gly Thr
            100                 105                 110

Thr Val Thr Val Ser Ser
        115

```
<210> SEQ ID NO 30
<211> LENGTH: 118
<212> TYPE: PRT
<213> ORGANISM: Homo sapiens
<220> FEATURE:
<221> NAME/KEY: MISC_FEATURE
<223> OTHER INFORMATION: RHF.15.05896.006 VH

<400> SEQUENCE: 30
```

Glu Val Gln Leu Val Glu Thr Gly Gly Gly Val Val Gln Pro Gly Arg
1               5                   10                  15

Ser Leu Arg Leu Ser Cys Ala Ala Ser Gly Phe Lys Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Ser Gly Asp Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Glu Trp Gly Phe Gly Phe Asp Arg Trp Gly Gln Gly Thr
            100                 105                 110

Thr Val Thr Val Ser Ser
        115

```
<210> SEQ ID NO 31
<211> LENGTH: 118
<212> TYPE: PRT
<213> ORGANISM: Homo sapiens
<220> FEATURE:
<221> NAME/KEY: MISC_FEATURE
<223> OTHER INFORMATION: RHF.15.05896.012 VH

<400> SEQUENCE: 31
```

Glu Val Gln Leu Val Glu Thr Gly Gly Gly Val Val Gln Pro Gly Arg
1               5                   10                  15

```
Ser Leu Arg Leu Ser Cys Ala Ala Ser Gly Phe Thr Phe Ser Ser Trp
         20                  25                  30

Ala Met His Trp Val Arg Gln Ala Pro Gly Lys Gly Leu Glu Trp Val
         35                  40                  45

Ala Val Ile Ser Tyr Ser Gly Glu Asn Lys Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg His Glu Trp Gly Phe Pro Phe Asp Tyr Trp Gly Gln Gly Thr
            100                 105                 110

Thr Val Thr Val Ser Ser
            115

<210> SEQ ID NO 32
<211> LENGTH: 118
<212> TYPE: PRT
<213> ORGANISM: Homo sapiens
<220> FEATURE:
<221> NAME/KEY: MISC_FEATURE
<223> OTHER INFORMATION: RHF.15.05896.015 VH

<400> SEQUENCE: 32

Glu Val Gln Leu Val Glu Thr Gly Gly Gly Val Val Gln Pro Gly Arg
  1               5                  10                  15

Ser Leu Arg Leu Ser Cys Ala Ala Ser Gly Phe Lys Phe Ser Ser Tyr
             20                  25                  30

Ala Met His Trp Val Arg Gln Ala Pro Gly Lys Gly Leu Glu Trp Val
         35                  40                  45

Ala Val Ile Ser Tyr Ser Gly Arg Asn Lys Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
             85                  90                  95

Ala Arg His Glu Trp Gly Phe Gly Asp Tyr Trp Gly Gln Gly Thr
            100                 105                 110

Thr Val Thr Val Ser Ser
            115

<210> SEQ ID NO 33
<211> LENGTH: 118
<212> TYPE: PRT
<213> ORGANISM: Homo sapiens
<220> FEATURE:
<221> NAME/KEY: MISC_FEATURE
<223> OTHER INFORMATION: RHF.15.05896.020 VH

<400> SEQUENCE: 33

Glu Val Gln Leu Val Glu Thr Gly Gly Gly Val Val Gln Pro Gly Arg
  1               5                  10                  15

Ser Leu Arg Leu Ser Cys Ala Ala Ser Gly Phe Lys Phe Ser Ser Tyr
             20                  25                  30

Ala Met His Trp Val Arg Gln Ala Pro Gly Lys Gly Leu Glu Trp Val
         35                  40                  45

Ala Val Ile Ser Trp Ser Gly Ser Asn Lys Tyr Tyr Ala Asp Ser Val
    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg His Glu Trp Gly Phe Gly Phe Asp Gly Trp Gly Gln Gly Thr
            100                 105                 110

Thr Val Thr Val Ser Ser
            115

<210> SEQ ID NO 34
<211> LENGTH: 118
<212> TYPE: PRT
<213> ORGANISM: Homo sapiens
<220> FEATURE:
<221> NAME/KEY: MISC_FEATURE
<223> OTHER INFORMATION: RHF.15.05896.022 VH

<400> SEQUENCE: 34

Glu Val Gln Leu Val Glu Thr Gly Gly Gly Val Val Gln Pro Gly Arg
 1               5                  10                  15

Ser Leu Arg Leu Ser Cys Ala Ala Ser Gly Phe Thr Phe Ser Ser Trp
                20                  25                  30

Ala Met His Trp Val Arg Gln Ala Pro Gly Lys Gly Leu Glu Trp Val
            35                  40                  45

Ala Val Ile Ser Tyr Ser Gly Ser Asn Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg His Glu Trp Gly Phe Pro Phe Asp Tyr Trp Gly Gln Gly Thr
            100                 105                 110

Thr Val Thr Val Ser Ser
            115

<210> SEQ ID NO 35
<211> LENGTH: 118
<212> TYPE: PRT
<213> ORGANISM: Homo sapiens
<220> FEATURE:
<221> NAME/KEY: MISC_FEATURE
<223> OTHER INFORMATION: RHF.15.05896.028 VH

<400> SEQUENCE: 35

Glu Val Gln Leu Val Glu Thr Gly Gly Gly Val Val Gln Pro Gly Arg
 1               5                  10                  15

Ser Leu Arg Leu Ser Cys Ala Ala Ser Gly Phe Lys Phe Ser Ser Tyr
                20                  25                  30

Ala Met His Trp Val Arg Gln Ala Pro Gly Lys Gly Leu Glu Trp Val
            35                  40                  45

Ala Val Ile Ser Gly Ser Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg His Glu Trp Gly Leu Gly Phe Asp Tyr Trp Gly Gln Gly Thr
            100                 105                 110
```

Thr Val Thr Val Ser Ser
        115

<210> SEQ ID NO 36
<211> LENGTH: 118
<212> TYPE: PRT
<213> ORGANISM: Homo sapiens
<220> FEATURE:
<221> NAME/KEY: MISC_FEATURE
<223> OTHER INFORMATION: RHF.15.05896.032 VH

<400> SEQUENCE: 36

Glu Val Gln Leu Val Glu Thr Gly Gly Gly Val Val Gln Pro Gly Arg
1               5                   10                  15

Ser Leu Arg Leu Ser Cys Ala Ala Ser Gly Phe Lys Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Ser Gly Glu Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Glu Trp Gly Phe Gly Phe Asp Glu Trp Gly Gln Gly Thr
            100                 105                 110

Thr Val Thr Val Ser Ser
        115

<210> SEQ ID NO 37
<211> LENGTH: 118
<212> TYPE: PRT
<213> ORGANISM: Homo sapiens
<220> FEATURE:
<221> NAME/KEY: MISC_FEATURE
<223> OTHER INFORMATION: RHF.15.05896.036 VH

<400> SEQUENCE: 37

Glu Val Gln Leu Val Glu Thr Gly Gly Gly Val Val Gln Pro Gly Arg
1               5                   10                  15

Ser Leu Arg Leu Ser Cys Ala Ala Ser Gly Phe Lys Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Ser Gly Gly Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Glu Trp Gly Phe Gly Phe Asp Leu Trp Gly Gln Gly Thr
            100                 105                 110

Thr Val Thr Val Ser Ser
        115

<210> SEQ ID NO 38
<211> LENGTH: 118
<212> TYPE: PRT
<213> ORGANISM: Homo sapiens -continued

```
<220> FEATURE:
<221> NAME/KEY: MISC_FEATURE
<223> OTHER INFORMATION: RHF.15.05896.040 VH

<400> SEQUENCE: 38

Glu Val Gln Leu Val Glu Thr Gly Gly Gly Val Val Gln Pro Gly Arg
1               5                   10                  15

Ser Leu Arg Leu Ser Cys Ala Ala Ser Gly Phe Lys Phe Ser Ser Tyr
            20                  25                  30

Ala Met His Trp Val Arg Gln Ala Pro Gly Lys Gly Leu Glu Trp Val
        35                  40                  45

Ala Val Ile Ser Asn Ser Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Glu Trp Gly Phe Gly Phe Asp Trp Trp Gly Gln Gly Thr
            100                 105                 110

Thr Val Thr Val Ser Ser
        115

<210> SEQ ID NO 39
<211> LENGTH: 118
<212> TYPE: PRT
<213> ORGANISM: Homo sapiens
<220> FEATURE:
<221> NAME/KEY: MISC_FEATURE
<223> OTHER INFORMATION: RHF.15.05896.044 VH

<400> SEQUENCE: 39

Glu Val Gln Leu Val Glu Thr Gly Gly Gly Val Val Gln Pro Gly Arg
1               5                   10                  15

Ser Leu Arg Leu Ser Cys Ala Ala Ser Gly Phe Lys Phe Ser Ser Tyr
            20                  25                  30

Ala Met His Trp Val Arg Gln Ala Pro Gly Lys Gly Leu Glu Trp Val
        35                  40                  45

Ala Val Ile Ser Asn Ser Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Glu Trp Gly Phe Gly Phe Asp Lys Trp Gly Gln Gly Thr
            100                 105                 110

Thr Val Thr Val Ser Ser
        115

<210> SEQ ID NO 40
<211> LENGTH: 118
<212> TYPE: PRT
<213> ORGANISM: Homo sapiens
<220> FEATURE:
<221> NAME/KEY: MISC_FEATURE
<223> OTHER INFORMATION: RHF.15.05896.048 VH

<400> SEQUENCE: 40

Glu Val Gln Leu Val Glu Thr Gly Gly Gly Val Val Gln Pro Gly Arg
1               5                   10                  15
```

```
Ser Leu Arg Leu Ser Cys Ala Ala Ser Gly Phe Thr Phe Arg Ser Tyr
            20                  25                  30

Ala Met His Trp Val Arg Gln Ala Pro Gly Lys Gly Leu Glu Trp Val
        35                  40                  45

Ala Val Ile Ser Tyr Ser Gly Ser Val Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Glu Trp Gly Phe Gly Phe Asp Glu Trp Gly Gln Gly Thr
            100                 105                 110

Thr Val Thr Val Ser Ser
            115

<210> SEQ ID NO 41
<211> LENGTH: 118
<212> TYPE: PRT
<213> ORGANISM: Homo sapiens
<220> FEATURE:
<221> NAME/KEY: MISC_FEATURE
<223> OTHER INFORMATION: RHF.15.05896.052 VH

<400> SEQUENCE: 41

Glu Val Gln Leu Val Glu Thr Gly Gly Gly Val Val Gln Pro Gly Arg
1               5                   10                  15

Ser Leu Arg Leu Ser Cys Ala Ala Ser Gly Phe Lys Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Ser Gly Gly Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Glu Trp Gly Phe Gly Phe Asp Glu Trp Gly Gln Gly Thr
            100                 105                 110

Thr Val Thr Val Ser Ser
            115

<210> SEQ ID NO 42
<211> LENGTH: 118
<212> TYPE: PRT
<213> ORGANISM: Homo sapiens
<220> FEATURE:
<221> NAME/KEY: MISC_FEATURE
<223> OTHER INFORMATION: RHF.15.05896.056 VH

<400> SEQUENCE: 42

Glu Val Gln Leu Val Glu Thr Gly Gly Gly Val Val Gln Pro Gly Arg
1               5                   10                  15

Ser Leu Arg Leu Ser Cys Ala Ala Ser Gly Phe Lys Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Gly Gly Ser Asn Lys Tyr Tyr Ala Asp Ser Val
    50                  55                  60
```

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Glu Trp Gly Phe Gly Phe Asp Glu Trp Gly Gln Gly Thr
            100                 105                 110

Thr Val Thr Val Ser Ser
            115

<210> SEQ ID NO 43
<211> LENGTH: 118
<212> TYPE: PRT
<213> ORGANISM: Homo sapiens
<220> FEATURE:
<221> NAME/KEY: MISC_FEATURE
<223> OTHER INFORMATION: RHF.15.05896.059 VH

<400> SEQUENCE: 43

Glu Val Gln Leu Val Glu Thr Gly Gly Gly Val Val Gln Pro Gly Arg
1               5                   10                  15

Ser Leu Arg Leu Ser Cys Ala Ala Ser Gly Phe Arg Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Ser Gly Ser Val Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Glu Trp Gly Phe Gly Phe Asp Arg Trp Gly Gln Gly Thr
            100                 105                 110

Thr Val Thr Val Ser Ser
            115

<210> SEQ ID NO 44
<211> LENGTH: 118
<212> TYPE: PRT
<213> ORGANISM: Homo sapiens
<220> FEATURE:
<221> NAME/KEY: MISC_FEATURE
<223> OTHER INFORMATION: RHF.15.05896.064 VH

<400> SEQUENCE: 44

Glu Val Gln Leu Val Glu Thr Gly Gly Gly Val Val Gln Pro Gly Arg
1               5                   10                  15

Ser Leu Arg Leu Ser Cys Ala Ala Ser Gly Phe Lys Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Ser Gly Ser His Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Glu Trp Gly Phe Gly Gln Asp Tyr Trp Gly Gln Gly Thr
            100                 105                 110

Thr Val Thr Val Ser Ser
      115

<210> SEQ ID NO 45
<211> LENGTH: 118
<212> TYPE: PRT
<213> ORGANISM: Homo sapiens
<220> FEATURE:
<221> NAME/KEY: MISC_FEATURE
<223> OTHER INFORMATION: RHF.15.05896.068 VH

<400> SEQUENCE: 45

```
Glu Val Gln Leu Val Glu Thr Gly Gly Gly Val Val Gln Pro Gly Arg
1               5                   10                  15

Ser Leu Arg Leu Ser Cys Ala Ala Ser Gly Phe Lys Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Ser Gly Gly Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Glu Trp Gly Phe Gly Tyr Asp Tyr Trp Gly Gln Gly Thr
            100                 105                 110

Thr Val Thr Val Ser Ser
        115
```

<210> SEQ ID NO 46
<211> LENGTH: 118
<212> TYPE: PRT
<213> ORGANISM: Homo sapiens
<220> FEATURE:
<221> NAME/KEY: MISC_FEATURE
<223> OTHER INFORMATION: RHF.15.05896.072 VH

<400> SEQUENCE: 46

```
Glu Val Gln Leu Val Glu Thr Gly Gly Gly Val Val Gln Pro Gly Arg
1               5                   10                  15

Ser Leu Arg Leu Ser Cys Ala Ala Ser Gly Phe Arg Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Ser Gly Gly Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Glu Trp Gly Phe Gly Tyr Asp Tyr Trp Gly Gln Gly Thr
            100                 105                 110

Thr Val Thr Val Ser Ser
        115
```

<210> SEQ ID NO 47
<211> LENGTH: 118
<212> TYPE: PRT
<213> ORGANISM: Homo sapiens
<220> FEATURE:

<221> NAME/KEY: MISC_FEATURE
<223> OTHER INFORMATION: RHF.15.05896.075 VH

<400> SEQUENCE: 47

Glu Val Gln Leu Val Glu Thr Gly Gly Gly Val Val Gln Pro Gly Arg
1               5                   10                  15

Ser Leu Arg Leu Ser Cys Ala Ala Ser Gly Phe Lys Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Ser Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Glu Trp Gly Phe Gly Tyr Asp Tyr Trp Gly Gln Gly Thr
            100                 105                 110

Thr Val Thr Val Ser Ser
            115

<210> SEQ ID NO 48
<211> LENGTH: 118
<212> TYPE: PRT
<213> ORGANISM: Homo sapiens
<220> FEATURE:
<221> NAME/KEY: MISC_FEATURE
<223> OTHER INFORMATION: RHF.15.05896.079 VH

<400> SEQUENCE: 48

Glu Val Gln Leu Val Glu Thr Gly Gly Gly Val Val Gln Pro Gly Arg
1               5                   10                  15

Ser Leu Arg Leu Ser Cys Ala Ala Ser Gly Phe Lys Phe Ser Ser Tyr
            20                  25                  30

Ala Met His Trp Val Arg Gln Ala Pro Gly Lys Gly Leu Glu Trp Val
        35                  40                  45

Ala Val Ile Ser Trp Ser Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Glu Trp Gly Phe Gly Tyr Asp Tyr Trp Gly Gln Gly Thr
            100                 105                 110

Thr Val Thr Val Ser Ser
            115

<210> SEQ ID NO 49
<211> LENGTH: 118
<212> TYPE: PRT
<213> ORGANISM: Homo sapiens
<220> FEATURE:
<221> NAME/KEY: MISC_FEATURE
<223> OTHER INFORMATION: RHF.15.05896.084 VH

<400> SEQUENCE: 49

Glu Val Gln Leu Val Glu Thr Gly Gly Gly Val Val Gln Pro Gly Arg
1               5                   10                  15

Ser Leu Arg Leu Ser Cys Ala Ala Ser Gly Phe Arg Phe Ser Ser Tyr

```
                    20                  25                  30
Ala Met His Trp Val Arg Gln Ala Pro Gly Lys Gly Leu Glu Trp Val
            35                  40                  45
Ala Val Ile Ser Trp Ser Gly Ser Asn Lys Tyr Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg His Glu Trp Gly Phe Gly Phe Asp Lys Trp Gly Gln Gly Thr
            100                 105                 110
Thr Val Thr Val Ser Ser
        115

<210> SEQ ID NO 50
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.004 H-CDR1

<400> SEQUENCE: 50

Gly Phe Arg Phe Ser Ser Tyr Ala
1               5

<210> SEQ ID NO 51
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.004 H-CDR2

<400> SEQUENCE: 51

Ile Ser Tyr Ser Gly Ser Asn Lys
1               5

<210> SEQ ID NO 52
<211> LENGTH: 11
<212> TYPE: PRT
<213> ORGANISM: Homo sapiens
<220> FEATURE:
<221> NAME/KEY: MISC_FEATURE
<223> OTHER INFORMATION: RHF.15.05896.004 H-CDR3

<400> SEQUENCE: 52

Ala Arg His Glu Trp Gly Phe Gly Phe Asp Glu
1               5                   10

<210> SEQ ID NO 53
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.006 H-CDR1

<400> SEQUENCE: 53

Gly Phe Lys Phe Ser Ser Tyr Ala
1               5

<210> SEQ ID NO 54
<211> LENGTH: 8
```

```
<212> TYPE: PRT
<213> ORGANISM: Homo sapiens
<220> FEATURE:
<221> NAME/KEY: MISC_FEATURE
<223> OTHER INFORMATION: RHF.15.05896.006 H-CDR2

<400> SEQUENCE: 54

Ile Ser Tyr Ser Gly Asp Asn Lys
1               5

<210> SEQ ID NO 55
<211> LENGTH: 11
<212> TYPE: PRT
<213> ORGANISM: Homo sapiens
<220> FEATURE:
<221> NAME/KEY: MISC_FEATURE
<223> OTHER INFORMATION: RHF.15.05896.006 H-CDR3

<400> SEQUENCE: 55

Ala Arg His Glu Trp Gly Phe Gly Phe Asp Arg
1               5                   10

<210> SEQ ID NO 56
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.012 H-CDR1

<400> SEQUENCE: 56

Gly Phe Thr Phe Ser Ser Trp Ala
1               5

<210> SEQ ID NO 57
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.012 H-CDR2

<400> SEQUENCE: 57

Ile Ser Tyr Ser Gly Glu Asn Lys
1               5

<210> SEQ ID NO 58
<211> LENGTH: 11
<212> TYPE: PRT
<213> ORGANISM: Homo sapiens
<220> FEATURE:
<221> NAME/KEY: MISC_FEATURE
<223> OTHER INFORMATION: RHF.15.05896.012 H-CDR3

<400> SEQUENCE: 58

Ala Arg His Glu Trp Gly Phe Pro Phe Asp Tyr
1               5                   10

<210> SEQ ID NO 59
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.015 H-CDR1

<400> SEQUENCE: 59

Gly Phe Lys Phe Ser Ser Tyr Ala
```

<210> SEQ ID NO 60
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.015 H-CDR2

<400> SEQUENCE: 60

Ile Ser Tyr Ser Gly Arg Asn Lys
1               5

<210> SEQ ID NO 61
<211> LENGTH: 11
<212> TYPE: PRT
<213> ORGANISM: Homo sapiens
<220> FEATURE:
<221> NAME/KEY: MISC_FEATURE
<223> OTHER INFORMATION: RHF.15.05896.015 H-CDR3

<400> SEQUENCE: 61

Ala Arg His Glu Trp Gly Phe Gly Gln Asp Tyr
1               5                   10

<210> SEQ ID NO 62
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.020 H-CDR1

<400> SEQUENCE: 62

Gly Phe Lys Phe Ser Ser Tyr Ala
1               5

<210> SEQ ID NO 63
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.020 H-CDR2

<400> SEQUENCE: 63

Ile Ser Trp Ser Gly Ser Asn Lys
1               5

<210> SEQ ID NO 64
<211> LENGTH: 11
<212> TYPE: PRT
<213> ORGANISM: Homo sapiens
<220> FEATURE:
<221> NAME/KEY: MISC_FEATURE
<223> OTHER INFORMATION: RHF.15.05896.020 H-CDR3

<400> SEQUENCE: 64

Ala Arg His Glu Trp Gly Phe Gly Phe Asp Glu
1               5                   10

<210> SEQ ID NO 65
<211> LENGTH: 8
<212> TYPE: PRT
<213> ORGANISM: Homo sapiens
<220> FEATURE:
<221> NAME/KEY: MISC_FEATURE

<223> OTHER INFORMATION: RHF.15.05896.022 H-CDR1

<400> SEQUENCE: 65

Gly Phe Thr Phe Ser Ser Trp Ala
1               5

<210> SEQ ID NO 66
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.022 H-CDR2

<400> SEQUENCE: 66

Ile Ser Tyr Ser Gly Ser Asn Thr
1               5

<210> SEQ ID NO 67
<211> LENGTH: 11
<212> TYPE: PRT
<213> ORGANISM: Homo sapiens
<220> FEATURE:
<221> NAME/KEY: MISC_FEATURE
<223> OTHER INFORMATION: RHF.15.05896.022 H-CDR3

<400> SEQUENCE: 67

Ala Arg His Glu Trp Gly Phe Pro Phe Asp Tyr
1               5                   10

<210> SEQ ID NO 68
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.028 H-CDR1

<400> SEQUENCE: 68

Gly Phe Lys Phe Ser Ser Tyr Ala
1               5

<210> SEQ ID NO 69
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.028 H-CDR2

<400> SEQUENCE: 69

Ile Ser Gly Ser Gly Ser Asn Lys
1               5

<210> SEQ ID NO 70
<211> LENGTH: 11
<212> TYPE: PRT
<213> ORGANISM: Homo sapiens
<220> FEATURE:
<221> NAME/KEY: MISC_FEATURE
<223> OTHER INFORMATION: RHF.15.05896.028 H-CDR3

<400> SEQUENCE: 70

Ala Arg His Glu Trp Gly Leu Gly Phe Asp Tyr
1               5                   10

<210> SEQ ID NO 71

```
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.032 H-CDR1

<400> SEQUENCE: 71

Gly Phe Lys Phe Ser Ser Tyr Ala
1               5

<210> SEQ ID NO 72
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.032 H-CDR2

<400> SEQUENCE: 72

Ile Ser Tyr Ser Gly Glu Asn Lys
1               5

<210> SEQ ID NO 73
<211> LENGTH: 11
<212> TYPE: PRT
<213> ORGANISM: Homo sapiens
<220> FEATURE:
<221> NAME/KEY: MISC_FEATURE
<223> OTHER INFORMATION: RHF.15.05896.032 H-CDR3

<400> SEQUENCE: 73

Ala Arg His Glu Trp Gly Phe Gly Phe Asp Glu
1               5                   10

<210> SEQ ID NO 74
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.036 H-CDR1

<400> SEQUENCE: 74

Gly Phe Lys Phe Ser Ser Tyr Ala
1               5

<210> SEQ ID NO 75
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.036 H-CDR2

<400> SEQUENCE: 75

Ile Ser Tyr Ser Gly Gly Asn Lys
1               5

<210> SEQ ID NO 76
<211> LENGTH: 11
<212> TYPE: PRT
<213> ORGANISM: Homo sapiens
<220> FEATURE:
<221> NAME/KEY: MISC_FEATURE
<223> OTHER INFORMATION: RHF.15.05896.036 H-CDR3

<400> SEQUENCE: 76
```

Ala Arg His Glu Trp Gly Phe Gly Phe Asp Leu
1               5                   10

<210> SEQ ID NO 77
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.040 H-CDR1

<400> SEQUENCE: 77

Gly Phe Lys Phe Ser Ser Tyr Ala
1               5

<210> SEQ ID NO 78
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.040 H-CDR2

<400> SEQUENCE: 78

Ile Ser Asn Ser Gly Ser Asn Lys
1               5

<210> SEQ ID NO 79
<211> LENGTH: 11
<212> TYPE: PRT
<213> ORGANISM: Homo sapiens
<220> FEATURE:
<221> NAME/KEY: MISC_FEATURE
<223> OTHER INFORMATION: RHF.15.05896.040 H-CDR3

<400> SEQUENCE: 79

Ala Arg His Glu Trp Gly Phe Gly Phe Asp Trp
1               5                   10

<210> SEQ ID NO 80
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.044 H-CDR1

<400> SEQUENCE: 80

Gly Phe Lys Phe Ser Ser Tyr Ala
1               5

<210> SEQ ID NO 81
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.044 H-CDR2

<400> SEQUENCE: 81

Ile Ser Asn Ser Gly Ser Asn Lys
1               5

<210> SEQ ID NO 82
<211> LENGTH: 11
<212> TYPE: PRT
<213> ORGANISM: Homo sapiens
<220> FEATURE:

```
<221> NAME/KEY: MISC_FEATURE
<223> OTHER INFORMATION: RHF.15.05896.044 H-CDR3

<400> SEQUENCE: 82

Ala Arg His Glu Trp Gly Phe Gly Phe Asp Lys
1               5                   10

<210> SEQ ID NO 83
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.048 H-CDR1

<400> SEQUENCE: 83

Gly Phe Thr Phe Arg Ser Tyr Ala
1               5

<210> SEQ ID NO 84
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.048 H-CDR2

<400> SEQUENCE: 84

Ile Ser Tyr Ser Gly Ser Val Lys
1               5

<210> SEQ ID NO 85
<211> LENGTH: 11
<212> TYPE: PRT
<213> ORGANISM: Homo sapiens
<220> FEATURE:
<221> NAME/KEY: MISC_FEATURE
<223> OTHER INFORMATION: RHF.15.05896.048 H-CDR3

<400> SEQUENCE: 85

Ala Arg His Glu Trp Gly Phe Gly Phe Asp Glu
1               5                   10

<210> SEQ ID NO 86
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.052 H-CDR1

<400> SEQUENCE: 86

Gly Phe Lys Phe Ser Ser Tyr Ala
1               5

<210> SEQ ID NO 87
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.052 H-CDR2

<400> SEQUENCE: 87

Ile Ser Tyr Ser Gly Gly Asn Lys
1               5
```

```
<210> SEQ ID NO 88
<211> LENGTH: 11
<212> TYPE: PRT
<213> ORGANISM: Homo sapiens
<220> FEATURE:
<221> NAME/KEY: MISC_FEATURE
<223> OTHER INFORMATION: RHF.15.05896.052 H-CDR3

<400> SEQUENCE: 88

Ala Arg His Glu Trp Gly Phe Gly Phe Asp Glu
1               5                   10

<210> SEQ ID NO 89
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.056 H-CDR1

<400> SEQUENCE: 89

Gly Phe Lys Phe Ser Ser Tyr Ala
1               5

<210> SEQ ID NO 90
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.056 H-CDR2

<400> SEQUENCE: 90

Ile Ser Tyr Gly Gly Ser Asn Lys
1               5

<210> SEQ ID NO 91
<211> LENGTH: 11
<212> TYPE: PRT
<213> ORGANISM: Homo sapiens
<220> FEATURE:
<221> NAME/KEY: MISC_FEATURE
<223> OTHER INFORMATION: RHF.15.05896.056 H-CDR3

<400> SEQUENCE: 91

Ala Arg His Glu Trp Gly Phe Gly Phe Asp Glu
1               5                   10

<210> SEQ ID NO 92
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.059 H-CDR1

<400> SEQUENCE: 92

Gly Phe Arg Phe Ser Ser Tyr Ala
1               5

<210> SEQ ID NO 93
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.059 H-CDR2

<400> SEQUENCE: 93
```

Ile Ser Tyr Ser Gly Ser Val Lys
1               5

<210> SEQ ID NO 94
<211> LENGTH: 11
<212> TYPE: PRT
<213> ORGANISM: Homo sapiens
<220> FEATURE:
<221> NAME/KEY: MISC_FEATURE
<223> OTHER INFORMATION: RHF.15.05896.059 H-CDR3

<400> SEQUENCE: 94

Ala Arg His Glu Trp Gly Phe Gly Phe Asp Arg
1               5                   10

<210> SEQ ID NO 95
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.064 H-CDR1

<400> SEQUENCE: 95

Gly Phe Lys Phe Ser Ser Tyr Ala
1               5

<210> SEQ ID NO 96
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.064 H-CDR2

<400> SEQUENCE: 96

Ile Ser Tyr Ser Gly Ser His Lys
1               5

<210> SEQ ID NO 97
<211> LENGTH: 11
<212> TYPE: PRT
<213> ORGANISM: Homo sapiens
<220> FEATURE:
<221> NAME/KEY: MISC_FEATURE
<223> OTHER INFORMATION: RHF.15.05896.064 H-CDR3

<400> SEQUENCE: 97

Ala Arg His Glu Trp Gly Phe Gly Gln Asp Tyr
1               5                   10

<210> SEQ ID NO 98
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.068  H-CDR1

<400> SEQUENCE: 98

Gly Phe Lys Phe Ser Ser Tyr Ala
1               5

<210> SEQ ID NO 99
<211> LENGTH: 8
<212> TYPE: PRT
<213> ORGANISM: Homo sapiens

```
<220> FEATURE:
<221> NAME/KEY: MISC_FEATURE
<223> OTHER INFORMATION: RHF.15.05896.068 H-CDR2

<400> SEQUENCE: 99

Ile Ser Tyr Ser Gly Gly Asn Lys
1               5

<210> SEQ ID NO 100
<211> LENGTH: 11
<212> TYPE: PRT
<213> ORGANISM: Homo sapiens
<220> FEATURE:
<221> NAME/KEY: MISC_FEATURE
<223> OTHER INFORMATION: RHF.15.05896.068 H-CDR3

<400> SEQUENCE: 100

Ala Arg His Glu Trp Gly Phe Gly Tyr Asp Tyr
1               5                   10

<210> SEQ ID NO 101
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.072 H-CDR1

<400> SEQUENCE: 101

Gly Phe Arg Phe Ser Ser Tyr Ala
1               5

<210> SEQ ID NO 102
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.072 H-CDR2

<400> SEQUENCE: 102

Ile Ser Tyr Ser Gly Gly Asn Lys
1               5

<210> SEQ ID NO 103
<211> LENGTH: 11
<212> TYPE: PRT
<213> ORGANISM: Homo sapiens
<220> FEATURE:
<221> NAME/KEY: MISC_FEATURE
<223> OTHER INFORMATION: RHF.15.05896.072 H-CDR3

<400> SEQUENCE: 103

Ala Arg His Glu Trp Gly Phe Gly Tyr Asp Tyr
1               5                   10

<210> SEQ ID NO 104
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.075 H-CDR1

<400> SEQUENCE: 104

Gly Phe Lys Phe Ser Ser Tyr Ala
1               5
```

<210> SEQ ID NO 105
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.075 H-CDR2

<400> SEQUENCE: 105

Ile Ser Tyr Ser Gly Ser Asn Lys
1               5

<210> SEQ ID NO 106
<211> LENGTH: 11
<212> TYPE: PRT
<213> ORGANISM: Homo sapiens
<220> FEATURE:
<221> NAME/KEY: MISC_FEATURE
<223> OTHER INFORMATION: RHF.15.05896.075 H-CDR3

<400> SEQUENCE: 106

Ala Arg His Glu Trp Gly Phe Gly Tyr Asp Tyr
1               5                   10

<210> SEQ ID NO 107
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.079 H-CDR1

<400> SEQUENCE: 107

Gly Phe Lys Phe Ser Ser Tyr Ala
1               5

<210> SEQ ID NO 108
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.079 H-CDR2

<400> SEQUENCE: 108

Ile Ser Trp Ser Gly Ser Asn Lys
1               5

<210> SEQ ID NO 109
<211> LENGTH: 11
<212> TYPE: PRT
<213> ORGANISM: Homo sapiens
<220> FEATURE:
<221> NAME/KEY: MISC_FEATURE
<223> OTHER INFORMATION: RHF.15.05896.079 H-CDR3

<400> SEQUENCE: 109

Ala Arg His Glu Trp Gly Phe Gly Tyr Asp Tyr
1               5                   10

<210> SEQ ID NO 110
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.084 H-CDR1

```
<400> SEQUENCE: 110

Gly Phe Arg Phe Ser Ser Tyr Ala
1               5

<210> SEQ ID NO 111
<211> LENGTH: 8
<212> TYPE: PRT
<213> ORGANISM: Homo sapiens
<220> FEATURE:
<221> NAME/KEY: MISC_FEATURE
<223> OTHER INFORMATION: RHF.15.05896.084 H-CDR2

<400> SEQUENCE: 111

Ile Ser Trp Ser Gly Ser Asn Lys
1               5

<210> SEQ ID NO 112
<211> LENGTH: 11
<212> TYPE: PRT
<213> ORGANISM: Homo sapiens
<220> FEATURE:
<221> NAME/KEY: MISC_FEATURE
<223> OTHER INFORMATION: RHF.15.05896.084 H-CDR3

<400> SEQUENCE: 112

Ala Arg His Glu Trp Gly Phe Gly Phe Asp Lys
1               5                   10
```